US006544766B1

(12) United States Patent
Beraud et al.

(10) Patent No.: US 6,544,766 B1
(45) Date of Patent: Apr. 8, 2003

(54) HUMAN KINESINS AND METHODS OF PRODUCING AND PURIFYING HUMAN KINESINS

(75) Inventors: Christophe Beraud, San Francisco, CA (US); Cara Ohashi, San Francisco, CA (US); Roman Sakowicz, Foster City, CA (US); Eugeni Vaisberg, Foster City, CA (US); Ken Wood, Foster City, CA (US); Ming Yu, Foster City, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 30 days.

(21) Appl. No.: 09/595,684

(22) Filed: Jun. 16, 2000

Related U.S. Application Data

(63) Continuation of application No. 09/295,612, filed on Apr. 20, 1999, now abandoned.

(51) Int. Cl.[7] .......................... C12N 9/16; C12N 15/00; C12N 5/00; C12N 1/20; C07K 1/00

(52) U.S. Cl. .................... 435/196; 530/350; 435/252.3; 435/325; 435/320.1

(58) Field of Search .......................... 530/350; 435/196, 435/320.1, 252.3, 325

(56) References Cited

FOREIGN PATENT DOCUMENTS

WO WO 99/13061 3/1999

OTHER PUBLICATIONS

Sambrook et al., Molecular Cloning Laboratory Manual, 2nd edition, Cold Spring Harbor Laboratory Press, 1989.*

Ando et al., Immunogenetics, 39, 194–200, 194.*

Pierce et al. (1997) "Imaging individual green fluorescent proteins," Nature, 388:338.

Walczak et al. (1996) "XKCMI: A Xenopus kinesin–related protein that regulates microtubule dynamics during mitotic spindle assembly," Cell 84:37–47.

Vale et al. (1996) "Direct observation of single kinesin molecules moving along microtubules" Nature 380:451–453.

Debernardi et al. (1997) "Identification of a novel human kinesin–related gene (HK2) by the cDNA differential display technique" Genomics 42:67–73.

Adams et al. (1998) "Pavarotti encodes a kinesin–like protein required to organized the central spindle and contractile ring for cytokinesis" Genes & Development 12:1483–1494.

Blangy et al. (1995) "Phosphorylation by per regulates spindle association of human Eg5, a kinesin–related motor essential for bipolar spindle formation in vivo" Cell 83:1159–1169.

Kuriyama et al. (1994) "Heterogeneity and microtubule interaction of the CHO1 antigen, a mitosis–specific kinesin–like protein" Journal of Cell Science 107:3485–3499.

Le Guellec et al. (1991) "Cloning by differential screening of a Xenopus cDNA that encodes" Molecular and Cellular Biology 11:3395–3398.

Lockhart et al. (1996) "Kinetics and motility of the Eg5 microtubules motor" Biochemistry 35:2365–2373.

Nislow et al. (1992) "A plus–end directed motor enzyme that moves antiparallel microtubules in vitro localizes to the interzone of mitotic spindles" Nature 359:543–547.

Raich et al. (1998) "Cytokinesis and midzone microtubule organization if C. elegans require the kinesin–like protein ZEN–4" Molecular Biology of the Cell 9:2037–2049.

Sawin et al. (1992) "Mitotic spindle organization by a plus–end directed microtubule motor" Nature 359, 540–543.

Okada et al. (1999) "A processive single–headed motor: Kinesin superfamily protein KiflA" Science 283:1152–1157.

Thrower et al. (1995) "Mitotic HeLa cells contain a CENP–associated minus end–directed microtubule motor" EMBO 14:918–926.

Desai et al. (1999) "Kin 1 Kinesins and microtubule–destabilizing enzymes" Cell 96:69–78.

Aizawa et al. (1992) "Kinesin family in murine central nervous system" Journal of Cell Biology 119:1287–1296.

Noda et al. (1995) "Kif2 is a new microtubule–based anterograde motor that transports membranous organelles distinct from those carried by a kinesin heavy chain or Kif3 A/B" Journal of Cell Biology 129:157–167.

Crevel et al. (1997) "Kinetic evidence for low chemical processivity in ncd and Eg5" J. Mol. Biol. 273:160–170.

Whitehead et al. (1996) "The spindle kinesin–like protein HsEg5 is an autoantigen in systemic lupus erythematosus" Arthritis and Rheumatism 39:1635–1642.

Wordeman et al. (1995) "Identification and partial characterization of mitotic centromere–associated kinesin, a kinesin–related protein that associates with centromeres during mitosis" J. Cell Biol. 128:95–105.

Sekine et al. (1994) "A novel microtubule–based motor protein (Kif4) for organelle transport, whose expression is regulated developmentally" J. Cell Biol. 127:187–201.

Wang et al. (1995) "Chromokinesin: A DNA–binding, kinesin–like nuclear protein" J. Cell Biol. 128:761–768.

Wood et al. (1997) "CENP–E is a plus end–directed kinetochore motor required for metaphase chromosome alignment" Cell 91:357–366.

Yen et al. (1992) "CENP–E is a putative kinetochore motor that accumulates just before mitosis" Nature 359:536–539.

* cited by examiner

*Primary Examiner*—M. Monshipouri
(74) *Attorney, Agent, or Firm*—Lauren L. Stevens, Esq.; Beyer Weaver & Thomas, LLP

(57) ABSTRACT

Described herein are methods of producing kinesins. In a preferred embodiment, the kinesins are produced from a prokaryote, most preferably, a bacterial cell. Bacterial expression offers several advantages over systems previously utilized, such as, for example, Bacculovirus. The yield of protein is higher, the cost of the expression setup is lower, and creation of alternative expression vectors is easier. The concern of copurifying a contaminating activity from the expression host is also eliminated since bacteria, in contrast to the bacculovirus expression system, do not have kinesin like proteins. Also described herein are purified kinesins, preferably unglycosylated and methods of use.

24 Claims, No Drawings

SEQUENCE LISTING

```
<160> NUMBER OF SEQ ID NOS: 105

<210> SEQ ID NO 1
<211> LENGTH: 29
<212> TYPE: DNA
<213> ORGANISM: Artificial Sequence
<220> FEATURE:
<223> OTHER INFORMATION: 3' primer for amplification of chromokinesin
      (residues 1-193)

<400> SEQUENCE: 1

ccaaacagga aacagtatcc aaggcaacc                                      29


<210> SEQ ID NO 2
<211> LENGTH: 20
<212> TYPE: DNA
<213> ORGANISM: Artificial Sequence
<220> FEATURE:
<223> OTHER INFORMATION: Chromokinesin 5' primer (spanning nucleotides
      76-1178)

<400> SEQUENCE: 2

tgcccatctc gtgagaaagc                                                20


<210> SEQ ID NO 3
<211> LENGTH: 20
<212> TYPE: DNA
<213> ORGANISM: Artificial Sequence
<220> FEATURE:
```

-continued

```
<223> OTHER INFORMATION: Chromokinesin 3' primer (spanning 76-1178)

<400> SEQUENCE: 3

gcttgacgga gagcatgctg                                                20


<210> SEQ ID NO 4
<211> LENGTH: 20
<212> TYPE: DNA
<213> ORGANISM: Artificial Sequence
<220> FEATURE:
<223> OTHER INFORMATION: Chromokinesin 5' primer

<400> SEQUENCE: 4

attgattacc cagttatcgg                                                20


<210> SEQ ID NO 5
<211> LENGTH: 20
<212> TYPE: DNA
<213> ORGANISM: Artificial Sequence
<220> FEATURE:
<223> OTHER INFORMATION: Chromokinesin 3' primer

<400> SEQUENCE: 5

tgatgactcc aacttcagtg                                                20


<210> SEQ ID NO 6
<211> LENGTH: 25
<212> TYPE: DNA
<213> ORGANISM: Artificial Sequence
<220> FEATURE:
<223> OTHER INFORMATION: Kin-2 5' primer

<400> SEQUENCE: 6

gccgaataca tcaagcaatg gtaac                                          25


<210> SEQ ID NO 7
<211> LENGTH: 25
<212> TYPE: DNA
<213> ORGANISM: Artificial Sequence
<220> FEATURE:
<223> OTHER INFORMATION: Kin-2 3' primer

<400> SEQUENCE: 7

tctgggtatc ctttagcagc aaatg                                          25


<210> SEQ ID NO 8
<211> LENGTH: 25
<212> TYPE: DNA
<213> ORGANISM: Artificial Sequence
<220> FEATURE:
<223> OTHER INFORMATION: MKLP1 5' primer

<400> SEQUENCE: 8

agccatgttg tcagcgagag ctaag                                          25


<210> SEQ ID NO 9
<211> LENGTH: 28
<212> TYPE: DNA
<213> ORGANISM: Artificial Sequence
<220> FEATURE:
<223> OTHER INFORMATION: MKLP1 3' primer

<400> SEQUENCE: 9

agggtctctc tggcttctca gttttagg                                       28
```

<210> SEQ ID NO 10
<211> LENGTH: 25
<212> TYPE: DNA
<213> ORGANISM: Artificial Sequence
<220> FEATURE:
<223> OTHER INFORMATION: KSP 5' primer

<400> SEQUENCE: 10
ccttgatttt ttggcgggga ccgtc 25

<210> SEQ ID NO 11
<211> LENGTH: 25
<212> TYPE: DNA
<213> ORGANISM: Artificial Sequence
<220> FEATURE:
<223> OTHER INFORMATION: KSP 3' primer

<400> SEQUENCE: 11
aaaggttgat ctgggctcgc agagg 25

<210> SEQ ID NO 12
<211> LENGTH: 25
<212> TYPE: DNA
<213> ORGANISM: Artificial Sequence
<220> FEATURE:
<223> OTHER INFORMATION: MCAK 5' primer

<400> SEQUENCE: 12
gcgtttctct tccttgctga ctctc 25

<210> SEQ ID NO 13
<211> LENGTH: 25
<212> TYPE: DNA
<213> ORGANISM: Artificial Sequence
<220> FEATURE:
<223> OTHER INFORMATION: MCAK 3' primer

<400> SEQUENCE: 13
agaggctggg tgtcaaacca aacag 25

<210> SEQ ID NO 14
<211> LENGTH: 20
<212> TYPE: DNA
<213> ORGANISM: Artificial Sequence
<220> FEATURE:
<223> OTHER INFORMATION: Kid 5' primer

<400> SEQUENCE: 14
gtcgctgtcg gctaagcaag 20

<210> SEQ ID NO 15
<211> LENGTH: 20
<212> TYPE: DNA
<213> ORGANISM: Artificial Sequence
<220> FEATURE:
<223> OTHER INFORMATION: Kid 3' primer

<400> SEQUENCE: 15
ctttgcccct gtgactgtgc 20

<210> SEQ ID NO 16
<211> LENGTH: 31
<212> TYPE: DNA
<213> ORGANISM: Artificial Sequence
<220> FEATURE:
<223> OTHER INFORMATION: Kid 5' primer

<400> SEQUENCE: 16
ctggatccca gccgcgggcg gctcgacgca g 31

<210> SEQ ID NO 17
<211> LENGTH: 26
<212> TYPE: DNA
<213> ORGANISM: Artificial Sequence
<220> FEATURE:
<223> OTHER INFORMATION: Kid 3' primer

<400> SEQUENCE: 17
ctctagagag cagctgtcca tgcccc 26

<210> SEQ ID NO 18
<211> LENGTH: 20
<212> TYPE: DNA
<213> ORGANISM: Artificial Sequence
<220> FEATURE:
<223> OTHER INFORMATION: HSET 5' primer

<400> SEQUENCE: 18
gggcttggtg caagagcttc 20

<210> SEQ ID NO 19
<211> LENGTH: 23
<212> TYPE: DNA
<213> ORGANISM: Artificial Sequence
<220> FEATURE:
<223> OTHER INFORMATION: HSET 3' primer

<400> SEQUENCE: 19 caccctcac ccgatacata gac 23

<210> SEQ ID NO 20
<211> LENGTH: 20
<212> TYPE: DNA
<213> ORGANISM: Artificial Sequence
<220> FEATURE:
<223> OTHER INFORMATION: ATSV 5' primer

<400> SEQUENCE: 20
gggctcccac tactgcgagg 20

<210> SEQ ID NO 21
<211> LENGTH: 20
<212> TYPE: DNA
<213> ORGANISM: Artificial Sequence
<220> FEATURE:
<223> OTHER INFORMATION: ATSV 3' primer

<400> SEQUENCE: 21
ctcctcctcg ttcacctccg 20

<210> SEQ ID NO 22
<211> LENGTH: 4348
<212> TYPE: DNA
<213> ORGANISM: Human

<400> SEQUENCE: 22
gggaggccca gggagaacgg ggaagggaca tttagtttga gacggtgctg agataggatc 60
atgaaggaag aggtgaaggg aattcctgta agagtggcgc tgcgttgtcg ccctctggtc 120
cccaaagaga ttagcgaggg ctgccagatg tgcctttcct tcgtgcccgg agagcctcag 180
gtggtggttg gtacagataa atccttcacc tacgattttg tatttgatcc ctctactgaa 240

-continued

```
caggaagaag tcttcaatac agcagtagcg ccactcataa aaggtgtatt taaaggatat    300
aatgcaacgg tcctggccta tgggcagact ggctctggaa aaacctattc aatgggaggt    360
gcatatactg cagagcaaga gaatgaacca acagttgggg ttattcctag ggtaatacaa    420
ctgctcttca aagaaattga taaaaagagt gactttgaat ttactctgaa agtgtcttac    480
ttagagattt acaatgaaga aattttggat cttctatgtc catctcgtga gaaagctcaa    540
ataaatatac gagaggatcc taaggaaggc ataaagattg tgggactcac tgagaagact    600
gttttggttg ccttggatac tgtttcctgt ttggaacagg gcaacaactc taggactgtg    660
gcctccacgg ctatgaactc ccagtcgtcc cgatctcatg ccatctttac aatctcctta    720
gagcaaggaa agaaaagtga caagaatagc agctttcgct ccaagctgca tcttgtagac    780
ctcgctggat cagaaagaca gaagaaaacc aaggctgaag gggatcgtct aaaagagggt    840
attaatatta accgaggcct cctatgcttg ggaaatgtaa tcagtgctct tggagatgac    900
aaaaagggtg gctttgcgcc ctacagagat tccaagttga ctcgactgct tcaagattct    960
ctaggaggta atagccatac tcttatgata gcctgtgtga gtcctgctga ctccaatcta   1020
gaggaaacat taaataccct tcgctatgct gacagagcaa gaaaaatcaa gaacaaacct   1080
attgttaata ttgatcccca gacagctgaa cttaatcatc taaagcaaca ggtacaacag   1140
ctacaagtct tgttgctaca ggcccatgga ggtaccctgc ctggatctat aactgtggaa   1200
ccatcagaga atctacaatc cctgatggag aagaatcagt ccctggtaga ggagaatgaa   1260
aaattaagtc gtggtctgag cgaggcagct ggtcagacag cccagatgtt ggagaggatc   1320
atttggacag agcaagcgaa tgaaaaaatg aacgccaagc tagaagagct caggcagcat   1380
gcggcctgca aactggatct tcaaaagcta gtggagactt tggaagacca ggaattgaaa   1440
gaaaatgtag agataatttg taacctgcag caattgatta cccagttatc ggatgaaact   1500
gttgcttgca tggctgcagc cattgatact gcggtggagc aagaagccca agtagaaacc   1560
agtccagaga cgagcaggtc ttctgacgct tttaccactc agcatgctct ccgtcaagcg   1620
cagatgtcta aggagctggt tgagttgaat aaagcgcttg cactgaaaga ggccctggct   1680
aggaagatga ctcagaatga cagccaactg cagcctattc agtaccaata ccaggataac   1740
ataaaagagc cagaattaga agtcatcaat ctgcaaaagg aaaaggaaga attggttctt   1800
gaacttcaga cagcaaagaa ggatgccaac caagccaagt tgagtgagcg ccgccgcaaa   1860
cgtctccagg agctggaggg tcaaattgct gatctgaaga agaaactgaa tgagcagtcc   1920
aaacttctga aactaaagga atccacagag cgtactgtct ccaaactgaa ccaggagata   1980
cggatgatga aaaaccagcg ggtacagtta atgcgtcaaa tgaaagaaga tgctgagaag   2040
tttagacagt ggaagcagaa aagagacaaa gaagtaatac agttaaaaga acgagaccgt   2100
aagaggcaat atgagctgct gaaacttgaa agaaacttcc agaaacaatc caatgtgctc   2160
agacgtaaaa cggaggaggc agcagctgcc aacaagcgtc tcaaggatgc tctccagaaa   2220
caacgggagg ttgcagataa gcggaaagag actcagagcc gtggaatgga aggcactgca   2280
gctcgagtga agaattggct tggaaacgaa attgaggtta tggtcagtac tgaggaagcc   2340
aaacgccatc tgaatgacct ccttgaagat agaaagatcc tggctcaaga tgtggctcaa   2400
ctcaaagaaa aaaaggaatc tggggagaat ccacctccta aactccggag gcgtacattc   2460
tcccttactg aagtgcgtgg tcaagtttcg gagtcagaag attctattac aaagcagatt   2520
gaaagcctag agactgaaat ggaattcagg agtgctcaga ttgctgacct acagcagaag   2580
```

-continued

```
ctgctggatg cagaaagtga agacagacca aaacaacgct gggagaatat tgccaccatt   2640

ctggaagcca agtgtgccct gaaatatttg attggagagc tggtctcctc caaaatacag   2700

gtcagcaaac ttgaaagcag cctgaaacag agcaagacca gctgtgctga catgcagaag   2760

atgctgtttg aggaacgaaa tcattttgcc gagatagaga cagagttaca agctgagctg   2820

gtcagaatgg agcaacagca ccaagagaag gtgctgtacc ttctcagcca gctgcagcaa   2880

agccaaatgg cagagaagca gttagaggaa tcagtcagtg aaaaggaaca gcagctgctg   2940

agcacactga agtgtcagga tgaagaactt gagaaaatgc gagaagtgtg tgagcaaaat   3000

cagcagcttc tccgagagaa tgaaatcatc aagcagaaac tgaccctcct ccaggtagcc   3060

agcagacaga aacatcttcc taaggatacc cttctatctc cagactcttc ttttgaatat   3120

gtccagccta agccaaaacc ttctcgtgtt aaagaaaagt tcctggagca aagcatggac   3180

atcgaggatc taaaatattg ttcagagcat tctgtgaatg agcatgagga tggtgatggt   3240

gatgatgatg agggggatga cgaggaatgg aagccaacaa aattagttaa tgtgtccagg   3300

aagaacatcc aagggtgttc ctgcaagggc tggtgtggaa acaagcaatg tgggtgcagg   3360

aagcaaaagt cagactgtgg tgtggactgt tgctgtgacc ccacaaagtg tcggaaccgc   3420

cagcaaggca aggatagctt gggcactgtt gaacggaccc aggattcaga aagctccttc   3480

aaactggagg atcctaccga ggtgacccca ggattgagct tctttaatcc cgtctgtgcc   3540

acccccaata gcaagatcct gaaagagatg tgcgatgtgg agcaggtgct gtcaaagaag   3600

actcccccag ctccctcccc ttttgacctc ccagagttga aacatgtagc aacagaatac   3660

caagaaaaca aggctccagg gaagaaaaag aaacgggctc tggccagcaa caccagcttc   3720

ttctctggct gctcccctat cgaagaagag gcccactgaa gttggagtca tcatctctac   3780

ccccagtctg gcttgggaga tgctttcagg ttgcagccag aaggggtttt ttaaatgact   3840

tctctggatt tcaggtttct tgctgttgaa aaaaggaaca aagcgttact gaaaagaagg   3900

taacctttgt tggatgtggg ccttagcctc caggtccaga ctactactct atgttctcca   3960

gaagggtgct aagtcaccta ctgaagagag aaccaactga ctttcctatt gactcatcag   4020

gaaccagtcc tcagtctggt caagttgttt cttatttgtg agcagttcag gctatctcct   4080

gatggggatg aggccaaggc tttcttatct tttggttgtc tctgcttaat ggaggagcct   4140

ggcctaggat ggaggcctgg cttagatctt tcattccacc tcaggaatga ggttgtgatc   4200

tttcctgtcc tgaccctctc tgaattatgt ttcaatagta ctcttgattg tctgccatgt   4260

tgttgaagca aatgaattat ttttaaatgt taagtaagta aataaacctt agcccgtctt   4320

tttttttttt tttttttttt tttttttt                                      4348


<210> SEQ ID NO 23
<211> LENGTH: 1231
<212> TYPE: PRT
<213> ORGANISM: Human

<400> SEQUENCE: 23

Met Lys Glu Glu Val Lys Gly Ile Pro Val Arg Val Ala Leu Arg Cys
 1               5                  10                  15

Arg Pro Leu Val Pro Lys Glu Ile Ser Glu Gly Cys Gln Met Cys Leu
            20                  25                  30

Ser Phe Val Pro Gly Glu Pro Gln Val Val Val Gly Thr Asp Lys Ser
        35                  40                  45

Phe Thr Tyr Asp Phe Val Phe Asp Pro Ser Thr Glu Gln Glu Glu Val
    50                  55                  60
```

-continued

```
Phe Asn Thr Ala Val Ala Pro Leu Ile Lys Gly Val Phe Lys Gly Tyr
65                  70                  75                  80

Asn Ala Thr Val Leu Ala Tyr Gly Gln Thr Gly Ser Gly Lys Thr Tyr
                85                  90                  95

Ser Met Gly Gly Ala Tyr Thr Ala Glu Gln Glu Asn Glu Pro Thr Val
            100                 105                 110

Gly Val Ile Pro Arg Val Ile Gln Leu Leu Phe Lys Glu Ile Asp Lys
        115                 120                 125

Lys Ser Asp Phe Glu Phe Thr Leu Lys Val Ser Tyr Leu Glu Ile Tyr
    130                 135                 140

Asn Glu Glu Ile Leu Asp Leu Leu Cys Pro Ser Arg Glu Lys Ala Gln
145                 150                 155                 160

Ile Asn Ile Arg Glu Asp Pro Lys Glu Gly Ile Lys Ile Val Gly Leu
                165                 170                 175

Thr Glu Lys Thr Val Leu Val Ala Leu Asp Thr Val Ser Cys Leu Glu
            180                 185                 190

Gln Gly Asn Asn Ser Arg Thr Val Ala Ser Thr Ala Met Asn Ser Gln
        195                 200                 205

Ser Ser Arg Ser His Ala Ile Phe Thr Ile Ser Leu Glu Gln Gly Lys
    210                 215                 220

Lys Ser Asp Lys Asn Ser Ser Phe Arg Ser Lys Leu His Leu Val Asp
225                 230                 235                 240

Leu Ala Gly Ser Glu Arg Gln Lys Lys Thr Lys Ala Glu Gly Asp Arg
                245                 250                 255

Leu Lys Glu Gly Ile Asn Ile Asn Arg Gly Leu Leu Cys Leu Gly Asn
            260                 265                 270

Val Ile Ser Ala Leu Gly Asp Asp Lys Lys Gly Gly Phe Ala Pro Tyr
        275                 280                 285

Arg Asp Ser Lys Leu Thr Arg Leu Leu Gln Asp Ser Leu Gly Gly Asn
    290                 295                 300

Ser His Thr Leu Met Ile Ala Cys Val Ser Pro Ala Asp Ser Asn Leu
305                 310                 315                 320

Glu Glu Thr Leu Asn Thr Leu Arg Tyr Ala Asp Arg Ala Arg Lys Ile
                325                 330                 335

Lys Asn Lys Pro Ile Val Asn Ile Asp Pro Gln Thr Ala Glu Leu Asn
            340                 345                 350

His Leu Lys Gln Gln Val Gln Gln Leu Gln Val Leu Leu Leu Gln Ala
        355                 360                 365

His Gly Gly Thr Leu Pro Gly Ser Ile Thr Val Glu Pro Ser Glu Asn
    370                 375                 380

Leu Gln Ser Leu Met Glu Lys Asn Gln Ser Leu Val Glu Glu Asn Glu
385                 390                 395                 400

Lys Leu Ser Arg Gly Leu Ser Glu Ala Ala Gly Gln Thr Ala Gln Met
                405                 410                 415

Leu Glu Arg Ile Ile Trp Thr Glu Gln Ala Asn Glu Lys Met Asn Ala
            420                 425                 430

Lys Leu Glu Glu Leu Arg Gln His Ala Ala Cys Lys Leu Asp Leu Gln
        435                 440                 445

Lys Leu Val Glu Thr Leu Asp Gln Glu Leu Lys Glu Asn Val Glu Ile
    450                 455                 460

Ile Cys Asn Leu Gln Gln Leu Ile Thr Gln Leu Ser Asp Glu Thr Val
465                 470                 475                 480
```

-continued

```
Ala Cys Met Ala Ala Ala Ile Asp Thr Ala Val Glu Gln Glu Ala Gln
                485                 490                 495

Val Glu Thr Ser Pro Glu Thr Ser Arg Ser Ser Asp Ala Phe Thr Thr
            500                 505                 510

Gln His Ala Leu Arg Gln Ala Gln Met Ser Lys Glu Leu Val Glu Leu
        515                 520                 525

Asn Lys Ala Leu Ala Leu Lys Glu Ala Leu Ala Arg Lys Met Thr Gln
    530                 535                 540

Asn Asp Ser Gln Leu Gln Pro Ile Gln Tyr Gln Tyr Gln Asp Asn Ile
545                 550                 555                 560

Lys Glu Pro Glu Leu Glu Val Ile Asn Leu Gln Lys Glu Lys Glu Glu
                565                 570                 575

Leu Val Leu Glu Leu Gln Thr Ala Lys Lys Asp Ala Asn Gln Ala Lys
            580                 585                 590

Leu Ser Glu Arg Arg Arg Lys Arg Leu Gln Glu Leu Glu Gly Gln Ile
        595                 600                 605

Ala Asp Leu Lys Lys Lys Leu Asn Glu Gln Ser Lys Leu Leu Lys Leu
    610                 615                 620

Lys Glu Ser Thr Glu Arg Thr Val Ser Lys Leu Asn Gln Glu Ile Arg
625                 630                 635                 640

Met Met Lys Asn Gln Arg Val Gln Leu Met Arg Gln Met Lys Glu Asp
                645                 650                 655

Ala Glu Lys Phe Arg Gln Trp Lys Gln Lys Arg Asp Lys Glu Val Ile
            660                 665                 670

Gln Leu Lys Glu Arg Asp Arg Lys Arg Gln Tyr Glu Leu Leu Lys Leu
        675                 680                 685

Glu Arg Asn Phe Gln Lys Gln Ser Asn Val Leu Arg Arg Lys Thr Glu
    690                 695                 700

Glu Ala Ala Ala Ala Asn Lys Arg Leu Lys Asp Ala Leu Gln Lys Gln
705                 710                 715                 720

Arg Glu Val Ala Asp Lys Arg Lys Glu Thr Gln Ser Arg Gly Met Glu
                725                 730                 735

Gly Thr Ala Ala Arg Val Lys Asn Trp Leu Gly Asn Glu Ile Glu Val
            740                 745                 750

Met Val Ser Thr Glu Glu Ala Lys Arg His Leu Asn Asp Leu Leu Glu
        755                 760                 765

Asp Arg Lys Ile Leu Ala Gln Asp Val Ala Gln Leu Lys Glu Lys Lys
    770                 775                 780

Glu Ser Gly Glu Asn Pro Pro Pro Lys Leu Arg Arg Arg Thr Phe Ser
785                 790                 795                 800

Leu Thr Glu Val Arg Gly Gln Val Ser Glu Ser Glu Asp Ser Ile Thr
                805                 810                 815

Lys Gln Ile Glu Ser Leu Glu Thr Glu Met Glu Phe Arg Ser Ala Gln
            820                 825                 830

Ile Ala Asp Leu Gln Gln Lys Leu Leu Asp Ala Glu Ser Glu Asp Arg
        835                 840                 845

Pro Lys Gln Arg Trp Glu Asn Ile Ala Thr Ile Leu Glu Ala Lys Cys
    850                 855                 860

Ala Leu Lys Tyr Leu Ile Gly Glu Leu Val Ser Ser Lys Ile Gln Val
865                 870                 875                 880

Ser Lys Leu Glu Ser Ser Leu Lys Gln Ser Lys Thr Ser Cys Ala Asp
                885                 890                 895

Met Gln Lys Met Leu Phe Glu Glu Arg Asn His Phe Ala Glu Ile Glu
```

-continued

```
        900                 905                 910

Thr Glu Leu Gln Ala Glu Leu Val Arg Met Glu Gln Gln His Gln Glu
        915                 920                 925

Lys Val Leu Tyr Leu Leu Ser Gln Leu Gln Gln Ser Gln Met Ala Glu
    930                 935                 940

Lys Gln Leu Glu Glu Ser Val Ser Glu Lys Glu Gln Gln Leu Leu Ser
945                 950                 955                 960

Thr Leu Lys Cys Gln Asp Glu Glu Leu Glu Lys Met Arg Glu Val Cys
                965                 970                 975

Glu Gln Asn Gln Gln Leu Leu Arg Glu Asn Glu Ile Ile Lys Gln Lys
            980                 985                 990

Leu Thr Leu Leu Gln Val Ala Ser Arg Gln Lys His Leu Pro Lys Asp
        995                 1000                1005

Thr Leu Leu Ser Pro Asp Ser Ser Phe Glu Tyr Val Gln Pro Lys Pro
    1010                1015                1020

Lys Pro Ser Arg Val Lys Glu Lys Phe Leu Glu Gln Ser Met Asp Ile
1025                1030                1035                1040

Glu Asp Leu Lys Tyr Cys Ser Glu His Ser Val Asn Glu His Glu Asp
                1045                1050                1055

Gly Asp Gly Asp Asp Asp Glu Gly Asp Asp Glu Glu Trp Lys Pro Thr
            1060                1065                1070

Lys Leu Val Asn Val Ser Arg Lys Asn Ile Gln Gly Cys Ser Cys Lys
        1075                1080                1085

Gly Trp Cys Gly Asn Lys Gln Cys Gly Cys Arg Lys Gln Lys Ser Asp
    1090                1095                1100

Cys Gly Val Asp Cys Cys Cys Asp Pro Thr Lys Cys Arg Asn Arg Gln
1105                1110                1115                1120

Gln Gly Lys Asp Ser Leu Gly Thr Val Glu Arg Thr Gln Asp Ser Glu
                1125                1130                1135

Ser Ser Phe Lys Leu Glu Asp Pro Thr Glu Val Thr Pro Gly Leu Ser
            1140                1145                1150

Phe Phe Asn Pro Val Cys Ala Thr Pro Asn Ser Lys Ile Leu Lys Glu
        1155                1160                1165

Met Cys Asp Val Glu Gln Val Leu Ser Lys Lys Thr Pro Pro Ala Pro
    1170                1175                1180

Ser Pro Phe Asp Leu Pro Glu Leu Lys His Val Ala Thr Glu Tyr Gln
1185                1190                1195                1200

Glu Asn Lys Ala Pro Gly Lys Lys Lys Lys Arg Ala Leu Ala Ser Asn
                1205                1210                1215

Thr Ser Phe Phe Ser Gly Cys Ser Pro Ile Glu Glu Glu Ala His
            1220                1225                1230


<210> SEQ ID NO 24
<211> LENGTH: 2905
<212> TYPE: DNA
<213> ORGANISM: Human

<400> SEQUENCE: 24

ggccgaatac atcaagcaat ggtaacatct ttaaatgaag ataatgaaag tgtaactgtt      60

gaatggatag aaaatggaga tacaaaaggc aaagagattg acctggagag catcttttca     120

cttaaccctg accttgttcc tgatgaagaa attgaaccca gtccagaaac acctccacct     180

ccagcatcct cagccaaagt aaacaaaatt gtaaagaatc gacggactgt agcttctatt     240

aagaatgacc ctccttcaag agataataga gtggttggtt cagcacgtgc acggcccagt     300
```

-continued

```
caatttcctg aacagtcttc ctctgcacaa cagaatggta gtgtttcaga tatatctcca    360
gttcaagctg caaaaaagga atttggaccc ccttcacgta gaaaatctaa ttgtgtgaaa    420
gaagtagaaa aactgcaaga aaaacgagag aaaaggagat tgcaacagca agaacttaga    480
gaaaaaagag cccaggacgt tgatgctaca aacccaaatt atgaaattat gtgtatgatc    540
agagacttta gaggaagttt ggattataga ccattaacaa cagcagatcc tattgatgaa    600
cataggatat gtgtgtgtgt aagaaaacga ccactcaata aaaaagaaac tcaaatgaaa    660
gatcttgatg taatcacaat tcctagtaaa gatgttgtga tggtacatga accaaaacaa    720
aaagtagatt taacaaggta cctagaaaac caaacatttc gttttgatta tgcctttgat    780
gactcagctc ctaatgaaat ggtttacagg tttactgcta aaccactagt ggaaactata    840
tttgaaaggg gaatggctac atgctttgct tatgggcaga ctggaagtgg aaaaactcat    900
actatgggtg gtgacttttc aggaaagaac caagattgtt ctaaaggaat ttatgcatta    960
gcagctcgag atgtcttttt aatgctaaag aagccaaact ataagaagct agaacttcaa   1020
gtatatgcaa ccttctttga aatttatagt ggaaaggtgt ttgacttgct aaacaggaaa   1080
acaaaattaa gagttctaga agatggaaaa cagcaggttc aagtggtggg attacaggaa   1140
cgggaggtca aatgtgttga agatgtactg aaactcattg acataggcaa cagttgcaga   1200
acatccggtc aaacatctgc aaatgcacat tcatctcgga gccatgcagt gtttcagatt   1260
attcttagaa ggaaaggaaa actacatggc aaattttctc tcattgattt ggctggaaat   1320
gaaagaggag ctgatacttc cagtgcggac aggcaaacta ggcttgaagg tgctgaaatt   1380
aataaaagcc ttttagcact caaggagtgc atcagagcct taggtagaaa taaacctcat   1440
actcctttcc gtgcaagtaa actcactcag gtgttaagag attctttcat aggtgaaaac   1500
tctcgtacct gcatgattgc cacaatctct ccaggaatgg catcctgtga aaatactctt   1560
aatacattaa gatatgcaaa tagggtcaaa gaattgactg tagatccaac tgctgctggt   1620
gatgttcgtc caataatgca ccatccacca aaccagattg atgacttaga gacacagtgg   1680
ggtgtgggga gttcccctca gagagatgat ctaaaacttc tttgtgaaca aaatgaagaa   1740
gaagtctctc cacagttgtt tactttccac gaagctgttt cacaaatggt agaaatggaa   1800
gaacaagttg tagaagatca cagggcagtg ttccaggaat ctattcggtg gttagaagat   1860
gaaaaggccc tcttagagat gactgaagaa gtagattatg atgtcgattc atatgctaca   1920
caacttgaag ctattcttga gcaaaaaata gacattttaa ctgaactgcg ggataaagtg   1980
aaatctttcc gtgcagctct acaagaggag gaacaagcca gcaagcaaat caacccgaag   2040
agaccccgtg ccctttaaac cggcatttgc tgctaaagga tacccagaac cctcactact   2100
gtaacataca acggttcagc tgtaagggcc atttgaaagt ttggaatttt aagtgtctgt   2160
ggaaaatgtt ttgtccttca cctgaattac atttcaattt tgtgaaacac tcttttgtct   2220
acaaaatgct tctagtccag gaggcacaac caagaactgg gattaatgaa gcattttgtt   2280
tcatttacac aaatagtgat ttacttttgg agatccttgt cagttttatt ttctatttga   2340
tgaagtaaga ctgtggactc aatccagagc cagatagtag gggaagccac agcatttcct   2400
tttaactcag ttcaattttt gtagtgagac tgagcagttt taaatccttt gcgtgcatgc   2460
atacctcatc agtgattgta catacttgc ccactcctag agacagctgt gctcactttt    2520
cctgctttgt gccttgatta aggctactga ccctaaattt ctgaagcaca gccaagaaaa   2580
attacattcc ttgtcattgt aaattacctt tgtgtgtaca tttttactgt atttgagaca   2640
```

-continued

```
tttttgtgt gtgactagtt aattttgcag gatgtgccat atcattgaac ggaactaaag   2700

tctgtgacag tggatatagc tgctggacca ttccatctta tatgtaaaga aatctggaat   2760

tattatttta aaaccatata acatgtgatt ataatttttc ttagcatttt ctttgtaaag   2820

aactacaata taaactagtt ggtgtataat aaaaagtaat gaaattctga agaaaaaaaa   2880

aaaaaaaaaa aaaaaaaaaa aaaaa                                         2905


<210> SEQ ID NO 25
<211> LENGTH: 678
<212> TYPE: PRT
<213> ORGANISM: Human

<400> SEQUENCE: 25

Met Val Thr Ser Leu Asn Glu Asp Asn Glu Ser Val Thr Val Glu Trp
 1               5                  10                  15

Ile Glu Asn Gly Asp Thr Lys Gly Lys Glu Ile Asp Leu Glu Ser Ile
            20                  25                  30

Phe Ser Leu Asn Pro Asp Leu Val Pro Asp Glu Glu Ile Glu Pro Ser
        35                  40                  45

Pro Glu Thr Pro Pro Pro Pro Ala Ser Ser Ala Lys Val Asn Lys Ile
    50                  55                  60

Val Lys Asn Arg Arg Thr Val Ala Ser Ile Lys Asn Asp Pro Pro Ser
65                  70                  75                  80

Arg Asp Asn Arg Val Val Gly Ser Ala Arg Ala Arg Pro Ser Gln Phe
                85                  90                  95

Pro Glu Gln Ser Ser Ser Ala Gln Gln Asn Gly Ser Val Ser Asp Ile
            100                 105                 110

Ser Pro Val Gln Ala Ala Lys Lys Glu Phe Gly Pro Pro Ser Arg Arg
        115                 120                 125

Lys Ser Asn Cys Val Lys Glu Val Glu Lys Leu Gln Glu Lys Arg Glu
    130                 135                 140

Lys Arg Arg Leu Gln Gln Gln Glu Leu Arg Glu Lys Arg Ala Gln Asp
145                 150                 155                 160

Val Asp Ala Thr Asn Pro Asn Tyr Glu Ile Met Cys Met Ile Arg Asp
                165                 170                 175

Phe Arg Gly Ser Leu Asp Tyr Arg Pro Leu Thr Thr Ala Asp Pro Ile
            180                 185                 190

Asp Glu His Arg Ile Cys Val Cys Val Arg Lys Arg Pro Leu Asn Lys
        195                 200                 205

Lys Glu Thr Gln Met Lys Asp Leu Asp Val Ile Thr Ile Pro Ser Lys
    210                 215                 220

Asp Val Val Met Val His Glu Pro Lys Gln Lys Val Asp Leu Thr Arg
225                 230                 235                 240

Tyr Leu Glu Asn Gln Thr Phe Arg Phe Asp Tyr Ala Phe Asp Asp Ser
                245                 250                 255

Ala Pro Asn Glu Met Val Tyr Arg Phe Thr Ala Lys Pro Leu Val Glu
            260                 265                 270

Thr Ile Phe Glu Arg Gly Met Ala Thr Cys Phe Ala Tyr Gly Gln Thr
        275                 280                 285

Gly Ser Gly Lys Thr His Thr Met Gly Gly Asp Phe Ser Gly Lys Asn
    290                 295                 300

Gln Asp Cys Ser Lys Gly Ile Tyr Ala Leu Ala Ala Arg Asp Val Phe
305                 310                 315                 320

Leu Met Leu Lys Lys Pro Asn Tyr Lys Lys Leu Glu Leu Gln Val Tyr
```

-continued

```
                325                 330                 335

Ala Thr Phe Phe Glu Ile Tyr Ser Gly Lys Val Phe Asp Leu Leu Asn
            340                 345                 350

Arg Lys Thr Lys Leu Arg Val Leu Glu Asp Gly Lys Gln Gln Val Gln
        355                 360                 365

Val Val Gly Leu Gln Glu Arg Glu Val Lys Cys Val Glu Asp Val Leu
    370                 375                 380

Lys Leu Ile Asp Ile Asn Ser Cys Arg Thr Ser Gly Gln Thr Ser Ala
385                 390                 395                 400

Asn Ala His Ser Ser Arg Ser His Ala Val Phe Gln Ile Ile Leu Arg
                405                 410                 415

Arg Lys Gly Lys Leu His Gly Lys Phe Ser Leu Ile Asp Leu Ala Gly
            420                 425                 430

Asn Glu Arg Gly Ala Asp Thr Ser Ser Ala Asp Arg Gln Thr Arg Leu
        435                 440                 445

Glu Gly Ala Glu Ile Asn Lys Ser Leu Leu Ala Leu Lys Glu Cys Ile
    450                 455                 460

Arg Ala Leu Gly Arg Asn Lys Pro His Thr Pro Phe Arg Ala Ser Lys
465                 470                 475                 480

Leu Thr Gln Val Leu Arg Asp Ser Phe Ile Gly Glu Asn Ser Arg Thr
                485                 490                 495

Cys Met Ile Ala Thr Ile Ser Pro Gly Met Ala Ser Cys Glu Asn Thr
            500                 505                 510

Leu Asn Thr Leu Arg Tyr Ala Asn Arg Val Lys Glu Leu Thr Val Asp
        515                 520                 525

Pro Thr Ala Ala Gly Asp Val Arg Pro Ile Met His His Pro Pro Asn
    530                 535                 540

Gln Ile Asp Asp Leu Glu Thr Gln Trp Gly Val Gly Ser Ser Pro Gln
545                 550                 555                 560

Arg Asp Asp Leu Lys Leu Leu Cys Glu Gln Asn Glu Glu Glu Val Ser
                565                 570                 575

Pro Gln Leu Phe Thr Phe His Glu Ala Val Ser Gln Met Val Glu Met
            580                 585                 590

Glu Glu Gln Val Val Glu Asp His Arg Ala Val Phe Gln Glu Ser Ile
        595                 600                 605

Arg Trp Leu Glu Asp Glu Lys Ala Leu Leu Glu Met Thr Glu Glu Val
    610                 615                 620

Asp Tyr Asp Val Asp Ser Tyr Ala Thr Gln Leu Glu Ala Ile Leu Glu
625                 630                 635                 640

Gln Lys Ile Asp Ile Leu Thr Glu Leu Arg Asp Lys Val Lys Ser Phe
                645                 650                 655

Arg Ala Ala Leu Gln Glu Glu Glu Gln Ala Ser Lys Gln Ile Asn Pro
            660                 665                 670

Lys Arg Pro Arg Ala Leu
        675


<210> SEQ ID NO 26
<211> LENGTH: 3258
<212> TYPE: DNA
<213> ORGANISM: Human

<400> SEQUENCE: 26

ttcgtgatgg attcagtact cctcaaccac tcttcctaat gattggaaca aaagaaaaaa      60

aaaagaaaaa aaagccatgt tgtcagcgag agctaagaca ccccggaaac ctaccgtgaa     120
```

-continued

```
aaagggtccc aaacgaacct taaagaccca gttgggatac tgtagggtgc gactgggctt    180
tcctgatcaa gagtgttgca tagaagtgat caataataca actgttcagc ttcatactcc    240
tgagggctac agactcaacc gaaatggaga ctataaggag actcagtatt catttaaaca    300
agtatttggc actcacacca cccagaagga actctttgat gttgtggcta atcccttggt    360
caatgacctc attcatggca aaaatggtct tctttttaca tatggtgtga cgggaagtgg    420
aaaaactcac acaatgactg gttctccagg ggaaggaggg ctgcttcctc gttgtttgga    480
catgatcttt aacagtatag ggtcatttca agctaaacga tatgttttca aatctaatga    540
taggaatagt atggatatac agtgtgaggt tgatgcctta ttagaacgtc agaaaagaga    600
agctatgccc aatccaaaga cttcttctag caaacgacaa gtagatccag agtttgcaga    660
tatgataact gtacaagaat tctgcaaagc agaagaggtt gatgaagata gtgtctatgg    720
tgtatttgtc tcttatattg aaatatataa taattacata tatgatctat tggaagaggt    780
gccgtttgat cccataaacc caaacctcca caatctaaat tgcttcgtga agattaagaa    840
ccataacatg tatgttgcag gatgtacaga agttgaagtg aaatctactg aggaggcttt    900
tgaagttttc tggagaggcc agaaaaagag acgtattgct aatacccatt tgaatcgtga    960
gtccagccgt tcccatagcg tgttcaacat taaattagtt caggctccct tggatgcaga   1020
tggagacaat gtcttacagg aaaaagaaca aatcactata agtcagttgt ccttggtaga   1080
tcttgctgga agtgaaagaa ctaaccggac cagagcagaa gggaacagat tacgtgaagc   1140
tggtaatatt aatcagtcac taatgacgct aagaacatgt atggatgtcc taagagagaa   1200
ccaaatgtat ggaactaaca agatggttcc atatcgagat tcaaagttaa cccatctgtt   1260
caagaactac tttgatgggg aaggaaaagt gcggatgatc gtgtgtgtga accccaaggc   1320
tgaagattat gaagaaaact tgcaagtcat gagatttgcg gaagtgactc aagaagttga   1380
agtagcaaga cctgtagaca aggcaatatg tggtttaacg cctgggagga gatacagaaa   1440
ccagcctcga ggtccagttg gaaatgaacc attggttact gacgtggttt tgcagagttt   1500
tccacctttg ccgtcatgcg aaattttgga tatcaacgat gagcagacac ttccaaggct   1560
gattgaagcc ttagagaaac gacataactt acgacaaatg atgattgatg agtttaacaa   1620
acaatctaat gcttttaaag ctttgttaca agaatttgac aatgctgttt taagtaaaga   1680
aaaccacatg caagggaaac taaatgaaaa ggagaagatg atctcaggac agaaattgga   1740
aatagaacga ctggaaaaga aaaacaaaac tttagaatat aagattgaga ttttagagaa   1800
aacaactact atctatgagg aagataaacg caatttgcaa caggaacttg aaactcagaa   1860
ccagaaactt cagcgacagt ttctgagaa acgcagatta gaagccaggt tgcaaggcat    1920
ggtgacagaa acgacaatga agtgggagaa agaatgtgag cgtagagtgg cagccaaaca   1980
gctggagatg cagaataaac tctgggttaa agatgaaaag ctgaaacaac tgaaggctat   2040
tgttactgaa cctaaaactg agaagccaga gagaccctct cgggagcgag atcgagaaaa   2100
agttactcaa agatctgttt ctccatcacc tgtgccttta ctctttcaac ctgatcagaa   2160
cgcaccacca attcgtctcc gacacagacg atcacgctct gcaggagaca gatgggtaga   2220
tcataagccc gcctctaaca tgcaaactga aacagtcatg cagccacatg tccctcatgc   2280
catcacagta tctgttgcaa atgaaaaggc actagctaag tgtgagaagt acatgctgac   2340
ccaccaggaa ctagcctccg atggggagat tgaaactaaa ctaattaagg gtgatattta   2400
taaaacaagg ggtggtggac aatctgttca gtttactgat attgagactt taaagcaaga   2460
```

-continued

```
atcaccaaat ggtagtcgaa aacgaagatc ttccacagta gcacctgccc aaccagatgg   2520

tgcagagtct gaatggacgc gatgtagaaa caaggtgttc tgtggctgtg agatgagagc   2580

aggatcccag ctggacctga tatcagcatc acggcacaac ccaagcgcaa aaagccatga   2640

aactgacagt cccagtactg aaagaacatt ttcatttgtg tggatgattt ctcgaaagcc   2700

atgccagaag cagtcttcca ggtcatcttg tagaactcca gctttggttg aaaatcacgg   2760

acctcagcta catcatacac tgacccagaa taaagctttc cctatggttc caaagacaac   2820

tagtattcaa caaaccttgt atagtgtatg ttttgccata tttaatatta atagcagagg   2880

aagactcctt ttttcatcac tgtatgaatt ttttataatg ttttttttaa aatatatttc   2940

atgtatactt ataaactaat tcacacaagt gtttgtctta gatgattaag gaagactata   3000

tctagatcat gtctgatttt ttattgtgac ttctccagcc ctggtctgaa tttcttaagg   3060

ttttataaac aaatgctgct atttattagc tgcaagaatg cactttagaa ctatttgaca   3120

attcagactt tcaaaataaa gatgtaaatg actggccaat aataaccatt ttaggaaggt   3180

gttttgaatt ctgtatgtat atattcactt tctgacattt agatatgcca aaagaattaa   3240

aatcaaaagc actaaggg                                                 3258

<210> SEQ ID NO 27
<211> LENGTH: 957
<212> TYPE: PRT
<213> ORGANISM: Human

<400> SEQUENCE: 27

Met Leu Ser Ala Arg Ala Lys Thr Pro Arg Lys Pro Thr Val Lys Lys
1               5                   10                  15

Gly Pro Lys Arg Thr Leu Lys Thr Gln Leu Gly Tyr Cys Arg Val Arg
            20                  25                  30

Leu Gly Phe Pro Asp Gln Glu Cys Cys Ile Glu Val Ile Asn Asn Thr
        35                  40                  45

Thr Val Gln Leu His Thr Pro Glu Gly Tyr Arg Leu Asn Arg Asn Gly
    50                  55                  60

Asp Tyr Lys Glu Thr Gln Tyr Ser Phe Lys Gln Val Phe Gly Thr His
65                  70                  75                  80

Thr Thr Gln Lys Glu Leu Phe Asp Val Val Ala Asn Pro Leu Val Asn
                85                  90                  95

Asp Leu Ile His Gly Lys Asn Gly Leu Leu Phe Thr Tyr Gly Val Thr
            100                 105                 110

Gly Ser Gly Lys Thr His Thr Met Thr Gly Ser Pro Gly Glu Gly Gly
        115                 120                 125

Leu Leu Pro Arg Cys Leu Asp Met Ile Phe Asn Ser Ile Gly Ser Phe
    130                 135                 140

Gln Ala Lys Arg Tyr Val Phe Lys Ser Asn Asp Arg Asn Ser Met Asp
145                 150                 155                 160

Ile Gln Cys Glu Val Asp Ala Leu Leu Glu Arg Gln Lys Arg Glu Ala
                165                 170                 175

Met Pro Asn Pro Lys Thr Ser Ser Ser Lys Arg Gln Val Asp Pro Glu
            180                 185                 190

Phe Ala Met Ile Thr Val Gln Glu Phe Cys Lys Ala Glu Glu Val Asp
        195                 200                 205

Glu Asp Ser Val Tyr Gly Val Phe Val Ser Tyr Ile Glu Ile Tyr Asn
    210                 215                 220

Asn Tyr Ile Tyr Asp Leu Leu Glu Glu Val Pro Phe Asp Pro Ile Asn
```

-continued

```
225                 230                 235                 240

Pro Asn Leu His Asn Leu Asn Cys Phe Val Lys Ile Lys Asn His Asn
                245                 250                 255

Met Tyr Val Ala Gly Cys Thr Glu Val Glu Val Lys Ser Thr Glu Glu
            260                 265                 270

Ala Phe Glu Val Phe Trp Arg Gly Gln Lys Lys Arg Arg Ile Ala Asn
        275                 280                 285

Thr His Leu Asn Arg Glu Ser Ser Arg Ser His Ser Val Phe Asn Ile
    290                 295                 300

Lys Leu Val Gln Ala Pro Leu Asp Ala Asp Gly Asp Asn Val Leu Gln
305                 310                 315                 320

Glu Lys Glu Gln Ile Thr Ile Ser Gln Leu Ser Leu Val Asp Leu Ala
                325                 330                 335

Gly Ser Glu Arg Thr Asn Arg Thr Arg Ala Glu Gly Asn Arg Leu Arg
            340                 345                 350

Glu Ala Gly Asn Ile Asn Gln Ser Leu Met Thr Leu Arg Thr Cys Met
        355                 360                 365

Asp Val Leu Arg Glu Asn Gln Met Tyr Gly Thr Asn Lys Met Val Pro
    370                 375                 380

Tyr Arg Asp Ser Lys Thr His Leu Phe Lys Asn Tyr Phe Asp Gly Glu
385                 390                 395                 400

Gly Lys Val Arg Met Ile Val Cys Val Asn Pro Lys Ala Glu Asp Tyr
                405                 410                 415

Glu Glu Asn Leu Gln Val Met Arg Phe Ala Glu Val Thr Gln Glu Val
            420                 425                 430

Glu Val Ala Arg Pro Val Asp Lys Ala Ile Cys Gly Leu Thr Pro Gly
        435                 440                 445

Arg Arg Tyr Arg Asn Gln Pro Arg Gly Pro Val Gly Asn Glu Pro Leu
    450                 455                 460

Val Thr Asp Val Val Leu Gln Ser Phe Pro Pro Leu Pro Ser Cys Glu
465                 470                 475                 480

Ile Leu Asp Ile Asn Asp Glu Gln Thr Leu Pro Arg Leu Ile Glu Ala
                485                 490                 495

Leu Glu Lys Arg His Asn Leu Arg Gln Met Met Ile Asp Glu Phe Asn
            500                 505                 510

Lys Gln Ser Asn Ala Phe Lys Ala Leu Leu Gln Glu Phe Asp Asn Ala
        515                 520                 525

Val Leu Ser Lys Glu Asn His Met Gln Gly Lys Leu Asn Glu Lys Glu
    530                 535                 540

Lys Met Ile Ser Gly Gln Lys Leu Glu Ile Glu Arg Leu Glu Lys Lys
545                 550                 555                 560

Asn Lys Thr Leu Glu Tyr Lys Ile Glu Ile Leu Glu Lys Thr Thr Thr
                565                 570                 575

Ile Tyr Glu Glu Asp Lys Arg Asn Leu Gln Gln Glu Leu Glu Thr Gln
            580                 585                 590

Asn Gln Lys Leu Gln Arg Gln Phe Ser Glu Lys Arg Arg Leu Glu Ala
        595                 600                 605

Arg Leu Gln Gly Met Val Thr Glu Thr Thr Met Lys Trp Glu Lys Glu
    610                 615                 620

Cys Glu Arg Arg Val Ala Ala Lys Gln Leu Glu Met Gln Asn Lys Leu
625                 630                 635                 640

Trp Val Lys Asp Glu Lys Leu Lys Gln Leu Lys Ala Ile Val Thr Glu
                645                 650                 655
```

```
Pro Lys Thr Glu Lys Pro Glu Arg Pro Ser Arg Glu Arg Asp Arg Glu
            660                 665                 670

Lys Val Thr Gln Arg Ser Val Ser Pro Ser Pro Val Pro Leu Leu Phe
        675                 680                 685

Gln Pro Asp Gln Asn Ala Pro Pro Ile Arg Leu Arg His Arg Arg Ser
    690                 695                 700

Arg Ser Ala Gly Asp Arg Trp Val Asp His Lys Pro Ala Ser Asn Met
705                 710                 715                 720

Gln Thr Glu Thr Val Met Gln Pro His Val Pro His Ala Ile Thr Val
                725                 730                 735

Ser Val Ala Asn Glu Lys Ala Leu Ala Lys Cys Glu Lys Tyr Met Leu
            740                 745                 750

Thr His Gln Glu Leu Ala Ser Asp Gly Glu Ile Glu Thr Lys Leu Ile
        755                 760                 765

Lys Gly Asp Ile Tyr Lys Thr Arg Gly Gly Gly Gln Ser Val Gln Phe
    770                 775                 780

Thr Asp Ile Glu Thr Leu Lys Gln Glu Ser Pro Asn Gly Ser Arg Lys
785                 790                 795                 800

Arg Arg Ser Ser Thr Val Ala Pro Ala Gln Pro Asp Gly Ala Glu Ser
                805                 810                 815

Glu Trp Thr Arg Cys Arg Asn Lys Val Phe Cys Gly Cys Glu Met Arg
            820                 825                 830

Ala Gly Ser Gln Leu Asp Leu Ile Ser Ala Ser Arg Asn Pro Ser Ala
        835                 840                 845

Lys Ser His Glu Thr Asp Ser Pro Ser Thr Glu Arg Thr Phe Ser Phe
    850                 855                 860

Val Trp Met Ile Ser Arg Lys Pro Cys Gln Lys Gln Ser Ser Arg Ser
865                 870                 875                 880

Ser Cys Arg Thr Pro Ala Leu Val Glu Asn His Gly Pro Gln Leu His
                885                 890                 895

His Thr Leu Thr Gln Asn Lys Ala Phe Pro Met Val Pro Lys Thr Thr
            900                 905                 910

Ser Ile Gln Gln Thr Leu Tyr Ser Val Cys Phe Ala Ile Phe Asn Ile
        915                 920                 925

Asn Ser Arg Gly Arg Leu Leu Phe Ser Ser Leu Tyr Glu Phe Phe Ile
    930                 935                 940

Met Phe Phe Leu Lys Tyr Ile Ser Cys Ile Leu Ile Asn
945                 950                 955
```

<210> SEQ ID NO 28
<211> LENGTH: 4858
<212> TYPE: DNA
<213> ORGANISM: Human

<400> SEQUENCE: 28

```
agactccggc cctgtcggc cgccaagccc ctccgcccct cacagcgccc aggtccgcgg      60

ccgggccttg attttttggc ggggaccgtc atggcgtcgc agccaaattc gtctgcgaag     120

aagaaagagg agaaggggaa gaacatccag gtggtggtga gatgcagacc atttaatttg     180

gcagagcgga aagctagcgc ccattcaata gtagaatgtg atcctgtacg aaaagaagtt     240

agtgtacgaa ctggaggatt ggctgacaag agctcaagga aaacatacac ttttgatatg     300

gtgtttggag catctactaa acagattgat gtttaccgaa gtgttgtttg tccaattctg     360

gatgaagtta ttatgggcta taattgcact atctttgcgt atggccaaac tggcactgga     420
```

-continued

```
aaaactttta caatggaagg tgaaaggtca cctaatgaag agtatacctg ggaagaggat    480
cccttggctg gtataattcc acgtaccctt catcaaattt ttgagaaact tactgataat    540
ggtactgaat tttcagtcaa agtgtctctg ttggagatct ataatgaaga gctttttgat    600
cttcttaatc catcatctga tgtttctgag agactacaga tgtttgatga tccccgtaac    660
aagagaggag tgataattaa aggtttagaa gaaattacag tacacaacaa ggatgaagtc    720
tatcaaattt tagaaaaggg ggcagcaaaa aggacaactg cagctactct gatgaatgca    780
tactctagtc gttcccactc agttttctct gttacaatac atatgaaaga aactacgatt    840
gatggagaag agcttgttaa aatcggaaag ttgaacttgg ttgatcttgc aggaagtgaa    900
aacattggcc gttctggagc tgttgataag agagctcggg aagctggaaa tataaatcaa    960
tccctgttga ctttgggaag ggtcattact gcccttgtag aaagaacacc tcatgttcct   1020
tatcgagaat ctaaactaac tagaatcctc caggattctc ttggagggcg tacaagaaca   1080
tctataattg caacaatttc tcctgcatct ctcaatcttg aggaaactct gagtacattg   1140
gaatatgctc atagagcaaa gaacatattg aataagcctg aagtgaatca gaaactcacc   1200
aaaaaagctc ttattaagga gtatacggag gagatagaac gtttaaaacg agatcttgct   1260
gcagcccgtg agaaaaatgg agtgtatatt tctgaagaaa attttagagt catgagtgga   1320
aaattaactg ttcaagaaga gcagattgta gaattgattg aaaaaattgg tgctgttgag   1380
gaggagctga atagggttac agagttgttt atggataata aaaatgaact tgaccagtgt   1440
aaatctgacc tgcaaaataa aacacaagaa cttgaaacca ctcaaaaaca tttgcaagaa   1500
actaaattac aacttgttaa agaagaatat atcacatcag ctttggaaag tactgaggag   1560
aaacttcatg atgctgccag caagctgctt aacacagttg aagaaactac aaaagatgta   1620
tctggtctcc attccaaact ggatcgtaag aaggcagttg accaacacaa tgcagaagct   1680
caggatattt ttggcaaaaa cctgaatagt ctgtttaata atatggaaga attaattaag   1740
gatggcagct caaagcaaaa ggccatgcta gaagtacata agaccttatt tggtaatctg   1800
ctgtcttcca gtgtctctgc attagatacc attactacag tagcacttgg atctctcaca   1860
tctattccag aaaatgtgtc tactcatgtt tctcagattt ttaatatgat actaaaagaa   1920
caatcattag cagcagaaag taaaactgta ctacaggaat tgattaatgt actcaagact   1980
gatcttctaa gttcactgga aatgatttta tccccaactg tggtgtctat actgaaaatc   2040
aatagtcaac taaagcatat tttcaagact tcattgacag tggccgataa gatagaagat   2100
caaaaaaagg aactagatgg ctttctcagt atactgtgta acaatctaca tgaactacaa   2160
gaaaatacca tttgttcctt ggttgagtca caaaagcaat gtggaaacct aactgaagac   2220
ctgaagacaa taaagcagac ccattcccag gaactttgca agttaatgaa tctttggaca   2280
gagagattct gtgctttgga ggaaaagtgt gaaaatatac agaaaccact tagtagtgtc   2340
caggaaaata tacagcagaa atctaaggat atagtcaaca aaatgacttt tcacagtcaa   2400
aaattttgtg ctgattctga tggcttctca caggaactca gaaattttaa ccaagaaggt   2460
acaaaattgg ttgaagaatc tgtgaaacac tctgataaac tcaatggcaa cctggaaaaa   2520
atatctcaag agactgaaca gagatgtgaa tctctgaaca caagaacagt ttatttttct   2580
gaacagtggg tatcttcctt aaatgaaagg gaacaggaac ttcacaactt attggaggtt   2640
gtaagccaat gttgtgaggc ttcaagttca gacatcactg agaaatcaga tggacgtaag   2700
gcagctcatg agaaacagca taacattttt cttgatcaga tgactattga tgaagataaa   2760
```

-continued

```
ttgatagcac aaaatctaga acttaatgaa accataaaaa ttggtttgac taagcttaat   2820
tgctttctgg aacaggatct gaaactggat atcccaacag gtacgacacc acagaggaaa   2880
agttatttat acccatcaac actggtaaga actgaaccac gtgaacatct ccttgatcag   2940
ctgaaaagga aacagcctga gctgttaatg atgctaaact gttcagaaaa caacaaagaa   3000
gagacaattc cggatgtgga tgtagaagag gcagttctgg ggcagtatac tgaagaacct   3060
ctaagtcaag agccatctgt agatgctggt gtggattgtt catcaattgg cggggttcca   3120
tttttccagc ataaaaaatc acatggaaaa gacaaagaaa acagaggcat taacacactg   3180
gagaggtcta aagtggaaga aactacagag cacttggtta caaagagcag attacctctg   3240
cgagcccaga tcaaccttta attcacttgg gggttggcaa ttttattttt aaagaaaact   3300
taaaaataaa acctgaaacc ccagaacttg agccttgtgt atagatttta aaagaatata   3360
tatatcagcc gggcgcggtg gctcatgcct gtaatcccag cactttggga ggctgaggcg   3420
ggtggattgc ttgagcccag gagtttgaga ccagcctggc caacgtggca aaacctcgtc   3480
tctgttaaaa attagccggg cgtggtggca cactcctgta atcccagcta ctggggaggc   3540
tgaggcacga gaatcacttg aacccaggaa gcggggttgc agtgagccaa ggtacacca    3600
ctacactcca gcctgggcaa cagagcaaga ctcggtctca aaaacaaaat ttaaaaaaga   3660
tataaggcag tactgtaaat tcagttgaat tttgatatct acccattttt ctgtcatccc   3720
tatagttcac tttgtattaa attgggtttc atttgggatt tgcaatgtaa atacgtattt   3780
ctagttttca tataaagtag ttcttttata acaaatgaaa agtatttttc ttgtatatta   3840
ttaagtaatg aatatataag aactgtactc ttctcagctt gagcttaaca taggtaaata   3900
tcaccaacat ctgtccttag aaaggaccat ctcatgtttt ttttcttgct atgacttgtg   3960
tattttcttg catcctccct agacttccct atttcgcttt ctcctcggct cactttctcc   4020
ctttttattt ttcaccaaac catttgtaga gctacaaaac ctatcctttc ttattttcag   4080
tagtcagaat tttatctaga aatcttttaa cacctttttta gtggttattt ctaaaatcac   4140
tgtcaacaat aaatctaacc ctagttgtat ccctccttta agtatttaaa acttgttgcc   4200
ccaaatgtga aagcatttaa ttcctttaag aggcctaact cattcaccct gacagagttc   4260
acaaaaagcc cactttagag tatacattgc tattatggga gaccacccag acatctgact   4320
aatggctctg tgccacactc caagacctgt gccttttaga gaagctcaca atgatttaag   4380
gactgtttga aacttccaat tatgtctata atttatattc ttttgtttac atgatgaaac   4440
tttttgttgt tgcttgtttg tatataatac aatgtgtaca tgtatctttt tctcgattca   4500
aatcttaacc cttaggactc tggtattttt gatctggcaa ccatatttct ggaagttgag   4560
atgtttcagc ttgaagaacc aaaacagaag gaatatgtac aaagaataaa ttttctgctc   4620
acgatgagtt tagtgtgtaa agtttagaga catctgactt tgatagctaa attaaaccaa   4680
accctattga agaattgaat atatgctact tcaagaaact aaattgatct cgtagaatta   4740
tcttaataaa ataatggcta taatttctct gcaaaatcag atgtcagcat aagcgatgga   4800
taatacctaa taaactgccc tcagtaaatc catggttaat aaatgtggtt tctacatt     4858
```

<210> SEQ ID NO 29
<211> LENGTH: 1056
<212> TYPE: PRT
<213> ORGANISM: Human

<400> SEQUENCE: 29

Met Ala Ser Gln Pro Asn Ser Ser Ala Lys Lys Lys Glu Glu Lys Gly

-continued

```
 1               5                   10                  15

Lys Asn Ile Gln Val Val Val Arg Cys Arg Pro Phe Asn Leu Ala Glu
            20                  25                  30

Arg Lys Ala Ser Ala His Ser Ile Val Glu Cys Asp Pro Val Arg Lys
        35                  40                  45

Glu Val Ser Val Arg Thr Gly Gly Leu Ala Asp Lys Ser Ser Arg Lys
    50                  55                  60

Thr Tyr Thr Phe Asp Met Val Phe Gly Ala Ser Thr Lys Gln Ile Asp
65                  70                  75                  80

Val Tyr Arg Ser Val Val Cys Pro Ile Leu Asp Glu Val Ile Met Gly
                85                  90                  95

Tyr Asn Cys Thr Ile Phe Ala Tyr Gly Gln Thr Gly Thr Gly Lys Thr
            100                 105                 110

Phe Thr Met Glu Gly Glu Arg Ser Pro Asn Glu Glu Tyr Thr Trp Glu
        115                 120                 125

Glu Asp Pro Leu Ala Gly Ile Ile Pro Arg Thr Leu His Gln Ile Phe
    130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
                165                 170                 175

Asp Val Ser Glu Arg Leu Gln Met Phe Asp Asp Pro Arg Asn Lys Arg
            180                 185                 190

Gly Val Ile Ile Lys Gly Leu Glu Glu Ile Thr Val His Asn Lys Asp
        195                 200                 205

Glu Val Tyr Gln Ile Leu Glu Lys Gly Ala Ala Lys Arg Thr Thr Ala
    210                 215                 220

Ala Thr Leu Met Asn Ala Tyr Ser Ser Arg Ser His Ser Val Phe Ser
225                 230                 235                 240

Val Thr Ile His Met Lys Glu Thr Thr Ile Asp Gly Glu Glu Leu Val
                245                 250                 255

Lys Ile Gly Lys Leu Asn Leu Val Asp Leu Ala Gly Ser Glu Asn Ile
            260                 265                 270

Gly Arg Ser Gly Ala Val Asp Lys Arg Ala Arg Glu Ala Gly Asn Ile
        275                 280                 285

Asn Gln Ser Leu Leu Thr Leu Gly Arg Val Ile Thr Ala Leu Val Glu
    290                 295                 300

Arg Thr Pro His Val Pro Tyr Arg Glu Ser Lys Leu Thr Arg Ile Leu
305                 310                 315                 320

Gln Asp Ser Leu Gly Gly Arg Thr Arg Thr Ser Ile Ile Ala Thr Ile
                325                 330                 335

Ser Pro Ala Ser Leu Asn Leu Glu Glu Thr Leu Ser Thr Leu Glu Tyr
            340                 345                 350

Ala His Arg Ala Lys Asn Ile Leu Asn Lys Pro Glu Val Asn Gln Lys
        355                 360                 365

Leu Thr Lys Lys Ala Leu Ile Lys Glu Tyr Thr Glu Glu Ile Glu Arg
    370                 375                 380

Leu Lys Arg Asp Leu Ala Ala Ala Arg Glu Lys Asn Gly Val Tyr Ile
385                 390                 395                 400

Ser Glu Glu Asn Phe Arg Val Met Ser Gly Lys Leu Thr Val Gln Glu
                405                 410                 415

Glu Gln Ile Val Glu Leu Ile Glu Lys Ile Gly Ala Val Glu Glu Glu
            420                 425                 430
```

-continued

```
Leu Asn Arg Val Thr Glu Leu Phe Met Asp Asn Lys Asn Glu Leu Asp
        435                 440                 445

Gln Cys Lys Ser Asp Leu Gln Asn Lys Thr Gln Glu Leu Glu Thr Thr
    450                 455                 460

Gln Lys His Leu Gln Glu Thr Lys Leu Gln Leu Val Lys Glu Glu Tyr
465                 470                 475                 480

Ile Thr Ser Ala Leu Glu Ser Thr Glu Glu Lys Leu His Asp Ala Ala
                485                 490                 495

Ser Lys Leu Leu Asn Thr Val Glu Glu Thr Thr Lys Asp Val Ser Gly
            500                 505                 510

Leu His Ser Lys Leu Asp Arg Lys Lys Ala Val Asp Gln His Asn Ala
        515                 520                 525

Glu Ala Gln Asp Ile Phe Gly Lys Asn Leu Asn Ser Leu Phe Asn Asn
    530                 535                 540

Met Glu Glu Leu Ile Lys Asp Gly Ser Ser Lys Gln Lys Ala Met Leu
545                 550                 555                 560

Glu Val His Lys Thr Leu Phe Gly Asn Leu Leu Ser Ser Ser Val Ser
                565                 570                 575

Ala Leu Asp Thr Ile Thr Thr Val Ala Leu Gly Ser Leu Thr Ser Ile
            580                 585                 590

Pro Glu Asn Val Ser Thr His Val Ser Gln Ile Phe Asn Met Ile Leu
        595                 600                 605

Lys Glu Gln Ser Leu Ala Ala Glu Ser Lys Thr Val Leu Gln Glu Leu
    610                 615                 620

Ile Asn Val Leu Lys Thr Asp Leu Leu Ser Ser Leu Glu Met Ile Leu
625                 630                 635                 640

Ser Pro Thr Val Val Ser Ile Leu Lys Ile Asn Ser Gln Leu Lys His
                645                 650                 655

Ile Phe Lys Thr Ser Leu Thr Val Ala Asp Lys Ile Glu Asp Gln Lys
            660                 665                 670

Lys Glu Leu Asp Gly Phe Leu Ser Ile Leu Cys Asn Asn Leu His Glu
        675                 680                 685

Leu Gln Glu Asn Thr Ile Cys Ser Leu Val Glu Ser Gln Lys Gln Cys
    690                 695                 700

Gly Asn Leu Thr Glu Asp Leu Lys Thr Ile Lys Gln Thr His Ser Gln
705                 710                 715                 720

Glu Leu Cys Lys Leu Met Asn Leu Trp Thr Glu Arg Phe Cys Ala Leu
                725                 730                 735

Glu Glu Lys Cys Glu Asn Ile Gln Lys Pro Leu Ser Ser Val Gln Glu
            740                 745                 750

Asn Ile Gln Gln Lys Ser Lys Asp Ile Val Asn Lys Met Thr Phe His
        755                 760                 765

Ser Gln Lys Phe Cys Ala Asp Ser Asp Gly Phe Ser Gln Glu Leu Arg
    770                 775                 780

Asn Phe Asn Gln Glu Gly Thr Lys Leu Val Glu Glu Ser Val Lys His
785                 790                 795                 800

Ser Asp Lys Leu Asn Gly Asn Leu Glu Lys Ile Ser Gln Glu Thr Glu
                805                 810                 815

Gln Arg Cys Glu Ser Leu Asn Thr Arg Thr Val Tyr Phe Ser Glu Gln
            820                 825                 830

Trp Val Ser Ser Leu Asn Glu Arg Glu Gln Glu Leu His Asn Leu Leu
        835                 840                 845
```

-continued

```
Glu Val Val Ser Gln Cys Cys Glu Ala Ser Ser Ser Asp Ile Thr Glu
    850                 855                 860

Lys Ser Asp Gly Arg Lys Ala Ala His Glu Lys Gln His Asn Ile Phe
865                 870                 875                 880

Leu Asp Gln Met Thr Ile Asp Glu Asp Lys Leu Ile Ala Gln Asn Leu
                885                 890                 895

Glu Leu Asn Glu Thr Ile Lys Ile Gly Leu Thr Lys Leu Asn Cys Phe
            900                 905                 910

Leu Glu Gln Asp Leu Lys Leu Asp Ile Pro Thr Gly Thr Thr Pro Gln
        915                 920                 925

Arg Lys Ser Tyr Leu Tyr Pro Ser Thr Leu Val Arg Thr Glu Pro Arg
    930                 935                 940

Glu His Leu Leu Asp Gln Leu Lys Arg Lys Gln Pro Glu Leu Leu Met
945                 950                 955                 960

Met Leu Asn Cys Ser Glu Asn Asn Lys Glu Glu Thr Ile Pro Asp Val
                965                 970                 975

Asp Val Glu Glu Ala Val Leu Gly Gln Tyr Thr Glu Glu Pro Leu Ser
            980                 985                 990

Gln Glu Pro Ser Val Asp Ala Gly Val Asp Cys Ser Ser Ile Gly Gly
        995                 1000                1005

Val Pro Phe Phe Gln His Lys Lys Ser His Gly Lys Asp Lys Glu Asn
    1010                1015                1020

Arg Gly Ile Asn Thr Leu Glu Arg Ser Lys Val Glu Glu Thr Thr Glu
1025                1030                1035                1040

His Leu Val Thr Lys Ser Arg Leu Pro Leu Arg Ala Gln Ile Asn Leu
                1045                1050                1055


<210> SEQ ID NO 30
<211> LENGTH: 8257
<212> TYPE: DNA
<213> ORGANISM: Human

<400> SEQUENCE: 30

taaatttaaa ggcggggcgg cctgtgagcc ctgaagtgcc ggccgcggag ggtcctggcc      60

attttggtgg gaccagttca gcctgatagg atggcggagg aaggagccgt ggccgtctgc     120

gtgcgagtgc ggccgctgaa cagcagagaa gaatcacttg gagaaactgc ccaagtttac     180

tggaaaactg acaataatgt catttatcaa gttgatggaa gtaaatcctt caattttgat     240

cgtgtctttc atggtaatga aactaccaaa aatgtgtatg aagaaatagc agcaccaatc     300

atcgattctg ccatacaagg ctacaatggt actatatttg cctatggaca gactgcttca     360

ggaaaaacat ataccatgat gggttcagaa gatcatttgg gagttatacc cagggcaatt     420

catgacattt tccaaaaaat taagaagttt cctgataggg aatttctctt acgtgtatct     480

tacatggaaa tatacaatga aaccattaca gatttactct gtggcactca aaaaatgaaa     540

cctttaatta ttcgagaaga tgtcaatagg aatgtgtatg ttgctgatct cacagaagaa     600

gttgtatata catcagaaat ggctttgaaa tggattacaa agggagaaaa gagcaggcat     660

tatggagaaa caaaaatgaa tcaaagaagc agtcgttctc ataccatctt taggatgatt     720

ttggaaagca gagagaaggg tgaaccttct aattgtgaag gatctgttaa ggtatcccat     780

ttgaatttgg ttgatcttgc aggcagtgaa agagctgctc aaacaggcgc tgcaggtgtg     840

cggctcaagg aaggctgtaa tataaatcga agcttattta ttttgggaca agtgatcaag     900

aaacttagtg atggacaagt tggtggtttc ataaattatc gagatagcaa gttaacacga     960
```

-continued

```
attcttcaga attccttggg aggaaatcca aagacacgta ttatctgcac aattactcca   1020
gtatcttttg atgaaactct tactgctctc cagtttgcca gtactgctaa atatatgaag   1080
aatactcctt atgttaatga ggtatcaact gatgaagctc tcctgaaaag gtatagaaaa   1140
gaaataatgg atcttaaaaa acaattagag gaggtttctt tagagacgcg ggctcaggca   1200
atggaaaaag accaattggc ccaacttttg gaagaaaaag atttgcttca gaaagtacag   1260
aatgagaaaa ttgaaaactt aacacggatg ctggtgacct cttcttccct cacgttgcaa   1320
caggaattaa aggctaaaag aaaacgaaga gttacttggt gccttggcaa aattaacaaa   1380
atgaagaact caaactatgc agatcaattt aatataccaa caaatataac aacaaaaaca   1440
cataagcttt ctataaattt attacgagaa attgatgaat ctgtctgttc agagtctgat   1500
gttttcagta acactcttga tacattaagt gagatagaat ggaatccagc aacaaagcta   1560
ctaaatcagg agaatataga aagtgagttg aactcacttc gtgctgacta tgataatctg   1620
gtattagact atgaacaact acgaacagaa aaagaagaaa tggaattgaa attaaaagaa   1680
aagaatgatt tggatgaatt tgaggctcta gaaagaaaaa ctaaaaaaga tcaagagatg   1740
caactaattc atgaaatttc gaacttaaag aatttagtta agcatcgaga agtatataat   1800
caagatcttg agaatgaact cagttcaaaa gtagagctgc ttagagaaaa ggaagaccag   1860
attaagaagc tacaggaata catagactct caaaagctag aaaatataaa aatggacttg   1920
tcatactcat tggaaagcat tgaagaccca aaacaaatga agcagactct gtttgatgct   1980
gaaactgtag cccttgatgc caagagagaa tcagcctttc ttagaagtga aaatctggag   2040
ttgaaggaga aaatgaaaga acttgcaact acatacaagc aaatggaaaa tgatattcag   2100
ttatatcaaa gccaattgga ggcaaaaaag aaaatgcaag ttgatctgga gaaagaatta   2160
caatctgctt ttaatgagat aacaaaactc acctccctta tagatggcaa agttccaaaa   2220
gatttgctct gtaatttgga attggaagga aagattactg atcttcagaa agaactaaat   2280
aaagaagttg aagaaaatga agctttgcgg gaagaagtca ttttgctttc agaattgaaa   2340
tctttacctt ctgaagtaga aaggctgagg aaagagatac aagacaaatc tgaagagctc   2400
catataataa catcagaaaa agataaattg ttttctgaag tagttcataa ggagagtaga   2460
gttcaaggtt tacttgaaga aattgggaaa acaaaagatg acctagcaac tacacagtcg   2520
aattataaaa gcactgatca agaattccaa aatttcaaaa cccttcatat ggactttgag   2580
caaaagtata agatggtcct tgaggagaat gagagaatga atcaggaaat agttaatctc   2640
tctaaagaag cccaaaaatt tgattcgagt ttgggtgctt tgaagaccga gctttcttac   2700
aagacccaag aacttcagga gaaaacacgt gaggttcaag aaagactaaa tgagatggaa   2760
cagctgaagg aacaattaga aaatagagat tctccgctgc aaactgtaga aagggagaaa   2820
acactgatta ctgagaaact gcagcaaact ttagaagaag taaaaacttt aactcaagaa   2880
aaagatgatc taaaacaact ccaagaaagc ttgcaaattg agagggacca actcaaaagt   2940
gatattcacg atactgttaa catgaatata gatactcaag aacaattacg aaatgctctt   3000
gagtctctga aacaacatca agaaacaatt aatacactaa aatcgaaaat ttctgaggaa   3060
gtttccagga atttgcatat ggaggaaaat acaggagaaa ctaaagatga atttcagcaa   3120
aagatggttg gcatagataa aaaacaggat ttggaagcta aaaataccca aacactaact   3180
gcagatgtta aggataatga gataattgag caacaaagga agatattttc tttaatacag   3240
gagaaaaatg aactccaaca aatgttagag agtgttatag cagaaaagga acaattgaag   3300
actgacctaa aggaaaatat tgaaatgacc attgaaaacc aggaagaatt aagacttctt   3360
```

-continued

```
ggggatgaac ttaaaaagca acaagagata gttgcacaag aaaagaacca tgccataaag   3420
aaagaaggag agctttctag gacctgtgac agactggcag aagttgaaga aaaactaaag   3480
gaaaagagcc agcaactcca agaaaaacag caacaacttc ttaatgtaca agaagagatg   3540
agtgagatgc agaaaaagat taatgaaata gagaatttaa agaatgaatt aaagaacaaa   3600
gaattgacat tggaacatat ggaaacagag aggcttgagt tggctcagaa acttaatgaa   3660
aattatgagg aagtgaaatc tataaccaaa gaaagaaaag ttctaaagga attacagaag   3720
tcatttgaaa cagagagaga ccaccttaga ggatatataa gagaaattga agctacaggc   3780
ctacaaacca aagaagaact aaaaattgct catattcacc taaaagaaca ccaagaaact   3840
attgatgaac taagaagaag cgtatctgag aagacagctc aaataataaa tactcaggac   3900
ttagaaaaat cccataccaa attacaagaa gagatcccag tgcttcatga ggaacaagag   3960
ttactgccta atgtgaaaaa agtcagtgag actcaggaaa caatgaatga actggagtta   4020
ttaacagaac agtccacaac caaggactca acaacactgg caagaataga aatggaaagg   4080
ctcaggttga atgaaaaatt tcaagaaagt caggaagaga taaaatctct aaccaaggaa   4140
agagacaacc ttaaaacgat aaaagaagcc cttgaagtta aacatgacca gctgaaagaa   4200
catattagag aaactttggc taaaatccag gagtctcaaa gcaaacaaga acagtcctta   4260
aatatgaaag aaaaagacaa tgaaactacc aaaatcgtga gtgagatgga gcaattcaaa   4320
cccaaagatt cagcactact aaggatagaa atagaaatgc tcggattgtc caaaagactt   4380
caagaaagtc atgatgaaat gaaatctgta gctaaggaga aagatgacct acagaggctg   4440
caagaagttc ttcaatctga aagtgaccag ctcaaagaaa acataaaaga aattgtagct   4500
aaacacctgg aaactgaaga ggaacttaaa gttgctcatt gttgcctgaa agaacaagag   4560
gaaactatta atgagttaag agtgaatctt tcagagaagg aaactgaaat atcaaccatt   4620
caaaagcagt tagaagcaat caatgataaa ttacagaaca agatccaaga gatttatgag   4680
aaagaggaac aacttaatat aaaacaaatt agtgaggttc aggaaaacgt gaatgaactg   4740
aaacaattca aggagcatcg caaagccaag gattcagcac tacaaagtat agaaagtaag   4800
atgctcgagt tgaccaacag acttcaagaa agtcaagaag aaatacaaat tatgattaag   4860
gaaaaagagg aaatgaaaag agtacaggag gcccttcaga tagagagaga ccaactgaaa   4920
gaaaacacta aagaaattgt agctaaaatg aaagaatctc aagaaaaaga atatcagttt   4980
cttaagatga cagctgtcaa tgagactcag gagaaaatgt gtgaaataga acacttgaag   5040
gagcaatttg agacccagaa gttaaacctg gaaaacatag aaacggagaa tataaggttg   5100
actcagatac tacatgaaaa ccttgaagaa atgagatctg taacaaaaga aagagatgac   5160
cttaggagtg tggaggagac tctcaaagta gagagagacc agctcaagga aaaccttaga   5220
gaaactataa ctagagacct agaaaaacaa gaggagctaa aaattgttca catgcatctg   5280
aaggagcacc aagaaactat tgataaacta agagggattg tttcagagaa aacaaatgaa   5340
atatcaaata tgcaaaagga cttagaacac tcaaatgatg ccttaaaagc acaggatctg   5400
aaaatacaag aggaactaag aattgctcac atgcatctga aagagcagca ggaaactatt   5460
gacaaactca gaggaattgt ttctgagaag acagataaac tatcaaatat gcaaaaagat   5520
ttagaaaatt caaatgctaa attacaagaa aagattcaag aacttaaggc aaatgaacat   5580
caacttatta cgttaaaaaa agatgtcaat gagacacaga aaaaagtgtc tgaaatggag   5640
caactaaaga aacaaataaa agaccaaagc ttaactctga gtaaattaga aatagagaat   5700
```

-continued

```
ttaaatttgg ctcaagaact tcatgaaaac cttgaagaaa tgaaatctgt aatgaaagaa   5760
agagataatc taagaagagt agaggagaca ctcaaactgg agagagacca actcaaggaa   5820
agcctgcaag aaaccaaagc tagagatctg gaaatacaac aggaactaaa aactgctcgt   5880
atgctatcaa aagaacacaa agaaactgtt gataaactta gagaaaaaat ttcagaaaag   5940
acaattcaaa tttcagacat tcaaaaggat ttagataaat caaaagatga attacagaaa   6000
aagatccaag aacttcagaa aaaagaactt caactgctta gagtgaaaga agatgtcaat   6060
atgagtcata aaaaaattaa tgaaatggaa cagttgaaga agcaatttga gccaaactat   6120
ctatgcaagt gtgagatgga taacttccag ttgactaaga aacttcatga aagccttgaa   6180
gaaataagaa ttgtagctaa agaaagagat gagctaagga ggataaaaga atctctcaaa   6240
atggaaaggg accaattcat agcaacctta agggaaatga tagctagaga ccgacagaac   6300
caccaagtaa aacctgaaaa aaggttacta agtgatggac aacagcacct tatggaaagc   6360
ctgagagaaa agtgctctag aataaaagag cttttgaaga gatactcaga gatggatgat   6420
cattatgagt gcttgaatag attgtctctt gacttggaga aggaaattga attccacaga   6480
atcatgaaga aactgaagta tgtgttaagc tatgttacaa aaataaaaga agaacaacat   6540
gaatgcatca ataaatttga aatggatttt attgatgaag tggaaaagca aaaggaattg   6600
ctaattaaaa tacagcacct tcaacaagat tgtgatgtac catccagaga attaagggat   6660
ctcaaattga accagaatat ggatctacat attgaggaaa ttctcaaaga tttctcagaa   6720
agtgagttcc ctagcataaa gactgaattt caacaagtac taagtaatag gaaagaaatg   6780
acacagtttt tggaagagtg gttaaatact cgttttgata tagaaaagct taaaaatggc   6840
atccagaaag aaaatgatag gatttgtcaa gtgaataact tctttaataa cagaataatt   6900
gccataatga atgaatcaac agagtttgag gaaagaagtg ctaccatatc caaagagtgg   6960
gaacaggacc tgaaatcact gaaagagaaa aatgaaaaac tatttaaaaa ctaccaaaca   7020
ttgaagactt ccttggcatc tggtgcccag gttaatccta ccacacaaga caataagaat   7080
cctcatgtta catcaagagc tacacagtta accacagaga aaattcgaga gctggaaaat   7140
tcactgcatg aagctaaaga aagtgctatg cataaggaaa gcaagattat aaagatgcag   7200
aaagaacttg aggtgactaa tgacataata gcaaaacttc aagccaaagt tcatgaatca   7260
aataaatgcc ttgaaaaaac aaaagagaca attcaagtac ttcaggacaa agttgcttta   7320
ggagctaagc catataaaga agaaattgaa gatctcaaaa tgaagcttgt gaaaatagac   7380
ctagagaaaa tgaaaaatgc caaagaattt gaaaaggaaa tcagtgctac aaaagccact   7440
gtagaatatc aaaaggaagt tataaggcta ttgagagaaa atctcagaag aagtcaacag   7500
gcccaagata cctcagtgat atcagaacat actgatcctc agccttcaaa taaaccctta   7560
acttgtggag gtggcagcgg cattgtacaa aacacaaaag ctcttatttt gaaaagtgaa   7620
catataaggc tagaaaaaga aatttctaag ttaaagcagc aaaatgaaca gctaataaaa   7680
caaaagaatg aattgttaag caataatcag catctttcca atgaggtcaa aacttggaag   7740
gaaagaaccc ttaaaagaga ggctcacaaa caagtaactt gtgagaattc tccaaagtct   7800
cctaaagtga ctggaacagc ttctaaaaag aaacaaatta caccctctca atgcaaggaa   7860
cggaatttac aagatcctgt gccaaaggaa tcaccaaaat cttgtttttt tgatagccga   7920
tcaaagtctt taccatcacc tcatccagtt cgctattttg ataactcaag tttaggcctt   7980
tgtccagagg tgcaaaatgc aggagcagag agtgtggatt ctcagccagg tccttggcac   8040
gcctcctcag gcaaggatgt gcctgagtgc aaaactcagt agactcctct ttgtcacttc   8100
```

-continued

```
tctggagatc cagcattcct tatttggaaa tgactttgtt tatgtgtcta tccctggtaa   8160

tgatgttgta gtgcagctta atttcaattc agtctttact ttgccactag agttgaaaga   8220

taagggaaca ggaaatgaat gcattgtggt aatttag                            8257


<210> SEQ ID NO 31
<211> LENGTH: 2662
<212> TYPE: PRT
<213> ORGANISM: Human

<400> SEQUENCE: 31

Met Ala Glu Glu Gly Ala Val Ala Val Cys Val Arg Val Arg Pro Leu
 1               5                  10                  15

Asn Ser Arg Glu Glu Ser Leu Gly Glu Thr Ala Gln Val Tyr Trp Lys
            20                  25                  30

Thr Asp Asn Asn Val Ile Tyr Gln Val Asp Gly Ser Lys Ser Phe Asn
        35                  40                  45

Phe Asp Arg Val Phe His Gly Asn Glu Thr Thr Lys Asn Val Tyr Glu
    50                  55                  60

Glu Ile Ala Ala Pro Ile Ile Asp Ser Ala Ile Gln Gly Tyr Asn Gly
65                  70                  75                  80

Thr Ile Phe Ala Tyr Gly Gln Thr Ala Ser Gly Lys Thr Tyr Thr Met
                85                  90                  95

Met Gly Ser Glu Asp His Leu Gly Val Ile Pro Arg Ala Ile His Asp
            100                 105                 110

Ile Phe Gln Lys Ile Lys Lys Phe Pro Asp Arg Glu Phe Leu Leu Arg
        115                 120                 125

Val Ser Tyr Met Glu Ile Tyr Asn Glu Thr Ile Thr Asp Leu Leu Cys
    130                 135                 140

Gly Thr Gln Lys Met Lys Pro Leu Ile Ile Arg Glu Asp Val Asn Arg
145                 150                 155                 160

Asn Val Tyr Val Ala Asp Leu Thr Glu Glu Val Val Tyr Thr Ser Glu
                165                 170                 175

Met Ala Leu Lys Trp Ile Thr Lys Gly Glu Lys Ser Arg His Tyr Gly
            180                 185                 190

Glu Thr Lys Met Asn Gln Arg Ser Ser Arg Ser His Thr Ile Phe Arg
        195                 200                 205

Met Ile Leu Glu Ser Arg Glu Lys Gly Glu Pro Ser Asn Cys Glu Gly
    210                 215                 220

Ser Val Lys Val Ser His Leu Asn Leu Val Asp Leu Ala Gly Ser Glu
225                 230                 235                 240

Arg Ala Ala Gln Thr Gly Ala Ala Gly Val Arg Leu Lys Glu Gly Cys
                245                 250                 255

Asn Ile Asn Arg Ser Leu Phe Ile Leu Gly Gln Val Ile Lys Lys Leu
            260                 265                 270

Ser Asp Gly Gln Val Gly Gly Phe Ile Asn Tyr Arg Asp Ser Lys Leu
        275                 280                 285

Thr Arg Ile Leu Gln Asn Ser Leu Gly Gly Asn Pro Lys Thr Arg Ile
    290                 295                 300

Ile Cys Thr Ile Thr Pro Val Ser Phe Asp Glu Thr Leu Thr Ala Leu
305                 310                 315                 320

Gln Phe Ala Ser Thr Ala Lys Tyr Met Lys Asn Thr Pro Tyr Val Asn
                325                 330                 335

Glu Val Ser Thr Asp Glu Ala Leu Leu Lys Arg Tyr Arg Lys Glu Ile
```

-continued

```
            340                 345                 350

Met Asp Leu Lys Lys Gln Leu Glu Glu Val Ser Leu Glu Thr Arg Ala
        355                 360                 365

Gln Ala Met Glu Lys Asp Gln Leu Ala Gln Leu Leu Glu Glu Lys Asp
    370                 375                 380

Leu Leu Gln Lys Val Gln Asn Glu Lys Ile Glu Asn Leu Thr Arg Met
385                 390                 395                 400

Leu Val Thr Ser Ser Ser Leu Thr Leu Gln Gln Glu Leu Lys Ala Lys
                405                 410                 415

Arg Lys Arg Arg Val Thr Trp Cys Leu Gly Lys Ile Asn Lys Met Lys
            420                 425                 430

Asn Ser Asn Tyr Ala Asp Gln Phe Asn Ile Pro Thr Asn Ile Thr Thr
        435                 440                 445

Lys Thr His Lys Leu Ser Ile Asn Leu Leu Arg Glu Ile Asp Glu Ser
    450                 455                 460

Val Cys Ser Glu Ser Asp Val Phe Ser Asn Thr Leu Asp Thr Leu Ser
465                 470                 475                 480

Glu Ile Glu Trp Asn Pro Ala Thr Lys Leu Leu Asn Gln Glu Asn Ile
                485                 490                 495

Glu Ser Glu Leu Asn Ser Leu Arg Ala Asp Tyr Asp Asn Leu Val Leu
            500                 505                 510

Asp Tyr Glu Gln Leu Arg Thr Glu Lys Glu Glu Met Glu Leu Lys Leu
        515                 520                 525

Lys Glu Lys Asn Asp Leu Asp Glu Phe Glu Ala Leu Glu Arg Lys Thr
    530                 535                 540

Lys Lys Asp Gln Glu Met Gln Leu Ile His Glu Ile Ser Asn Leu Lys
545                 550                 555                 560

Asn Leu Val Lys His Arg Glu Val Tyr Asn Gln Asp Leu Glu Asn Glu
                565                 570                 575

Leu Ser Ser Lys Val Glu Leu Leu Arg Glu Lys Glu Asp Gln Ile Lys
            580                 585                 590

Lys Leu Gln Glu Tyr Ile Asp Ser Gln Lys Leu Glu Asn Ile Lys Met
        595                 600                 605

Asp Leu Ser Tyr Ser Leu Glu Ser Ile Glu Asp Pro Lys Gln Met Lys
    610                 615                 620

Gln Thr Leu Phe Asp Ala Glu Thr Val Ala Leu Asp Ala Lys Arg Glu
625                 630                 635                 640

Ser Ala Phe Leu Arg Ser Glu Asn Leu Glu Leu Lys Glu Lys Met Lys
                645                 650                 655

Glu Leu Ala Thr Thr Tyr Lys Gln Met Glu Asn Asp Ile Gln Leu Tyr
            660                 665                 670

Gln Ser Gln Leu Glu Ala Lys Lys Lys Met Gln Val Asp Leu Glu Lys
        675                 680                 685

Glu Leu Gln Ser Ala Phe Asn Glu Ile Thr Lys Leu Thr Ser Leu Ile
    690                 695                 700

Asp Gly Lys Val Pro Lys Asp Leu Leu Cys Asn Leu Glu Leu Glu Gly
705                 710                 715                 720

Lys Ile Thr Asp Leu Gln Lys Glu Leu Asn Lys Glu Val Glu Glu Asn
                725                 730                 735

Glu Ala Leu Arg Glu Glu Val Ile Leu Leu Ser Glu Leu Lys Ser Leu
            740                 745                 750

Pro Ser Glu Val Glu Arg Leu Arg Lys Glu Ile Gln Asp Lys Ser Glu
        755                 760                 765
```

-continued

```
Glu Leu His Ile Ile Thr Ser Glu Lys Asp Lys Leu Phe Ser Glu Val
    770                 775                 780

Val His Lys Glu Ser Arg Val Gln Gly Leu Leu Glu Glu Ile Gly Lys
785                 790                 795                 800

Thr Lys Asp Asp Leu Ala Thr Thr Gln Ser Asn Tyr Lys Ser Thr Asp
                805                 810                 815

Gln Glu Phe Gln Asn Phe Lys Thr Leu His Met Asp Phe Glu Gln Lys
            820                 825                 830

Tyr Lys Met Val Leu Glu Glu Asn Glu Arg Met Asn Gln Glu Ile Val
        835                 840                 845

Asn Leu Ser Lys Glu Ala Gln Lys Phe Asp Ser Ser Leu Gly Ala Leu
    850                 855                 860

Lys Thr Glu Leu Ser Tyr Lys Thr Gln Glu Leu Gln Glu Lys Thr Arg
865                 870                 875                 880

Glu Val Gln Glu Arg Leu Asn Glu Met Glu Gln Leu Lys Glu Gln Leu
                885                 890                 895

Glu Asn Arg Asp Ser Pro Leu Gln Thr Val Glu Arg Glu Lys Thr Leu
            900                 905                 910

Ile Thr Glu Lys Leu Gln Gln Thr Leu Glu Glu Val Lys Thr Leu Thr
        915                 920                 925

Gln Glu Lys Asp Asp Leu Lys Gln Leu Gln Glu Ser Leu Gln Ile Glu
    930                 935                 940

Arg Asp Gln Leu Lys Ser Asp Ile His Asp Thr Val Asn Met Asn Ile
945                 950                 955                 960

Asp Thr Gln Glu Gln Leu Arg Asn Ala Leu Glu Ser Leu Lys His Gln
                965                 970                 975

Glu Thr Ile Asn Thr Leu Lys Ser Lys Ile Ser Glu Glu Val Ser Arg
            980                 985                 990

Asn Leu His Met Glu Glu Asn Thr Gly Glu Thr Lys Asp Glu Phe Gln
        995                 1000                1005

Gln Lys Met Val Gly Ile Asp Lys Lys Gln Asp Leu Glu Ala Lys Asn
    1010                1015                1020

Thr Gln Thr Leu Thr Ala Asp Val Lys Asp Asn Glu Ile Ile Glu Gln
1025                1030                1035                1040

Gln Arg Lys Ile Phe Ser Leu Ile Gln Glu Lys Asn Glu Leu Gln Gln
                1045                1050                1055

Met Leu Glu Ser Val Ile Ala Glu Lys Glu Gln Leu Lys Thr Asp Leu
            1060                1065                1070

Lys Glu Asn Ile Glu Met Thr Ile Glu Asn Gln Glu Glu Leu Arg Leu
        1075                1080                1085

Leu Gly Asp Glu Leu Lys Lys Gln Gln Glu Ile Val Ala Gln Glu Lys
    1090                1095                1100

Asn His Ala Ile Lys Lys Glu Gly Glu Leu Ser Arg Thr Cys Asp Arg
1105                1110                1115                1120

Leu Ala Glu Val Glu Glu Lys Leu Lys Glu Lys Ser Gln Gln Leu Gln
                1125                1130                1135

Glu Lys Gln Gln Gln Leu Leu Asn Val Gln Glu Glu Met Ser Glu Met
            1140                1145                1150

Gln Lys Lys Ile Asn Glu Ile Glu Asn Leu Lys Asn Glu Leu Lys Asn
        1155                1160                1165

Lys Glu Leu Thr Leu Glu His Met Glu Thr Glu Arg Leu Glu Leu Ala
    1170                1175                1180
```

-continued

```
Gln Lys Leu Asn Glu Asn Tyr Glu Glu Val Lys Ser Ile Thr Lys Glu
1185                1190                1195                1200

Arg Lys Val Leu Lys Glu Leu Gln Lys Ser Phe Glu Thr Glu Arg Asp
                1205                1210                1215

His Leu Arg Gly Tyr Ile Arg Glu Ile Glu Ala Thr Gly Leu Gln Thr
            1220                1225                1230

Lys Glu Glu Leu Lys Ile Ala His Ile His Leu Lys Glu His Gln Glu
        1235                1240                1245

Thr Ile Asp Glu Leu Arg Arg Ser Val Ser Glu Lys Thr Ala Gln Ile
    1250                1255                1260

Ile Asn Thr Gln Asp Leu Glu Lys Ser His Thr Lys Leu Gln Glu Glu
1265                1270                1275                1280

Ile Pro Val Leu His Glu Glu Gln Glu Leu Leu Pro Asn Val Lys Lys
                1285                1290                1295

Val Ser Glu Thr Gln Glu Thr Met Asn Glu Leu Glu Leu Leu Thr Glu
            1300                1305                1310

Gln Ser Thr Thr Lys Asp Ser Thr Thr Leu Ala Arg Ile Glu Met Glu
        1315                1320                1325

Arg Leu Arg Leu Asn Glu Lys Phe Gln Glu Ser Gln Glu Glu Ile Lys
    1330                1335                1340

Ser Leu Thr Lys Glu Arg Asp Asn Leu Lys Thr Ile Lys Glu Ala Leu
1345                1350                1355                1360

Glu Val Lys His Asp Gln Leu Lys Glu His Ile Arg Glu Thr Leu Ala
                1365                1370                1375

Lys Ile Gln Glu Ser Gln Ser Lys Gln Glu Gln Ser Leu Asn Met Lys
            1380                1385                1390

Glu Lys Asp Asn Glu Thr Thr Lys Ile Val Ser Glu Met Glu Gln Phe
        1395                1400                1405

Lys Pro Lys Asp Ser Ala Leu Leu Arg Ile Glu Ile Glu Met Leu Gly
    1410                1415                1420

Leu Ser Lys Arg Leu Gln Glu Ser His Asp Glu Met Lys Ser Val Ala
1425                1430                1435                1440

Lys Glu Lys Asp Asp Leu Gln Arg Leu Gln Glu Val Leu Gln Ser Glu
                1445                1450                1455

Ser Asp Gln Leu Lys Glu Asn Ile Lys Glu Ile Val Ala Lys His Leu
            1460                1465                1470

Glu Thr Glu Glu Glu Leu Lys Val Ala His Cys Cys Leu Lys Glu Gln
        1475                1480                1485

Glu Glu Thr Ile Asn Glu Leu Arg Val Asn Leu Ser Glu Lys Glu Thr
    1490                1495                1500

Glu Ile Ser Thr Ile Gln Lys Gln Leu Glu Ala Ile Asn Asp Lys Leu
1505                1510                1515                1520

Gln Asn Lys Ile Gln Glu Ile Tyr Glu Lys Glu Glu Gln Leu Asn Ile
                1525                1530                1535

Lys Gln Ile Ser Glu Val Gln Glu Asn Val Asn Glu Leu Lys Gln Phe
            1540                1545                1550

Lys Glu His Arg Lys Ala Lys Asp Ser Ala Leu Gln Ser Ile Glu Ser
        1555                1560                1565

Lys Met Leu Glu Leu Thr Asn Arg Leu Gln Glu Ser Gln Glu Glu Ile
    1570                1575                1580

Gln Ile Met Ile Lys Glu Lys Glu Glu Met Lys Arg Val Gln Glu Ala
1585                1590                1595                1600

Leu Gln Ile Glu Arg Asp Gln Leu Lys Glu Asn Thr Lys Glu Ile Val
```

-continued

```
                1605                1610                1615

Ala Lys Met Lys Glu Ser Gln Glu Lys Glu Tyr Gln Phe Leu Lys Met
            1620                1625                1630

Thr Ala Val Asn Glu Thr Gln Glu Lys Met Cys Glu Ile Glu His Leu
        1635                1640                1645

Lys Glu Gln Phe Glu Thr Gln Lys Leu Asn Leu Glu Asn Ile Glu Thr
    1650                1655                1660

Glu Asn Ile Arg Leu Thr Gln Ile Leu His Glu Asn Leu Glu Glu Met
1665                1670                1675                1680

Arg Ser Val Thr Lys Glu Arg Asp Asp Leu Arg Ser Val Glu Glu Thr
                1685                1690                1695

Leu Lys Val Glu Arg Asp Gln Leu Lys Glu Asn Leu Arg Glu Thr Ile
            1700                1705                1710

Thr Arg Asp Leu Glu Lys Gln Glu Glu Leu Lys Ile Val His Met His
        1715                1720                1725

Leu Lys Glu His Gln Glu Thr Ile Asp Lys Leu Arg Gly Ile Val Ser
    1730                1735                1740

Glu Lys Thr Asn Glu Ile Ser Asn Met Gln Lys Asp Leu Glu His Ser
1745                1750                1755                1760

Asn Asp Ala Leu Lys Ala Gln Asp Leu Lys Ile Gln Glu Glu Leu Arg
                1765                1770                1775

Ile Ala His Met His Leu Lys Glu Gln Gln Glu Thr Ile Asp Lys Leu
            1780                1785                1790

Arg Gly Ile Val Ser Glu Lys Thr Asp Lys Leu Ser Asn Met Gln Lys
        1795                1800                1805

Asp Leu Glu Asn Ser Asn Ala Lys Leu Gln Glu Lys Ile Gln Glu Leu
    1810                1815                1820

Lys Ala Asn Glu His Gln Leu Ile Thr Leu Lys Lys Asp Val Asn Glu
1825                1830                1835                1840

Thr Gln Lys Lys Val Ser Glu Met Glu Gln Leu Lys Lys Gln Ile Lys
                1845                1850                1855

Asp Gln Ser Leu Thr Leu Ser Lys Leu Glu Ile Glu Asn Leu Asn Leu
            1860                1865                1870

Ala Gln Glu Leu His Glu Asn Leu Glu Glu Met Lys Ser Val Met Lys
        1875                1880                1885

Glu Arg Asp Asn Leu Arg Arg Val Glu Glu Thr Leu Lys Leu Glu Arg
    1890                1895                1900

Asp Gln Leu Lys Glu Ser Leu Gln Glu Thr Lys Ala Arg Asp Leu Glu
1905                1910                1915                1920

Ile Gln Gln Glu Leu Lys Thr Ala Arg Met Leu Ser Lys Glu His Lys
                1925                1930                1935

Glu Thr Val Asp Lys Leu Arg Glu Lys Ile Ser Glu Lys Thr Ile Gln
            1940                1945                1950

Ile Ser Asp Ile Gln Lys Asp Leu Asp Lys Ser Lys Asp Glu Leu Gln
        1955                1960                1965

Lys Lys Ile Gln Glu Leu Gln Lys Lys Glu Leu Gln Leu Leu Arg Val
    1970                1975                1980

Lys Glu Asp Val Asn Met Ser His Lys Lys Ile Asn Glu Met Glu Gln
1985                1990                1995                2000

Leu Lys Lys Gln Phe Glu Pro Asn Tyr Leu Cys Lys Cys Glu Met Asp
                2005                2010                2015

Asn Phe Gln Leu Thr Lys Lys Leu His Glu Ser Leu Glu Glu Ile Arg
            2020                2025                2030
```

-continued

```
Ile Val Ala Lys Glu Arg Asp Glu Leu Arg Arg Ile Lys Glu Ser Leu
        2035                2040                2045

Lys Met Glu Arg Asp Gln Phe Ile Ala Thr Leu Arg Glu Met Ile Ala
    2050                2055                2060

Arg Asp Arg Gln Asn His Gln Val Lys Pro Glu Lys Arg Leu Leu Ser
2065                2070                2075                2080

Asp Gly Gln Gln His Leu Met Glu Ser Leu Arg Glu Lys Cys Ser Arg
                2085                2090                2095

Ile Lys Glu Leu Leu Lys Arg Tyr Ser Glu Met Asp Asp His Tyr Glu
            2100                2105                2110

Cys Leu Asn Arg Leu Ser Leu Asp Leu Glu Lys Glu Ile Glu Phe His
        2115                2120                2125

Arg Ile Met Lys Lys Leu Lys Tyr Val Leu Ser Tyr Val Thr Lys Ile
    2130                2135                2140

Lys Glu Glu Gln His Glu Cys Ile Asn Lys Phe Glu Met Asp Phe Ile
2145                2150                2155                2160

Asp Glu Val Glu Lys Gln Lys Glu Leu Leu Ile Lys Ile Gln His Leu
                2165                2170                2175

Gln Gln Asp Cys Asp Val Pro Ser Arg Glu Leu Arg Asp Leu Lys Leu
            2180                2185                2190

Asn Gln Asn Met Asp Leu His Ile Glu Glu Ile Leu Lys Asp Phe Ser
        2195                2200                2205

Glu Ser Glu Phe Pro Ser Ile Lys Thr Glu Phe Gln Gln Val Leu Ser
    2210                2215                2220

Asn Arg Lys Glu Met Thr Gln Phe Leu Glu Glu Trp Leu Asn Thr Arg
2225                2230                2235                2240

Phe Asp Ile Glu Lys Leu Lys Asn Gly Ile Gln Lys Glu Asn Asp Arg
                2245                2250                2255

Ile Cys Gln Val Asn Asn Phe Phe Asn Asn Arg Ile Ile Ala Ile Met
            2260                2265                2270

Asn Glu Ser Thr Glu Phe Glu Glu Arg Ser Ala Thr Ile Ser Lys Glu
        2275                2280                2285

Trp Glu Gln Asp Leu Lys Ser Leu Lys Glu Lys Asn Glu Lys Leu Phe
    2290                2295                2300

Lys Asn Tyr Gln Thr Leu Lys Thr Ser Leu Ala Ser Gly Ala Gln Val
2305                2310                2315                2320

Asn Pro Thr Thr Gln Asp Asn Lys Asn Pro His Val Thr Ser Arg Ala
                2325                2330                2335

Thr Gln Leu Thr Thr Glu Lys Ile Arg Glu Leu Glu Asn Ser Leu His
            2340                2345                2350

Glu Ala Lys Glu Ser Ala Met His Lys Glu Ser Lys Ile Ile Lys Met
        2355                2360                2365

Gln Lys Glu Leu Glu Val Thr Asn Asp Ile Ile Ala Lys Leu Gln Ala
    2370                2375                2380

Lys Val His Glu Ser Asn Lys Cys Leu Glu Lys Thr Lys Glu Thr Ile
2385                2390                2395                2400

Gln Val Leu Gln Asp Lys Val Ala Leu Gly Ala Lys Pro Tyr Lys Glu
                2405                2410                2415

Glu Ile Glu Asp Leu Lys Met Lys Leu Val Lys Ile Asp Leu Glu Lys
            2420                2425                2430

Met Lys Asn Ala Lys Glu Phe Glu Lys Glu Ile Ser Ala Thr Lys Ala
        2435                2440                2445
```

-continued

Thr Val Glu Tyr Gln Lys Glu Val Ile Arg Leu Leu Arg Glu Asn Leu
2450 2455 2460

Arg Arg Ser Gln Gln Ala Gln Asp Thr Ser Val Ile Ser Glu His Thr
2465 2470 2475 2480

Asp Pro Gln Pro Ser Asn Lys Pro Leu Thr Cys Gly Gly Gly Ser Gly
2485 2490 2495

Ile Val Gln Asn Thr Lys Ala Leu Ile Leu Lys Ser Glu His Ile Arg
2500 2505 2510

Leu Glu Lys Glu Ile Ser Lys Leu Lys Gln Gln Asn Glu Gln Leu Ile
2515 2520 2525

Lys Gln Lys Asn Glu Leu Leu Ser Asn Asn Gln His Leu Ser Asn Glu
2530 2535 2540

Val Lys Thr Trp Lys Glu Arg Thr Leu Lys Arg Glu Ala His Lys Gln
2545 2550 2555 2560

Val Thr Cys Glu Asn Ser Pro Lys Ser Pro Lys Val Thr Gly Thr Ala
2565 2570 2575

Ser Lys Lys Lys Gln Ile Thr Pro Ser Gln Cys Lys Glu Arg Asn Leu
2580 2585 2590

Gln Asp Pro Val Pro Lys Glu Ser Pro Lys Ser Cys Phe Phe Asp Ser
2595 2600 2605

Arg Ser Lys Ser Leu Pro Ser Pro His Pro Val Arg Tyr Phe Asp Asn
2610 2615 2620

Ser Ser Leu Gly Leu Cys Pro Glu Val Gln Asn Ala Gly Ala Glu Ser
2625 2630 2635 2640

Val Asp Ser Gln Pro Gly Pro Trp His Ala Ser Ser Gly Lys Asp Val
2645 2650 2655

Pro Glu Cys Lys Thr Gln
2660

<210> SEQ ID NO 32
<211> LENGTH: 2740
<212> TYPE: DNA
<213> ORGANISM: Human

<400> SEQUENCE: 32
gcgaaattga ggtttcttgg tattgcgcgt ttctcttcct tgctgactct ccgaatggcc 60
atggactcgt cgcttcaggc ccgcctgttt cccggtctcg ctatcaagat ccaacgcagt 120
aatggtttaa ttcacagtgc caatgtaagg actgtgaact tggagaaatc ctgtgtttca 180
gtggaatggg cagaaggagg tgccacaaag ggcaaagaga ttgattttga tgatgtggct 240
gcaataaacc cagaactctt acagcttctt cccttacatc cgaaggacaa tctgcccttg 300
caggaaaatg taacaatcca gaaacaaaaa cggagatccg tcaactccaa aattcctgct 360
ccaaaagaaa gtcttcgaag ccgctccact cgcatgtcca ctgtctcaga gcttcgcatc 420
acggctcagg agaatgacat ggaggtggag ctgcctgcag ctgcaaactc ccgcaagcag 480
ttttcagttc ctcctgcccc cactaggcct tcctgccctg cagtggctga aataccattg 540
aggatggtca gcgaggagat ggaagagcaa gtccattcca tccgtggcag ctcttctgca 600
aaccctgtga actcagttcg gaggaaatca tgtcttgtga aggaagtgga aaaaatgaag 660
aacaagcgag aagagaagaa ggcccagaac tctgaaatga gaatgaagag agctcaggag 720
tatgacagta gttttccaaa ctgggaattt gcccgaatga ttaaagaatt tcgggctact 780
ttggaatgtc atccacttac tatgactgat cctatcgaag agcacagaat atgtgtctgt 840
gttaggaaac gcccactgaa taagcaagaa ttggccaaga aagaaattga tgtgatttcc 900

-continued

```
attcctagca agtgtctcct cttggtacat gaacccaagt tgaaagtgga cttaacaaag    960
tatctggaga accaagcatt ctgctttgac tttgcatttg atgaaacagc ttcgaatgaa   1020
gttgtctaca ggttcacagc aaggccactg gtacagacaa tctttgaagg tggaaaagca   1080
acttgttttg catatggcca gacaggaagt ggcaagacac atactatggg cggagacctc   1140
tctgggaaag cccagaatgc atccaaaggg atctatgcca tggcctcccg ggacgtcttc   1200
ctcctgaaga atcaaccctg ctaccggaag ttgggcctgg aagtctatgt gacattcttc   1260
gagatctaca atgggaagct gtttgacctg ctcaacaaga aggccaagct gcgcgtgctg   1320
gaggacggca agcaacaggt gcaagtggtg gggctgcagg agcatctggt taactctgct   1380
gatgatgtca tcaagatgct cgacatgggc agcgcctgca gaacctctgg gcagacattt   1440
gccaactcca attcctcccg ctcccacgcg tgcttccaaa ttattcttcg agctaaaggg   1500
agaatgcatg gcaagttctc tttggtagat ctggcaggga atgagcgagg cgcagacact   1560
tccagtgctg accggcagac ccgcatggag ggcgcagaaa tcaacaagag tctcttagcc   1620
ctgaaggagt gcatcagggc cctgggacag aacaaggctc acaccccgtt ccgtgagagc   1680
aagctgacac aggtgctgag ggactccttc attggggaga actctaggac ttgcatgatt   1740
gccacgatct caccaggcat aagctcctgt gaatatactt taaacaccct gagatatgca   1800
gacagggtca aggagctgag cccccacagt gggcccagtg gagagcagtt gattcaaatg   1860
gaaacagaag agatggaagc ctgctctaac ggggcgctga ttccaggcaa tttatccaag   1920
gaagaggagg aactgtcttc ccagatgtcc agctttaacg aagccatgac tcagatcagg   1980
gagctggagg agaaggctat ggaagagctc aaggagatca tacagcaagg accagactgg   2040
cttgagctct ctgagatgac cgagcagcca gactatgacc tggagacctt tgtgaacaaa   2100
gcggaatctg ctctggccca gcaagccaag catttctcag ccctgcgaga tgtcatcaag   2160
gccttacgcc tggccatgca gctggaagag caggctagca gacaaataag cagcaagaaa   2220
cggccccagt gacgactgca aataaaaatc tgtttggttt gacacccagc ctcttccctg   2280
gccctcccca gagaactttg ggtacctggt gggtctaggc agggtctgag ctgggacagg   2340
ttctggtaaa tgccaagtat gggggcatct gggcccaggg cagctgggga gggggtcaga   2400
gtgacatggg acactccttt tctgttcctc agttgtcgcc ctcacgagag gaaggagctc   2460
ttagttaccc ttttgtgttg cccttctttc catcaagggg aatgttctca gcatagagct   2520
ttctccgcag catcctgcct gcgtggactg gctgctaatg gagagctccc tggggttgtc   2580
ctggctctgg ggagagagac ggagccttta gtacagctat ctgctggctc taaaccttct   2640
acgcctttgg gccgagcact gaatgtcttg tactttaaaa aaatgtttct gagacctctt   2700
tctactttac tgtctcccta gagtcctaga ggatccctac                         2740
```

<210> SEQ ID NO 33
<211> LENGTH: 725
<212> TYPE: PRT
<213> ORGANISM: Human

<400> SEQUENCE: 33

```
Met Ala Met Asp Ser Ser Leu Gln Ala Arg Leu Phe Pro Gly Leu Ala
 1               5                  10                  15

Ile Lys Ile Gln Arg Ser Asn Gly Leu Ile His Ser Ala Asn Val Arg
            20                  25                  30

Thr Val Asn Leu Glu Lys Ser Cys Val Ser Val Glu Trp Ala Glu Gly
        35                  40                  45
```

-continued

```
Gly Ala Thr Lys Gly Lys Glu Ile Asp Phe Asp Asp Val Ala Ala Ile
    50                  55                  60

Asn Pro Glu Leu Leu Gln Leu Leu Pro Leu His Pro Lys Asp Asn Leu
65                  70                  75                  80

Pro Leu Gln Glu Asn Val Thr Ile Gln Lys Gln Lys Arg Arg Ser Val
                85                  90                  95

Asn Ser Lys Ile Pro Ala Pro Lys Glu Ser Leu Arg Ser Arg Ser Thr
            100                 105                 110

Arg Met Ser Thr Val Ser Glu Leu Arg Ile Thr Ala Gln Glu Asn Asp
        115                 120                 125

Met Glu Val Glu Leu Pro Ala Ala Ala Asn Ser Arg Lys Gln Phe Ser
    130                 135                 140

Val Pro Pro Ala Pro Thr Arg Pro Ser Cys Pro Ala Val Ala Glu Ile
145                 150                 155                 160

Pro Leu Arg Met Val Ser Glu Glu Met Glu Glu Gln Val His Ser Ile
                165                 170                 175

Arg Gly Ser Ser Ser Ala Asn Pro Val Asn Ser Val Arg Arg Lys Ser
            180                 185                 190

Cys Leu Val Lys Glu Val Glu Lys Met Lys Asn Lys Arg Glu Glu Lys
        195                 200                 205

Lys Ala Gln Asn Ser Glu Met Arg Met Lys Arg Ala Gln Glu Tyr Asp
    210                 215                 220

Ser Ser Phe Pro Asn Trp Glu Phe Ala Arg Met Ile Lys Glu Phe Arg
225                 230                 235                 240

Ala Thr Leu Glu Cys His Pro Leu Thr Met Thr Asp Pro Ile Glu Glu
                245                 250                 255

His Arg Ile Cys Val Cys Val Arg Lys Arg Pro Leu Asn Lys Gln Glu
            260                 265                 270

Leu Ala Lys Lys Glu Ile Asp Val Ile Ser Ile Pro Ser Lys Cys Leu
        275                 280                 285

Leu Leu Val His Glu Pro Lys Leu Lys Val Asp Leu Thr Lys Tyr Leu
    290                 295                 300

Glu Asn Gln Ala Phe Cys Phe Asp Phe Ala Phe Asp Glu Thr Ala Ser
305                 310                 315                 320

Asn Glu Val Val Tyr Arg Phe Thr Ala Arg Pro Leu Val Gln Thr Ile
                325                 330                 335

Phe Glu Gly Gly Lys Ala Thr Cys Phe Ala Tyr Gly Gln Thr Gly Ser
            340                 345                 350

Gly Lys Thr His Thr Met Gly Gly Asp Leu Ser Gly Lys Ala Gln Asn
        355                 360                 365

Ala Ser Lys Gly Ile Tyr Ala Met Ala Ser Arg Asp Val Phe Leu Leu
    370                 375                 380

Lys Asn Gln Pro Cys Tyr Arg Lys Leu Gly Leu Glu Val Tyr Val Thr
385                 390                 395                 400

Phe Phe Glu Ile Tyr Asn Gly Lys Leu Phe Asp Leu Leu Asn Lys Lys
                405                 410                 415

Ala Lys Leu Arg Val Leu Glu Asp Gly Lys Gln Gln Val Gln Val Val
            420                 425                 430

Gly Leu Gln Glu His Leu Val Asn Ser Ala Asp Asp Val Ile Lys Met
        435                 440                 445

Leu Asp Met Gly Ser Ala Cys Arg Thr Ser Gly Gln Thr Phe Ala Asn
    450                 455                 460
```

-continued

```
Ser Asn Ser Ser Arg Ser His Ala Cys Phe Gln Ile Ile Leu Arg Ala
465                 470                 475                 480

Lys Gly Arg Met His Gly Lys Phe Ser Leu Val Asp Leu Ala Gly Asn
                485                 490                 495

Glu Arg Gly Ala Asp Thr Ser Ser Ala Asp Arg Gln Thr Arg Met Glu
            500                 505                 510

Gly Ala Glu Ile Asn Lys Ser Leu Leu Ala Leu Lys Glu Cys Ile Arg
        515                 520                 525

Ala Leu Gly Gln Asn Lys Ala His Thr Pro Phe Arg Glu Ser Lys Leu
    530                 535                 540

Thr Gln Val Leu Arg Asp Ser Phe Ile Gly Glu Asn Ser Arg Thr Cys
545                 550                 555                 560

Met Ile Ala Thr Ile Ser Pro Gly Ile Ser Ser Cys Glu Tyr Thr Leu
                565                 570                 575

Asn Thr Leu Arg Tyr Ala Asp Arg Val Lys Glu Leu Ser Pro His Ser
            580                 585                 590

Gly Pro Ser Gly Glu Gln Leu Ile Gln Met Glu Thr Glu Glu Met Glu
        595                 600                 605

Ala Cys Ser Asn Gly Ala Leu Ile Pro Gly Asn Leu Ser Lys Glu Glu
    610                 615                 620

Glu Glu Leu Ser Ser Gln Met Ser Ser Phe Asn Glu Ala Met Thr Gln
625                 630                 635                 640

Ile Arg Glu Leu Glu Glu Lys Ala Met Glu Glu Leu Lys Glu Ile Ile
                645                 650                 655

Gln Gln Gly Pro Asp Trp Leu Glu Leu Ser Glu Met Thr Glu Gln Pro
            660                 665                 670

Asp Tyr Asp Leu Glu Thr Phe Val Asn Lys Ala Glu Ser Ala Leu Ala
        675                 680                 685

Gln Gln Ala Lys His Phe Ser Ala Leu Arg Asp Val Ile Lys Ala Leu
    690                 695                 700

Arg Leu Ala Met Gln Leu Glu Glu Gln Ala Ser Arg Gln Ile Ser Ser
705                 710                 715                 720

Lys Lys Arg Pro Gln
                725
```

<210> SEQ ID NO 34
<211> LENGTH: 2097
<212> TYPE: DNA
<213> ORGANISM: Human

<400> SEQUENCE: 34

```
gggcgggccc aaggagggag tggaatggcc gcgggcggct cgacgcagca gaggcgacgc      60

gagatggcgg cagcttcagc ggcggcgatc tcaggagctg gtcgctgtcg gctaagcaag     120

attggagcta ctcgtcgtcc acctccagct cgcgtaaggg tggctgtgcg actgcggcca     180

tttgtggatg gaacagcggg agcaagtgat ccccccctgtg tgcggggcat ggacagctgc     240

tctctagaga ttgctaactg gaggaaccac caggagactc tcaaatacca gtttgatgcc     300

ttctatgggg agaggagtac tcagcaggac atctatgcag gttcagtgca gcccatccta     360

aggcacttgc tggaagggca gaatgccagt gtgcttgcct atggacccac aggagctggg     420

aagacgcaca caatgctggg cagcccagag caacctgggg tgatcccgcg ggctctcatg     480

gacctcctgc agctcacaag ggaggagggt gccgagggcc ggccatgggc cctttctgtc     540

accatgtctt acctagagat ctaccaggag aaggtattag acctcctgga ccctgcttcg     600
```

-continued

```
ggagacctgg taatccgaga agactgccgg gggaatatcc tgattccggg tctctcccag    660

aagcccatca gtagctttgc tgattttgag cggcacttcc tgccagccag tcgaaatcgg    720

actgtaggag ccacccggct caaccagcgc tcctcccgca gtcatgctgt gctcctggtc    780

aaggtggacc agcgggaacg tttggcccca tttcgccagc gagagggaaa actctacctg    840

attgacttgg ctgggtcaga ggacaaccgg cgcacaggca acaagggcct tcggctaaaa    900

gagagtggag ccatcaacac ctccctgttt gtcctgggca aagtggtaga tgcgctgaat    960

cagggcctcc ctcgtgtacc ttatcgggac agcaagctca ctcgcctatt gcaggactct   1020

ctgggtggct cagcccacag tatccttatt gccaacattg cccctgagag acgcttctac   1080

ctagacacag tctccgcact caactttgct gccaggtcca aggaggtgat caatcggcct   1140

tttaccaatg agagcctgca gcctcatgcc ttgggacctg ttaagctgtc tcagaaagaa   1200

ttgcttggtc caccagaggc aaagagagcc cgaggccctg aggaagagga gattgggagc   1260

cctgagccca tggcagctcc agcctctgcc tcccagaaac tcagccccct acagaagcta   1320

agcagcatgg acccggccat gctggagcgc ctcctcagct tggaccgtct gcttgcctcc   1380

caggggagcc agggggcccc tctgttgagt accccaaagc gagagcggat ggtgctaatg   1440

aagacagtag aagagaagga cctagagatt gagaggctta agacgaagca aaaagaactg   1500

gaggccaaga tgttggccca gaaggctgag gaaaaggaga accattgtcc cacaatgctc   1560

cggccccttt cacatcgcac agtcacaggg gcaaagcccc tgaaaaaggc tgtggtgatg   1620

cccctacagc taattcagga gcaggcagca tccccaaatg ccgagatcca catcctgaag   1680

aataaaggcc ggaagagaaa gctggagtcc ctggatgccc tagagcctga ggagaaggct   1740

gaggactgct gggagctaca gatcagcccg gagctactgg ctcatgggcg ccaaaaaata   1800

ctggatctgc tgaacgaagg ctcagcccga gatctccgca gtcttcagcg cattggcccg   1860

aagaaggccc agctaatcgt gggctggcgg gagctccacg gccccttcag ccaggtggag   1920

gacctggaac gcgtggaggg cataacgggg aaacagatgg agtccttcct gaaggcaaac   1980

atcctgggtc tcgccgccgg ccagcgctgt ggcgcctcct gaccgtcgtc tcctcactcc   2040

gccttttcaa atttttgtat aaccccgtgt tgtgtaaata cagtttttgc tccggtg      2097
```

<210> SEQ ID NO 35
<211> LENGTH: 665
<212> TYPE: PRT
<213> ORGANISM: Human

<400> SEQUENCE: 35

```
Met Ala Ala Gly Gly Ser Thr Gln Gln Arg Arg Arg Glu Met Ala Ala
 1               5                  10                  15

Ala Ser Ala Ala Ala Ile Ser Gly Ala Gly Arg Cys Arg Leu Ser Lys
            20                  25                  30

Ile Gly Ala Thr Arg Arg Pro Pro Pro Ala Arg Val Arg Val Ala Val
        35                  40                  45

Arg Leu Arg Pro Phe Val Asp Gly Thr Ala Gly Ala Ser Asp Pro Pro
    50                  55                  60

Cys Val Arg Gly Met Asp Ser Cys Ser Leu Glu Ile Ala Asn Trp Arg
65                  70                  75                  80

Asn His Gln Glu Thr Leu Lys Tyr Gln Phe Asp Ala Phe Tyr Gly Glu
                85                  90                  95

Arg Ser Thr Gln Gln Asp Ile Tyr Ala Gly Ser Val Gln Pro Ile Leu
            100                 105                 110
```

-continued

```
Arg His Leu Leu Glu Gly Gln Asn Ala Ser Val Leu Ala Tyr Gly Pro
        115                 120                 125

Thr Gly Ala Gly Lys Thr His Thr Met Leu Gly Ser Pro Glu Gln Pro
    130                 135                 140

Gly Val Ile Pro Arg Ala Leu Met Asp Leu Leu Gln Leu Thr Arg Glu
145                 150                 155                 160

Glu Gly Ala Glu Gly Arg Pro Trp Ala Leu Ser Val Thr Met Ser Tyr
                165                 170                 175

Leu Glu Ile Tyr Gln Glu Lys Val Leu Asp Leu Leu Asp Pro Ala Ser
            180                 185                 190

Gly Asp Leu Val Ile Arg Glu Asp Cys Arg Gly Asn Ile Leu Ile Pro
        195                 200                 205

Gly Leu Ser Gln Lys Pro Ile Ser Ser Phe Ala Asp Phe Glu Arg His
    210                 215                 220

Phe Leu Pro Ala Ser Arg Asn Arg Thr Val Gly Ala Thr Arg Leu Asn
225                 230                 235                 240

Gln Arg Ser Ser Arg Ser His Ala Val Leu Leu Val Lys Val Asp Gln
                245                 250                 255

Arg Glu Arg Leu Ala Pro Phe Arg Gln Arg Glu Gly Lys Leu Tyr Leu
            260                 265                 270

Ile Asp Leu Ala Gly Ser Glu Asp Asn Arg Arg Thr Gly Asn Lys Gly
        275                 280                 285

Leu Arg Leu Lys Glu Ser Gly Ala Ile Asn Thr Ser Leu Phe Val Leu
    290                 295                 300

Gly Lys Val Val Asp Ala Leu Asn Gln Gly Leu Pro Arg Val Pro Tyr
305                 310                 315                 320

Arg Asp Ser Lys Leu Thr Arg Leu Leu Gln Asp Ser Leu Gly Gly Ser
                325                 330                 335

Ala His Ser Ile Leu Ile Ala Asn Ile Ala Pro Glu Arg Arg Phe Tyr
            340                 345                 350

Leu Asp Thr Val Ser Ala Leu Asn Phe Ala Ala Arg Ser Lys Glu Val
        355                 360                 365

Ile Asn Arg Pro Phe Thr Asn Glu Ser Leu Gln Pro His Ala Leu Gly
    370                 375                 380

Pro Val Lys Leu Ser Gln Lys Glu Leu Leu Gly Pro Pro Glu Ala Lys
385                 390                 395                 400

Arg Ala Arg Gly Pro Glu Glu Glu Glu Ile Gly Ser Pro Glu Pro Met
                405                 410                 415

Ala Ala Pro Ala Ser Ala Ser Gln Lys Leu Ser Pro Leu Gln Lys Leu
            420                 425                 430

Ser Ser Met Asp Pro Ala Met Leu Glu Arg Leu Leu Ser Leu Asp Arg
        435                 440                 445

Leu Leu Ala Ser Gln Gly Ser Gln Gly Ala Pro Leu Leu Ser Thr Pro
    450                 455                 460

Lys Arg Glu Arg Met Val Leu Met Lys Thr Val Glu Glu Lys Asp Leu
465                 470                 475                 480

Glu Ile Glu Arg Leu Lys Thr Lys Gln Lys Glu Leu Glu Ala Lys Met
                485                 490                 495

Leu Ala Gln Lys Ala Glu Glu Lys Glu Asn His Cys Pro Thr Met Leu
            500                 505                 510

Arg Pro Leu Ser His Arg Thr Val Thr Gly Ala Lys Pro Leu Lys Lys
        515                 520                 525

Ala Val Val Met Pro Leu Gln Leu Ile Gln Glu Gln Ala Ala Ser Pro
```

-continued

```
    530                 535                 540

Asn Ala Glu Ile His Ile Leu Lys Asn Lys Gly Arg Lys Arg Lys Leu
545                 550                 555                 560

Glu Ser Leu Asp Ala Leu Glu Pro Glu Glu Lys Ala Glu Asp Cys Trp
                565                 570                 575

Glu Leu Gln Ile Ser Pro Glu Leu Leu Ala His Gly Arg Gln Lys Ile
            580                 585                 590

Leu Asp Leu Leu Asn Glu Gly Ser Ala Arg Asp Leu Arg Ser Leu Gln
        595                 600                 605

Arg Ile Gly Pro Lys Lys Ala Gln Leu Ile Val Gly Trp Arg Glu Leu
    610                 615                 620

His Gly Pro Phe Ser Gln Val Glu Asp Leu Glu Arg Val Glu Gly Ile
625                 630                 635                 640

Thr Gly Lys Gln Met Glu Ser Phe Leu Lys Ala Asn Ile Leu Gly Leu
                645                 650                 655

Ala Ala Gly Gln Arg Cys Gly Ala Ser
            660                 665


<210> SEQ ID NO 36
<211> LENGTH: 1779
<212> TYPE: DNA
<213> ORGANISM: Human

<400> SEQUENCE: 36

gtgagaggac tcaaacgttg gaccaagaga accagcagct tcaggaccag ctcagagatg     60

cccagcagca ggtcaaggcc ctggggacag agcgcacaac actggagggg catttagcca    120

aggtacaggc ccaggctgag cagggccaac aggagctgaa gaacttgcgt gcttgtgtcc    180

tggagctgga agagcggctg agcacgccag gagggcttgg tgcaagagct tcagaaaaaa    240

caggtggaat tgcaggaaga acggagggga ctgatgtccc aactagagga gaaggagagg    300

aggctgcaac atcagaagca gccctgtcaa gcagccaagc agaagtggca tctctgcggc    360

aggagactgt ggcccaggca gccttactga ctgagcggga agaacgtctt catgggctag    420

aaatggagcg ccggcgactg cacaaccagc tgcaggaact caagggcaac atccgtgtat    480

tctgccgggt ccgccctgtc ctgccggggg agcccactcc acccccctggc ctcctcctgt   540

ttccctctgg ccctggtggg ccctctgatc ctccaacccg ccttagcctc tcccggtctg    600

acgagcggcg tgggaccctg agtggggcac cagctccccc aactcgccat gatttttcct    660

ttgaccgggt attcccacca ggaagtggac aggatgaagt gtttgaagag attgccatgc    720

ttgtccagtc agccctggat ggctatccag tatgcatctt tgcctatggc cagacaggca    780

gtggcaagac cttcacaatg gagggtgggc ctgggggaga cccccagttg gaggggctga    840

tccctcgggc cctgcggcac ctcttctctg tggctcagga gctgagtggt cagggctgga    900

cctacagctt tgtagcaagc tacgtagaga tctacaatga gactgtccgg gacctgctgg    960

ccactggaac ccggaagggt caagggggcg agtgtgagat tcgccgtgca gggccaggga   1020

gtgaggagct cactgtcacc aatgctcgat atgtccctgt ctcctgtgag aaagaagtgg   1080

acgccctgct tcatctggcc cgccagaatc gggctgtggc ccgcacagcc cagaatgaac   1140

ggtcatcacg cagccacagt gtattccagc tacagatttc tggggagcac tccagccgag   1200

gcctgcagtg tggggccccc ctcagtcttg tggacctggc cgggagtgag cgacttgacc   1260

ccggcttagc cctcggcccc ggggagcggg aacgccttcg ggaaacacag gccattaaca   1320

gcagcctgtc cacgctgggg ctggttatca tggccctgag caacaaggag tcccacgtgc   1380
```

```
cttaccggaa cagcaaactg acctacctgc tgcagaactc tctgggtggt agtgctaaga   1440

tgctcatgtt tgtgaacatt tctccactgg aagagaacgt ctccgagtcc ctcaactctc   1500

tacgctttgc ctccaaggtg aaccagtgtg ttattggtac tgctcaggcc aacaggaagt   1560

gaagacggat ccagatctgt gtgtgtgtgt gtgtgtgtgt gtgtgtgtgt gtgtcctatg   1620

tctatgtatc gggtgagggg tgggagggtt gctggagggt gctttattgg gtggagggca   1680

ccatgtccca gggctatcaa ataaagaata gtttggtttt ttttttaaat aaaggtttta   1740

ttaccatttg cccaagaagg cagatacttt catatctgt                          1779


<210> SEQ ID NO 37
<211> LENGTH: 519
<212> TYPE: PRT
<213> ORGANISM: Human

<400> SEQUENCE: 37

Glu Arg Thr Gln Thr Leu Asp Gln Glu Asn Gln Gln Leu Gln Asp Gln
 1               5                  10                  15

Leu Arg Asp Ala Gln Gln Gln Val Lys Ala Leu Gly Thr Glu Arg Thr
            20                  25                  30

Thr Leu Glu Gly His Leu Ala Lys Val Gln Ala Gln Ala Glu Gln Gly
        35                  40                  45

Gln Gln Glu Leu Lys Asn Leu Arg Ala Cys Val Leu Glu Leu Glu Glu
    50                  55                  60

Arg Leu Ser Thr Pro Gly Gly Leu Gly Ala Arg Ala Ser Glu Lys Thr
65                  70                  75                  80

Gly Gly Ile Ala Gly Arg Thr Glu Gly Thr Asp Val Pro Thr Arg Gly
                85                  90                  95

Glu Gly Glu Glu Ala Ala Thr Ser Glu Ala Ala Leu Ser Ser Ser Gln
            100                 105                 110

Ala Glu Val Ala Ser Leu Arg Gln Glu Thr Val Ala Gln Ala Ala Leu
        115                 120                 125

Leu Thr Glu Arg Glu Glu Arg Leu His Gly Leu Glu Met Glu Arg Arg
    130                 135                 140

Arg Leu His Asn Gln Leu Gln Glu Leu Lys Gly Asn Ile Arg Val Phe
145                 150                 155                 160

Cys Arg Val Arg Pro Val Leu Pro Gly Glu Pro Thr Pro Pro Pro Gly
                165                 170                 175

Leu Leu Leu Phe Pro Ser Gly Pro Gly Gly Pro Ser Asp Pro Pro Thr
            180                 185                 190

Arg Leu Ser Leu Ser Arg Ser Asp Glu Arg Arg Gly Thr Leu Ser Gly
        195                 200                 205

Ala Pro Ala Pro Pro Thr Arg His Asp Phe Ser Phe Asp Arg Val Phe
    210                 215                 220

Pro Pro Gly Ser Gly Gln Asp Glu Val Phe Glu Glu Ile Ala Met Leu
225                 230                 235                 240

Val Gln Ser Ala Leu Asp Gly Tyr Pro Val Cys Ile Phe Ala Tyr Gly
                245                 250                 255

Gln Thr Gly Ser Gly Lys Thr Phe Thr Met Glu Gly Gly Pro Gly Gly
            260                 265                 270

Asp Pro Gln Leu Glu Gly Leu Ile Pro Arg Ala Leu Arg His Leu Phe
        275                 280                 285

Ser Val Ala Gln Glu Leu Ser Gly Gln Gly Trp Thr Tyr Ser Phe Val
    290                 295                 300
```

```
Ala Ser Tyr Val Glu Ile Tyr Asn Glu Thr Val Arg Asp Leu Leu Ala
305                 310                 315                 320

Thr Gly Thr Arg Lys Gly Gln Gly Gly Glu Cys Glu Ile Arg Arg Ala
                325                 330                 335

Gly Pro Gly Ser Glu Glu Leu Thr Val Thr Asn Ala Arg Tyr Val Pro
            340                 345                 350

Val Ser Cys Glu Lys Glu Val Asp Ala Leu Leu His Leu Ala Arg Gln
        355                 360                 365

Asn Arg Ala Val Ala Arg Thr Ala Gln Asn Glu Arg Ser Ser Arg Ser
    370                 375                 380

His Ser Val Phe Gln Leu Gln Ile Ser Gly Glu His Ser Ser Arg Gly
385                 390                 395                 400

Leu Gln Cys Gly Ala Pro Leu Ser Leu Val Asp Leu Ala Gly Ser Glu
                405                 410                 415

Arg Leu Asp Pro Gly Leu Ala Leu Gly Pro Gly Glu Arg Glu Arg Leu
            420                 425                 430

Arg Glu Thr Gln Ala Ile Asn Ser Ser Leu Ser Thr Leu Gly Leu Val
        435                 440                 445

Ile Met Ala Leu Ser Asn Lys Glu Ser His Val Pro Tyr Arg Asn Ser
    450                 455                 460

Lys Leu Thr Tyr Leu Leu Gln Asn Ser Leu Gly Gly Ser Ala Lys Met
465                 470                 475                 480

Leu Met Phe Val Asn Ile Ser Pro Leu Glu Glu Asn Val Ser Glu Ser
                485                 490                 495

Leu Asn Ser Leu Arg Phe Ala Ser Lys Val Asn Gln Cys Val Ile Gly
            500                 505                 510

Thr Ala Gln Ala Asn Arg Lys
        515
```

<210> SEQ ID NO 38
<211> LENGTH: 6972
<212> TYPE: DNA
<213> ORGANISM: Human

<400> SEQUENCE: 38

```
gaggtgttcc ccccacactg gggctcccac tactgcgagg agtgacccac gaaggccaca     60

gagatggccg gggcttcggt gaaggtggcg gtgcgggtcc gcccccttcaa ttcccgggaa    120

atgagccgtg actccaagtg catcattcag atgtctggaa gcaccaccac cattgttaac    180

cccaaacagc ccaaggagac gcccaaaagc ttcagctttg actactccta ctggtcgcac    240

acctcacctg aggacatcaa ctacgcgtcg cagaagcagg tgtaccggga catcggcgag    300

gagatgctgc agcatgcctt tgagggatac aacgtgtgca tcttcgccta tgggcagacg    360

ggtgccggca agtcctacac catgatgggc aagcaggaga aggaccagca gggcatcatc    420

ccacagctct gcgaggacct cttctctcgg atcaacgaca cgaccaacga caacatgtcc    480

tactccgtgg aggtcagcta catggagatt tactgtgagc gcgtccgtga cctcctgaac    540

cccaagaaca agggcaacct tcgcgtgagg gagcacccac tgctggggcc ctacgtggag    600

gacctctcca agctggctgt cacctcctac aatgacatcc aggacctcat ggactcaggg    660

aacaaggcca ggaccgtggc ggccaccaac atgaatgaga ccagcagtcg ctcccacgcc    720

gtcttcaaca tcatcttcac ccagaagcgc catgacgcag agaccaatat caccacggag    780

aaggtgagca aaatcagcct ggtggacctg gctgggagcg agcgggctga ctccacggga    840
```

-continued

```
gccaagggca cgcgcctcaa ggagggggcc aacatcaaca agtcgctgac caccctgggc    900
aaggtcatct ccgccctggc tgaaatggac tccggaccca acaagaacaa gaaaaagaag    960
aagacagatt tcattccgta ccgagattcc gtgttgacct ggctcctccg ggaaaacctg   1020
ggcggtaact caaggacagc tatggtggca gccctgagtc ctgcagacat caactacgat   1080
gagaccctta gcacgctgag gtatgctgac cgggccaagc agatccgctg caatgctgtc   1140
atcaatgagg accccaacaa caagctgatc cgcgagctga aggatgaggt gacccggctg   1200
cgggaccttc tgtacgccca gggtcttggc gacatcactg acatgaccaa tgccctggtg   1260
ggtatgagcc cctcatcctc gctctcagcc ctgtccagcc gcgcggcctc cgtgtccagc   1320
ctccacgagc gcatcttgtt tgccccgggc agcgaggagg ccattgaaag actgaaggaa   1380
acagagaaga tcatagctga gctcaatgag acctgggagg agaagctgcg gcggacagaa   1440
gccatccgga tggagaggga agccctgctg gccgagatgg gtgtggccat gagggaggat   1500
ggcggcacct tgggcgtatt ctctcccaaa aagacaccac acctcgtcaa cctgaacgag   1560
gacccgctga tgtctgagtg cctgctctac tacatcaagg atgggatcac cagagtgggc   1620
agggaggatg gcgagaggcg gcaggacatt gttctgagtg ggcacttcat caaggaggag   1680
cactgcgtct tccggagcga ctccagggga ggcagcgaag ctgtggtgac cttggagccc   1740
tgtgaggggg cagacaccta cgtcaatggc aagaaagtca cagagcccag catcctgcgt   1800
tcaggaaacc gcatcatcat gggtaagagc catgtgttcc ggttcaccca ccccgagcag   1860
gcccggcagg agcgtgagcg cacgccttgt gcggagacgc cagctgagcc tgtggactgg   1920
gccttcgccc agcgtgagct gctggagaag cagggcatcg acatgaagca ggagatggag   1980
cagaggctcc aggaactgga ggaccagtac cgccgcgagc gggaggaggc cacctacctg   2040
ctggagcagc agcggctgga ctatgagagc aagctggagg ctctgcagaa gcagatggac   2100
tccaggtact acccggaggt gaacgaggag gaggaggagc ccgaggatga agtccagtgg   2160
acagagcggg agtgtgagct ggcgctctgg gccttccgga agtggaagtg gtaccagttc   2220
acgtctctgc gggacctgct gtggggcaac gccatcttcc tcaaggaggc caatgccatc   2280
agcgtggagc tgaaaaagaa ggtacaattc cagtttgtcc tcctgacgga cacactctac   2340
tcccctctgc cacccgacct gctgcccccca gaggccgcca aagaccgaga gaagcggccc   2400
ttcccccgca ccattgtggc cgtggaggtc caggaccaga agaacggggc cacccactac   2460
tggacgctgg agaagctcag gcagcgtctg gacctgatgc gggagatgta cgaccgcgct   2520
gcagaggtgc cctccagtgt catcgaggac tgtgacaacg tggtgaccgg cggagacccc   2580
ttctatgacc gcttccccctg gttccggctg gtgggcaggg ccttcgtgta cctgagcaac   2640
ctgctgtacc ccgttcccct ggtacaccgt gtggcaatcg tcagcgagaa gggcgaggtg   2700
aagggcttcc tccgcgtggc cgtccaggcc atctcagccg atgaagaggc ccctgattat   2760
ggctctggcg tccgccagtc gggaactgct aaaatctcct ttgatgacca gcattttgaa   2820
aagttccagt ccgagtcttg ccccgtggtg gggatgtccc gctcgggaac ctcccaggaa   2880
gagcttcgca tcgtggaggg ccagggccag ggtgcagacg tggggccctc agccgatgaa   2940
gtcaacaaca acacctgttc agcagtgccc ccagaaggcc tcctcctaga cagctctgag   3000
aaagccgccc tggatgggcc cctggatgct gccctggacc acctccgcct gggcaacacc   3060
ttcaccttcc gtgtgacagt cctgcaggcg tccagcatct ctgccgaata tgccgacatc   3120
ttctgccagt tcaacttcat ccaccgccac gacgaggcct tctccacaga gcccctgaag   3180
aacacaggca gaggcccccc acttggcttc taccacgtcc agaacatcgc agtggaggtg   3240
```

-continued

```
accaagtcct tcattgagta catcaagagc cagcccattg ttttcgaggt ctttggccac   3300
taccagcagc acccgttccc gcccctctgc aaggacgtgc tcagcccccct gaggccctcg   3360
cgccgccact tccctcgggt catgccactg tccaagccag tgcccgccac caagctcagc   3420
acactgacgc ggccctgtcc gggaccctgc cactgcaagt acgacctgct ggtctacttc   3480
gagatctgtg agctggaggc caacggcgat tacatcccgg ccgtggtgga ccaccgtggg   3540
ggcatgccat gcatggggac cttcctcctc caccagggca tccagcgacg gattacggtg   3600
acactactgc atgagacagg cagccatatc cgctggaagg aagtgcgcga gctggtcgtg   3660
ggccgcatcc gaaacactcc agagaccgac gagtccctga tcgaccccaa catcttgtct   3720
ctcaacatcc tctctgccgg atacatccac ccagcccatg atgaccggac cttttaccaa   3780
tttgaggctg cgtggaacag ctccatgcac aactctctcc tgctgaaccg gatcacccct   3840
tatcgagaga aaatctacat gacactctcc gcttatatcg agatggagaa ctgcacccag   3900
ccggctgttg tcaccaagga cttctgcatg gtcttctatt cccgtgatgc caagctgcca   3960
gcctcgcgct ccatccgcaa cctctttggc agtgggagcc ttcgggcctc agagagtaac   4020
cgtgtgactg gtgtgtacga gctcagcctg tgccacgtgg ctgacgcggg cagcccaggg   4080
atgcagcgcc ggcgccgacg agtcctggac acatctgtgg cctatgtccg gggcgaggag   4140
aacctggcag gctggaggcc ccggagtgac agtctcattc tggaccacca gtgggagctg   4200
gagaagctga gcctcctgca ggaggtggag aagactaggc actacctgct cctgcgggag   4260
aagctggaga ccgcccagcg gcctgtcccg gaggcactgt ccccggcctt cagcgaggac   4320
tctgagtccc atggctcctc cagcgcctcc tccccgctct cggctgaggg ccgcccatca   4380
cccctggagg ctcccaacga gaggcagcgg gagctggccg tcaagtgctt gcgcctgctc   4440
acgcacacat tcaacagaga gtacacacac agccacgtct gcgtcagtgc cagcgagagc   4500
aagctctccg agatgtctgt caccctgctc cgggacccgt cgatgtcccc tctaggggtg   4560
gccactctca ccccctcctc cacttgcccc tctctggttg aagggcggta cggtgccact   4620
gacctgagga ccccgcagcc ctgctcccgg ccagccagcc cagagcccga gctgctgcca   4680
gaggccgact ccaagaagct cccttcccct gcccgggcaa cagagacaga caaggagccc   4740
cagcgcctgc tggtccctga catccaggag atccgagtca gcccgatcgt ttccaagaag   4800
gggtacctgc acttcctgga gccgcacacg tcaggctggg ccaggcgctt cgtggtggtg   4860
cggcgcccct atgcctacat gtacaacagc gacaaggaca ccgtggagcg gttcgtgctc   4920
aacctggcca ctgcccaggt ggagtacagt gaggaccagc aggctatgct caagacaccc   4980
aacacattcg cggtgtgcac ggaacaccgc ggcatcctgc tgcaggccgc cagcgacaag   5040
gacatgcatg actggctgta cgccttcaac cccctcctgg ccgggaccat acggtccaag   5100
ctctccagaa ggaggtctgc ccagatgcgg gtctgaacct gagccctccc gtgacagccg   5160
gcaggcccag cccatcccct ccctcatcct cgtctgtcct gtcacctgcc gcccagcccc   5220
tctcctgcca gacagcccac gaccgggtcg accccccagg ggacgcccat gccaggcccg   5280
gggacctgtg ccacacgacc agctgtgctc ccagcagagg ctgtgcgtgt cagttcttct   5340
tgcagaatgt gctctggtgg aacaagttgg gagaggctgg gggggccaag ggcacaggtt   5400
acgggggttc ttgctgccgt tctaatattt ttttaagcat agacagactt ataattaata   5460
tacgttagtt agtgacattg aaacagtcaa ctcggaaatt aactataaga cttgttctat   5520
ttataagtat ttatttctaa tgcctccaca tagccctgta atattcagat ggaaccccca   5580
```

-continued

```
accacctcca ccctgtttgt tcccacatgt gtctcccaag cctgctaggg acaggcaggg   5640

cagggacagc caccttggaa ggccgcagtg aggagctgtc tggaccagtg gggcaccttg   5700

gggctagcac acgggtgtat cgcctgggcc ccaggcttct ccatggccac atgggtcctg   5760

ggtgtatgtg tgggagagtg ggggggtgtc tttggtgcct gaagtctgcg cggcatggag   5820

ggtggtgtga gttcctctgg tgggagggag aacgcacatc tcttctgggc ggccacctga   5880

ggagtgactc caagaagagt tccggcagct ttccccagga aagggtgagg ggtgacactc   5940

ggctctggct ctgagatgag gcagacggca cccaggctgt gatctgtcct gggcggggac   6000

caggagggag cggggtcggg atcacctgcc agtgtgcaga ctctgggact gcgtgctgtc   6060

tccggaccat cagggtaggg tggtgggttg agaccaggaa gtcagggaag atcggaattc   6120

agggcgacgg tctaggtgtc gagggctgtg gcgcagcctc ttcagctgcg gcgagaaatg   6180

gagtgagtca aggtagcttc tgggaagaaa tgctgccatt agcaggtttc ttgcaaagac   6240

tttcctctct ttgttcccag ggcagagagt ttctgtgagt cccactgaga aaatcccatg   6300

gggtgggggt atcctggtcg gtcggcaatg gagggtggct ggcttggtgg ttattgtctt   6360

caaggagctc tttgctgctg catctgcggt gtccctttgt tcttgtccca tttcaccccc   6420

tctgcagaca ccaatgtccg agggccaccc aggacaggac gggggtcagc cccaagctga   6480

gagtctggtc ataggagtca tgtccagagg cctagggagg ttttagggcc ctccccaccc   6540

acacccacag gtcgatttgg tctcttttta gctcaaggaa agacagtagc caagcaacag   6600

agcccctctc ccgccgtggc ccgtgggagc agttacatcg ggtctggtgc tccagaccta   6660

gggcccagca ctttcatcag atcctgcctc ctggagtggg ggaaacgcag caccccactg   6720

gttctgaggc ccctaccctc ccaggctgtc ccacgtgatg ctgacatgag cctcagagac   6780

cccaatccca tgcctggggg tccctgagtg gcaaaacatc ctacagtgga tagtcataca   6840

caacaaaaga taatcctgct caaaatgcca acagtgttcc cattgagaaa cactgaatta   6900

ctgatccttc acaggtcagt tcaaatcata cttgtcttta gaaacagttc tttatgttaa   6960

ccctaagccc gg                                                       6972
```

<210> SEQ ID NO 39
<211> LENGTH: 1690
<212> TYPE: PRT
<213> ORGANISM: Human

<400> SEQUENCE: 39

```
Met Ala Gly Ala Ser Val Lys Val Ala Val Arg Val Arg Pro Phe Asn
 1               5                  10                  15

Ser Arg Glu Met Ser Arg Asp Ser Lys Cys Ile Ile Gln Met Ser Gly
            20                  25                  30

Ser Thr Thr Thr Ile Val Asn Pro Lys Gln Pro Lys Glu Thr Pro Lys
        35                  40                  45

Ser Phe Ser Phe Asp Tyr Ser Tyr Trp Ser His Thr Ser Pro Glu Asp
    50                  55                  60

Ile Asn Tyr Ala Ser Gln Lys Gln Val Tyr Arg Asp Ile Gly Glu Glu
65                  70                  75                  80

Met Leu Gln His Ala Phe Glu Gly Tyr Asn Val Cys Ile Phe Ala Tyr
                85                  90                  95

Gly Gln Thr Gly Ala Gly Lys Ser Tyr Thr Met Met Gly Lys Gln Glu
            100                 105                 110

Lys Asp Gln Gln Gly Ile Ile Pro Gln Leu Cys Glu Asp Leu Phe Ser
        115                 120                 125
```

-continued

```
Arg Ile Asn Asp Thr Thr Asn Asp Asn Met Ser Tyr Ser Val Glu Val
    130                 135                 140

Ser Tyr Met Glu Ile Tyr Cys Glu Arg Val Arg Asp Leu Leu Asn Pro
145                 150                 155                 160

Lys Asn Lys Gly Asn Leu Arg Val Arg Glu His Pro Leu Leu Gly Pro
                165                 170                 175

Tyr Val Glu Asp Leu Ser Lys Leu Ala Val Thr Ser Tyr Asn Asp Ile
            180                 185                 190

Gln Asp Leu Met Asp Ser Gly Asn Lys Ala Arg Thr Val Ala Ala Thr
        195                 200                 205

Asn Met Asn Glu Thr Ser Ser Arg Ser His Ala Val Phe Asn Ile Ile
    210                 215                 220

Phe Thr Gln Lys Arg His Asp Ala Glu Thr Asn Ile Thr Thr Glu Lys
225                 230                 235                 240

Val Ser Lys Ile Ser Leu Val Asp Leu Ala Gly Ser Glu Arg Ala Asp
                245                 250                 255

Ser Thr Gly Ala Lys Gly Thr Arg Leu Lys Glu Gly Ala Asn Ile Asn
            260                 265                 270

Lys Ser Leu Thr Thr Leu Gly Lys Val Ile Ser Ala Leu Ala Glu Met
        275                 280                 285

Asp Ser Gly Pro Asn Lys Asn Lys Lys Lys Lys Lys Thr Asp Phe Ile
    290                 295                 300

Pro Tyr Arg Asp Ser Val Leu Thr Trp Leu Leu Arg Glu Asn Leu Gly
305                 310                 315                 320

Gly Asn Ser Arg Thr Ala Met Val Ala Ala Leu Ser Pro Ala Asp Ile
                325                 330                 335

Asn Tyr Asp Glu Thr Leu Ser Thr Leu Arg Tyr Ala Asp Arg Ala Lys
            340                 345                 350

Gln Ile Arg Cys Asn Ala Val Ile Asn Glu Asp Pro Asn Asn Lys Leu
        355                 360                 365

Ile Arg Glu Leu Lys Asp Glu Val Thr Arg Leu Arg Asp Leu Leu Tyr
    370                 375                 380

Ala Gln Gly Leu Gly Asp Ile Thr Asp Met Thr Asn Ala Leu Val Gly
385                 390                 395                 400

Met Ser Pro Ser Ser Ser Leu Ser Ala Leu Ser Ser Arg Ala Ala Ser
                405                 410                 415

Val Ser Ser Leu His Glu Arg Ile Leu Phe Ala Pro Gly Ser Glu Glu
            420                 425                 430

Ala Ile Glu Arg Leu Lys Glu Thr Glu Lys Ile Ile Ala Glu Leu Asn
        435                 440                 445

Glu Thr Trp Glu Glu Lys Leu Arg Arg Thr Glu Ala Ile Arg Met Glu
    450                 455                 460

Arg Glu Ala Leu Leu Ala Glu Met Gly Val Ala Met Arg Glu Asp Gly
465                 470                 475                 480

Gly Thr Leu Gly Val Phe Ser Pro Lys Lys Thr Pro His Leu Val Asn
                485                 490                 495

Leu Asn Glu Asp Pro Leu Met Ser Glu Cys Leu Leu Tyr Tyr Ile Lys
            500                 505                 510

Asp Gly Ile Thr Arg Val Gly Arg Glu Asp Gly Glu Arg Arg Gln Asp
        515                 520                 525

Ile Val Leu Ser Gly His Phe Ile Lys Glu Glu His Cys Val Phe Arg
    530                 535                 540
```

-continued

```
Ser Asp Ser Arg Gly Gly Ser Glu Ala Val Val Thr Leu Glu Pro Cys
545                 550                 555                 560

Glu Gly Ala Asp Thr Tyr Val Asn Gly Lys Lys Val Thr Glu Pro Ser
                565                 570                 575

Ile Leu Arg Ser Gly Asn Arg Ile Ile Met Gly Lys Ser His Val Phe
            580                 585                 590

Arg Phe Thr His Pro Glu Gln Ala Arg Gln Glu Arg Glu Arg Thr Pro
        595                 600                 605

Cys Ala Glu Thr Pro Ala Glu Pro Val Asp Trp Ala Phe Ala Gln Arg
    610                 615                 620

Glu Leu Leu Glu Lys Gln Gly Ile Asp Met Lys Gln Glu Met Glu Gln
625                 630                 635                 640

Arg Leu Gln Glu Leu Glu Asp Gln Tyr Arg Arg Glu Arg Glu Glu Ala
                645                 650                 655

Thr Tyr Leu Leu Glu Gln Gln Arg Leu Asp Tyr Glu Ser Lys Leu Glu
            660                 665                 670

Ala Leu Gln Lys Gln Met Asp Ser Arg Tyr Tyr Pro Glu Val Asn Glu
        675                 680                 685

Glu Glu Glu Glu Pro Glu Asp Glu Val Gln Trp Thr Glu Arg Glu Cys
    690                 695                 700

Glu Leu Ala Leu Trp Ala Phe Arg Lys Trp Lys Trp Tyr Gln Phe Thr
705                 710                 715                 720

Ser Leu Arg Asp Leu Leu Trp Gly Asn Ala Ile Phe Leu Lys Glu Ala
                725                 730                 735

Asn Ala Ile Ser Val Glu Leu Lys Lys Lys Val Gln Phe Gln Phe Val
            740                 745                 750

Leu Leu Thr Asp Thr Leu Tyr Ser Pro Leu Pro Pro Asp Leu Leu Pro
        755                 760                 765

Pro Glu Ala Ala Lys Asp Arg Glu Lys Arg Pro Phe Pro Arg Thr Ile
    770                 775                 780

Val Ala Val Glu Val Gln Asp Gln Lys Asn Gly Ala Thr His Tyr Trp
785                 790                 795                 800

Thr Leu Glu Lys Leu Arg Gln Arg Leu Asp Leu Met Arg Glu Met Tyr
                805                 810                 815

Asp Arg Ala Ala Glu Val Pro Ser Ser Val Ile Glu Asp Cys Asp Asn
            820                 825                 830

Val Val Thr Gly Gly Asp Pro Phe Tyr Asp Arg Phe Pro Trp Phe Arg
        835                 840                 845

Leu Val Gly Arg Ala Phe Val Tyr Leu Ser Asn Leu Leu Tyr Pro Val
    850                 855                 860

Pro Leu Val His Arg Val Ala Ile Val Ser Glu Lys Gly Glu Val Lys
865                 870                 875                 880

Gly Phe Leu Arg Val Ala Val Gln Ala Ile Ser Ala Asp Glu Glu Ala
                885                 890                 895

Pro Asp Tyr Gly Ser Gly Val Arg Gln Ser Gly Thr Ala Lys Ile Ser
            900                 905                 910

Phe Asp Asp Gln His Phe Glu Lys Phe Gln Ser Glu Ser Cys Pro Val
        915                 920                 925

Val Gly Met Ser Arg Ser Gly Thr Ser Gln Glu Glu Leu Arg Ile Val
    930                 935                 940

Glu Gly Gln Gly Gln Gly Ala Asp Val Gly Pro Ser Ala Asp Glu Val
945                 950                 955                 960

Asn Asn Asn Thr Cys Ser Ala Val Pro Pro Glu Gly Leu Leu Leu Asp
```

-continued

```
                965                 970                 975

Ser Ser Glu Lys Ala Ala Leu Asp Gly Pro Leu Asp Ala Ala Leu Asp
            980                 985                 990

His Leu Arg Leu Gly Asn Thr Phe Thr Phe Arg Val Thr Val Leu Gln
        995                 1000                1005

Ala Ser Ser Ile Ser Ala Glu Tyr Ala Asp Ile Phe Cys Gln Phe Asn
    1010                1015                1020

Phe Ile His Arg His Asp Glu Ala Phe Ser Thr Glu Pro Leu Lys Asn
1025                1030                1035                1040

Thr Gly Arg Gly Pro Pro Leu Gly Phe Tyr His Val Gln Asn Ile Ala
                1045                1050                1055

Val Glu Val Thr Lys Ser Phe Ile Glu Tyr Ile Lys Ser Gln Pro Ile
            1060                1065                1070

Val Phe Glu Val Phe Gly His Tyr Gln Gln His Pro Phe Pro Pro Leu
        1075                1080                1085

Cys Lys Asp Val Leu Ser Pro Leu Arg Pro Ser Arg Arg His Phe Pro
    1090                1095                1100

Arg Val Met Pro Leu Ser Lys Pro Val Pro Ala Thr Lys Leu Ser Thr
1105                1110                1115                1120

Leu Thr Arg Pro Cys Pro Gly Pro Cys His Cys Lys Tyr Asp Leu Leu
                1125                1130                1135

Val Tyr Phe Glu Ile Cys Glu Leu Glu Ala Asn Gly Asp Tyr Ile Pro
            1140                1145                1150

Ala Val Val Asp His Arg Gly Gly Met Pro Cys Met Gly Thr Phe Leu
        1155                1160                1165

Leu His Gln Gly Ile Gln Arg Arg Ile Thr Val Thr Leu Leu His Glu
    1170                1175                1180

Thr Gly Ser His Ile Arg Trp Lys Glu Val Arg Glu Leu Val Val Gly
1185                1190                1195                1200

Arg Ile Arg Asn Thr Pro Glu Thr Asp Glu Ser Leu Ile Asp Pro Asn
                1205                1210                1215

Ile Leu Ser Leu Asn Ile Leu Ser Ala Gly Tyr Ile His Pro Ala His
            1220                1225                1230

Asp Asp Arg Thr Phe Tyr Gln Phe Glu Ala Ala Trp Asn Ser Ser Met
        1235                1240                1245

His Asn Ser Leu Leu Leu Asn Arg Ile Thr Pro Tyr Arg Glu Lys Ile
    1250                1255                1260

Tyr Met Thr Leu Ser Ala Tyr Ile Glu Met Glu Asn Cys Thr Gln Pro
1265                1270                1275                1280

Ala Val Val Thr Lys Asp Phe Cys Met Val Phe Tyr Ser Arg Asp Ala
                1285                1290                1295

Lys Leu Pro Ala Ser Arg Ser Ile Arg Asn Leu Phe Gly Ser Gly Ser
            1300                1305                1310

Leu Arg Ala Ser Glu Ser Asn Arg Val Thr Gly Val Tyr Glu Leu Ser
        1315                1320                1325

Leu Cys His Val Ala Asp Ala Gly Ser Pro Gly Met Gln Arg Arg Arg
    1330                1335                1340

Arg Arg Val Leu Asp Thr Ser Val Ala Tyr Val Arg Gly Glu Glu Asn
1345                1350                1355                1360

Leu Ala Gly Trp Arg Pro Arg Ser Asp Ser Leu Ile Leu Asp His Gln
                1365                1370                1375

Trp Glu Leu Glu Lys Leu Ser Leu Leu Gln Glu Val Glu Lys Thr Arg
            1380                1385                1390
```

```
His Tyr Leu Leu Leu Arg Glu Lys Leu Glu Thr Ala Gln Arg Pro Val
        1395                1400                1405

Pro Glu Ala Leu Ser Pro Ala Phe Ser Glu Asp Ser Glu Ser His Gly
    1410                1415                1420

Ser Ser Ser Ala Ser Ser Pro Leu Ser Ala Glu Gly Arg Pro Ser Pro
1425                1430                1435                1440

Leu Glu Ala Pro Asn Glu Arg Gln Arg Glu Leu Ala Val Lys Cys Leu
                1445                1450                1455

Arg Leu Leu Thr His Thr Phe Asn Arg Glu Tyr Thr His Ser His Val
            1460                1465                1470

Cys Val Ser Ala Ser Glu Ser Lys Leu Ser Glu Met Ser Val Thr Leu
        1475                1480                1485

Leu Arg Asp Pro Ser Met Ser Pro Leu Gly Val Ala Thr Leu Thr Pro
    1490                1495                1500

Ser Ser Thr Cys Pro Ser Leu Val Glu Gly Arg Tyr Gly Ala Thr Asp
1505                1510                1515                1520

Leu Arg Thr Pro Gln Pro Cys Ser Arg Pro Ala Ser Pro Glu Pro Glu
                1525                1530                1535

Leu Leu Pro Glu Ala Asp Ser Lys Lys Leu Pro Ser Pro Ala Arg Ala
            1540                1545                1550

Thr Glu Thr Asp Lys Glu Pro Gln Arg Leu Leu Val Pro Asp Ile Gln
        1555                1560                1565

Glu Ile Arg Val Ser Pro Ile Val Ser Lys Lys Gly Tyr Leu His Phe
    1570                1575                1580

Leu Glu Pro His Thr Ser Gly Trp Ala Arg Arg Phe Val Val Val Arg
1585                1590                1595                1600

Arg Pro Tyr Ala Tyr Met Tyr Asn Ser Asp Lys Asp Thr Val Glu Arg
                1605                1610                1615

Phe Val Leu Asn Leu Ala Thr Ala Gln Val Glu Tyr Ser Glu Asp Gln
            1620                1625                1630

Gln Ala Met Leu Lys Thr Pro Asn Thr Phe Ala Val Cys Thr Glu His
        1635                1640                1645

Arg Gly Ile Leu Leu Gln Ala Ala Ser Asp Lys Asp Met His Asp Trp
    1650                1655                1660

Leu Tyr Ala Phe Asn Pro Leu Leu Ala Gly Thr Ile Arg Ser Lys Leu
1665                1670                1675                1680

Ser Arg Arg Arg Ser Ala Gln Met Arg Val
                1685                1690
```

```
<210> SEQ ID NO 40
<211> LENGTH: 42
<212> TYPE: DNA
<213> ORGANISM: Artificial Sequence
<220> FEATURE:
<223> OTHER INFORMATION: Sense oligo for pET23dmyc

<400> SEQUENCE: 40

tcgagggtac cgagcagaag ctgatcagcg aggaggacct ga                         42


<210> SEQ ID NO 41
<211> LENGTH: 42
<212> TYPE: DNA
<213> ORGANISM: Artificial Sequence
<220> FEATURE:
<223> OTHER INFORMATION: Antisense oligo for pET23dmyc

<400> SEQUENCE: 41
```

tcgatcaggt cctcctcgct gatcagcttc tgctcggtac cc 42

<210> SEQ ID NO 42
<211> LENGTH: 27
<212> TYPE: DNA
<213> ORGANISM: Artificial Sequence
<220> FEATURE:
<223> OTHER INFORMATION: K335 5' primer

<400> SEQUENCE: 42
tagccatgga agaggtgaag ggaattc 27

<210> SEQ ID NO 43
<211> LENGTH: 24
<212> TYPE: DNA
<213> ORGANISM: Artificial Sequence
<220> FEATURE:
<223> OTHER INFORMATION: K335 3' primer

<400> SEQUENCE: 43
ccgctcgagt tttcttgctc tgtc 24

<210> SEQ ID NO 44
<211> LENGTH: 24
<212> TYPE: DNA
<213> ORGANISM: Artificial Sequence
<220> FEATURE:
<223> OTHER INFORMATION: Q475 5' primer

<400> SEQUENCE: 44
tagaagcttg gaagaggtga aggg 24

<210> SEQ ID NO 45
<211> LENGTH: 24
<212> TYPE: DNA
<213> ORGANISM: Artificial Sequence
<220> FEATURE:
<223> OTHER INFORMATION: Q475 3' primer

<400> SEQUENCE: 45
tagaagcttc tgggtaatca attg 24

<210> SEQ ID NO 46
<211> LENGTH: 24
<212> TYPE: DNA
<213> ORGANISM: Artificial Sequence
<220> FEATURE:
<223> OTHER INFORMATION: D679 5' primer

<400> SEQUENCE: 46
tagaagcttg gaagaggtga aggg 24

<210> SEQ ID NO 47
<211> LENGTH: 25
<212> TYPE: DNA
<213> ORGANISM: Artificial Sequence
<220> FEATURE:
<223> OTHER INFORMATION: D679 3' primer

<400> SEQUENCE: 47
tagaagcttg tctcgttctt ttaac 25

<210> SEQ ID NO 48
<211> LENGTH: 24
<212> TYPE: DNA

-continued

<213> ORGANISM: Artificial Sequence
<220> FEATURE:
<223> OTHER INFORMATION: FL1 5' primer

<400> SEQUENCE: 48
tagaagcttg gaagaggtga aggg 24

<210> SEQ ID NO 49
<211> LENGTH: 25
<212> TYPE: DNA
<213> ORGANISM: Artificial Sequence
<220> FEATURE:
<223> OTHER INFORMATION: FL1 3' primer

<400> SEQUENCE: 49
tagaagcttg tgggcctctt cttcg 25

<210> SEQ ID NO 50
<211> LENGTH: 26
<212> TYPE: DNA
<213> ORGANISM: Artificial Sequence
<220> FEATURE:
<223> OTHER INFORMATION: P166 5' primer

<400> SEQUENCE: 50
tacggatccc aaattatgaa attatg 26

<210> SEQ ID NO 51
<211> LENGTH: 28
<212> TYPE: DNA
<213> ORGANISM: Artificial Sequence
<220> FEATURE:
<223> OTHER INFORMATION: P166 3' primer

<400> SEQUENCE: 51
tacaagctta gcagttggat ctacagtc 28

<210> SEQ ID NO 52
<211> LENGTH: 27
<212> TYPE: DNA
<213> ORGANISM: Artificial Sequence
<220> FEATURE:
<223> OTHER INFORMATION: H195 5' primer

<400> SEQUENCE: 52
tacggatcca taggatatgt gtgtgtg 27

<210> SEQ ID NO 53
<211> LENGTH: 28
<212> TYPE: DNA
<213> ORGANISM: Artificial Sequence
<220> FEATURE:
<223> OTHER INFORMATION: H195 3' primer

<400> SEQUENCE: 53
tacaagctta gcagttggat ctacagtc 28

<210> SEQ ID NO 54
<211> LENGTH: 32
<212> TYPE: DNA
<213> ORGANISM: Artificial Sequence
<220> FEATURE:
<223> OTHER INFORMATION: FL2 5' primer

<400> SEQUENCE: 54
ctccatggta acatctttaa atgaagataa tg 32

<210> SEQ ID NO 55
<211> LENGTH: 33
<212> TYPE: DNA
<213> ORGANISM: Artificial Sequence
<220> FEATURE:
<223> OTHER INFORMATION: FL2 3' primer

<400> SEQUENCE: 55
ctaagcttaa gggcacgggg tctcttcggg ttg 33

<210> SEQ ID NO 56
<211> LENGTH: 33
<212> TYPE: DNA
<213> ORGANISM: Artificial Sequence
<220> FEATURE:
<223> OTHER INFORMATION: E433 5' primer

<400> SEQUENCE: 56
atccatggcg agagctaaga caccccggaa acc 33

<210> SEQ ID NO 57
<211> LENGTH: 35
<212> TYPE: DNA
<213> ORGANISM: Artificial Sequence
<220> FEATURE:
<223> OTHER INFORMATION: E433 3' primer

<400> SEQUENCE: 57
atgcggccgc ttcttgagtc acttccgcaa atctc 35

<210> SEQ ID NO 58
<211> LENGTH: 33
<212> TYPE: DNA
<213> ORGANISM: Artificial Sequence
<220> FEATURE:
<223> OTHER INFORMATION: R494 5' primer

<400> SEQUENCE: 58
atccatggcg agagctaaga caccccggaa acc 33

<210> SEQ ID NO 59
<211> LENGTH: 35
<212> TYPE: DNA
<213> ORGANISM: Artificial Sequence
<220> FEATURE:
<223> OTHER INFORMATION: R494 3' primer

<400> SEQUENCE: 59
atgcggccgc ccttggaagt gtctgctcat cgttg 35

<210> SEQ ID NO 60
<211> LENGTH: 33
<212> TYPE: DNA
<213> ORGANISM: Artificial Sequence
<220> FEATURE:
<223> OTHER INFORMATION: E658 5' primer

<400> SEQUENCE: 60
atccatggcg agagctaaga caccccggaa acc 33

<210> SEQ ID NO 61
<211> LENGTH: 34
<212> TYPE: DNA
<213> ORGANISM: Artificial Sequence
<220> FEATURE:

-continued

<223> OTHER INFORMATION: E658 3' primer

<400> SEQUENCE: 61
atgcggccgc ttcagtaaca atagccttca gttg 34

<210> SEQ ID NO 62
<211> LENGTH: 31
<212> TYPE: DNA
<213> ORGANISM: Artificial Sequence
<220> FEATURE:
<223> OTHER INFORMATION: L360 5' primer

<400> SEQUENCE: 62
atccatggcg tgccagccaa attcgtctgc g 31

<210> SEQ ID NO 63
<211> LENGTH: 32
<212> TYPE: DNA
<213> ORGANISM: Artificial Sequence
<220> FEATURE:
<223> OTHER INFORMATION: L360 3' primer

<400> SEQUENCE: 63
atctcgagca atatgttctt tgctctatga gc 32

<210> SEQ ID NO 64
<211> LENGTH: 31
<212> TYPE: DNA
<213> ORGANISM: Artificial Sequence
<220> FEATURE:
<223> OTHER INFORMATION: K491 5' primer

<400> SEQUENCE: 64
atccatggcg tgccagccaa attcgtctgc g 31

<210> SEQ ID NO 65
<211> LENGTH: 32
<212> TYPE: DNA
<213> ORGANISM: Artificial Sequence
<220> FEATURE:
<223> OTHER INFORMATION: K491 3' primer

<400> SEQUENCE: 65
atctcgagtt tctcctcagt actttccaaa gc 32

<210> SEQ ID NO 66
<211> LENGTH: 31
<212> TYPE: DNA
<213> ORGANISM: Artificial Sequence
<220> FEATURE:
<223> OTHER INFORMATION: S553 5' primer

<400> SEQUENCE: 66
atccatggcg tgccagccaa attcgtctgc g 31

<210> SEQ ID NO 67
<211> LENGTH: 33
<212> TYPE: DNA
<213> ORGANISM: Artificial Sequence
<220> FEATURE:
<223> OTHER INFORMATION: S553 3' primer

<400> SEQUENCE: 67
atctcgaggc tgccatcctt aattaattct tcc 33

<210> SEQ ID NO 68
<211> LENGTH: 31
<212> TYPE: DNA
<213> ORGANISM: Artificial Sequence
<220> FEATURE:
<223> OTHER INFORMATION: M329 5' primer

<400> SEQUENCE: 68
ctggatcccg gcggaggaag gagccgtggc c 31

<210> SEQ ID NO 69
<211> LENGTH: 29
<212> TYPE: DNA
<213> ORGANISM: Artificial Sequence
<220> FEATURE:
<223> OTHER INFORMATION: M329 3' primer

<400> SEQUENCE: 69
cactcgagca tatatttagc agtactggc 29

<210> SEQ ID NO 70
<211> LENGTH: 31
<212> TYPE: DNA
<213> ORGANISM: Artificial Sequence
<220> FEATURE:
<223> OTHER INFORMATION: T340 5' primer

<400> SEQUENCE: 70
ctggatcccg gcggaggaag gagccgtggc c 31

<210> SEQ ID NO 71
<211> LENGTH: 34
<212> TYPE: DNA
<213> ORGANISM: Artificial Sequence
<220> FEATURE:
<223> OTHER INFORMATION: T340 3' primer

<400> SEQUENCE: 71
cactcgagag ttgatacctc attaacataa ggag 34

<210> SEQ ID NO 72
<211> LENGTH: 31
<212> TYPE: DNA
<213> ORGANISM: Artificial Sequence
<220> FEATURE:
<223> OTHER INFORMATION: S405 5' primer

<400> SEQUENCE: 72
ctggatcccg gcggaggaag gagccgtggc c 31

<210> SEQ ID NO 73
<211> LENGTH: 29
<212> TYPE: DNA
<213> ORGANISM: Artificial Sequence
<220> FEATURE:
<223> OTHER INFORMATION: S405 3' primer

<400> SEQUENCE: 73
cactcgagag aagaggtcac cagcatccg 29

<210> SEQ ID NO 74
<211> LENGTH: 31
<212> TYPE: DNA
<213> ORGANISM: Artificial Sequence
<220> FEATURE:
<223> OTHER INFORMATION: V465 5' primer

<400> SEQUENCE: 74
ctggatcccg gcggaggaag gagccgtggc c 31

<210> SEQ ID NO 75
<211> LENGTH: 29
<212> TYPE: DNA
<213> ORGANISM: Artificial Sequence
<220> FEATURE:
<223> OTHER INFORMATION: V465 3' primer

<400> SEQUENCE: 75
cactcgagga cagattcatc aatttctcg 29

<210> SEQ ID NO 76
<211> LENGTH: 31
<212> TYPE: DNA
<213> ORGANISM: Artificial Sequence
<220> FEATURE:
<223> OTHER INFORMATION: T488 5' primer

<400> SEQUENCE: 76
ctggatcccg gcggaggaag gagccgtggc c 31

<210> SEQ ID NO 77
<211> LENGTH: 30
<212> TYPE: DNA
<213> ORGANISM: Artificial Sequence
<220> FEATURE:
<223> OTHER INFORMATION: T488 3' primer

<400> SEQUENCE: 77
cactcgagtg ttgctggatt ccattctatc 30

<210> SEQ ID NO 78
<211> LENGTH: 31
<212> TYPE: DNA
<213> ORGANISM: Artificial Sequence
<220> FEATURE:
<223> OTHER INFORMATION: M1 5' primer

<400> SEQUENCE: 78
ctggatccgg aggaaatcat gtcttgtgaa g 31

<210> SEQ ID NO 79
<211> LENGTH: 30
<212> TYPE: DNA
<213> ORGANISM: Artificial Sequence
<220> FEATURE:
<223> OTHER INFORMATION: M1 3' primer

<400> SEQUENCE: 79
cactcgagtg gaatcagcgc cccgttagag 30

<210> SEQ ID NO 80
<211> LENGTH: 31
<212> TYPE: DNA
<213> ORGANISM: Artificial Sequence
<220> FEATURE:
<223> OTHER INFORMATION: M2 5' primer

<400> SEQUENCE: 80
ctggatccca aactgggaat ttgcccgaat g 31

<210> SEQ ID NO 81
<211> LENGTH: 30

<212> TYPE: DNA
<213> ORGANISM: Artificial Sequence
<220> FEATURE:
<223> OTHER INFORMATION: M2 3' primer

<400> SEQUENCE: 81
cactcgagtg gaatcagcgc cccgttagag 30

<210> SEQ ID NO 82
<211> LENGTH: 31
<212> TYPE: DNA
<213> ORGANISM: Artificial Sequence
<220> FEATURE:
<223> OTHER INFORMATION: M3 5' primer

<400> SEQUENCE: 82
ctggatccac agaatatgtg tctgtgttag g 31

<210> SEQ ID NO 83
<211> LENGTH: 30
<212> TYPE: DNA
<213> ORGANISM: Artificial Sequence
<220> FEATURE:
<223> OTHER INFORMATION: M3 3' primer

<400> SEQUENCE: 83
cactcgagtg gaatcagcgc cccgttagag 30

<210> SEQ ID NO 84
<211> LENGTH: 31
<212> TYPE: DNA
<213> ORGANISM: Artificial Sequence
<220> FEATURE:
<223> OTHER INFORMATION: M4 5' primer

<400> SEQUENCE: 84
ctggatccgg aggaaatcat gtcttgtgaa g 31

<210> SEQ ID NO 85
<211> LENGTH: 29
<212> TYPE: DNA
<213> ORGANISM: Artificial Sequence
<220> FEATURE:
<223> OTHER INFORMATION: M4 3' primer

<400> SEQUENCE: 85
cactcgagtg gtccttgctg tatgatctc 29

<210> SEQ ID NO 86
<211> LENGTH: 31
<212> TYPE: DNA
<213> ORGANISM: Artificial Sequence
<220> FEATURE:
<223> OTHER INFORMATION: M5 5' primer

<400> SEQUENCE: 86
ctggatccca aactgggaat ttgcccgaat g 31

<210> SEQ ID NO 87
<211> LENGTH: 29
<212> TYPE: DNA
<213> ORGANISM: Artificial Sequence
<220> FEATURE:
<223> OTHER INFORMATION: M5 3' primer

<400> SEQUENCE: 87

-continued cactcgagtg gtccttgctg tatgatctc 29

<210> SEQ ID NO 88
<211> LENGTH: 31
<212> TYPE: DNA
<213> ORGANISM: Artificial Sequence
<220> FEATURE:
<223> OTHER INFORMATION: M6 5' primer

<400> SEQUENCE: 88
ctggatccac agaatatgtg tctgtgttag g 31

<210> SEQ ID NO 89
<211> LENGTH: 29
<212> TYPE: DNA
<213> ORGANISM: Artificial Sequence
<220> FEATURE:
<223> OTHER INFORMATION: M6 3' primer

<400> SEQUENCE: 89
cactcgagtg gtccttgctg tatgatctc 29

<210> SEQ ID NO 90
<211> LENGTH: 28
<212> TYPE: DNA
<213> ORGANISM: Artificial Sequence
<220> FEATURE:
<223> OTHER INFORMATION: FL3 5' primer

<400> SEQUENCE: 90
ctccatggac tcgtcgcttc aggcccgc 28

<210> SEQ ID NO 91
<211> LENGTH: 35
<212> TYPE: DNA
<213> ORGANISM: Artificial Sequence
<220> FEATURE:
<223> OTHER INFORMATION: FL3 3' primer

<400> SEQUENCE: 91
ctctcgagct ggggccgttt cttgctgctt atttg 35

<210> SEQ ID NO 92
<211> LENGTH: 31
<212> TYPE: DNA
<213> ORGANISM: Artificial Sequence
<220> FEATURE:
<223> OTHER INFORMATION: A2N370 5' primer

<400> SEQUENCE: 92
ctggatccca gccgcgggcg gctcgacgca g 31

<210> SEQ ID NO 93
<211> LENGTH: 30
<212> TYPE: DNA
<213> ORGANISM: Artificial Sequence
<220> FEATURE:
<223> OTHER INFORMATION: A2N370 3' primer

<400> SEQUENCE: 93
cactcgagat tgatcacctc cttggacctg 30

<210> SEQ ID NO 94
<211> LENGTH: 31
<212> TYPE: DNA
<213> ORGANISM: Artificial Sequence -continued

```
<220> FEATURE:
<223> OTHER INFORMATION: A2M511 5' primer

<400> SEQUENCE: 94

ctggatccca gccgcgggcg gctcgacgca g                                    31


<210> SEQ ID NO 95
<211> LENGTH: 29
<212> TYPE: DNA
<213> ORGANISM: Artificial Sequence
<220> FEATURE:
<223> OTHER INFORMATION: A2M511 3' primer

<400> SEQUENCE: 95

cactcgagca ttgtgggaca atggttctc                                       29


<210> SEQ ID NO 96
<211> LENGTH: 26
<212> TYPE: DNA
<213> ORGANISM: Artificial Sequence
<220> FEATURE:
<223> OTHER INFORMATION: K519 5' primer

<400> SEQUENCE: 96

tcggatcctt ggtgcaagag cttcag                                          26


<210> SEQ ID NO 97
<211> LENGTH: 26
<212> TYPE: DNA
<213> ORGANISM: Artificial Sequence
<220> FEATURE:
<223> OTHER INFORMATION: K519 3' primer

<400> SEQUENCE: 97

cactcgagct tcctgttggc ctgagc                                          26


<210> SEQ ID NO 98
<211> LENGTH: 24
<212> TYPE: DNA
<213> ORGANISM: Artificial Sequence
<220> FEATURE:
<223> OTHER INFORMATION: E152.2 5' primer

<400> SEQUENCE: 98

catgccatgg aactcaaggg caac                                            24


<210> SEQ ID NO 99
<211> LENGTH: 26
<212> TYPE: DNA
<213> ORGANISM: Artificial Sequence
<220> FEATURE:
<223> OTHER INFORMATION: E152.2 3' primer

<400> SEQUENCE: 99

cactcgagct tcctgttggc ctgagc                                          26


<210> SEQ ID NO 100
<211> LENGTH: 31
<212> TYPE: DNA
<213> ORGANISM: Artificial Sequence
<220> FEATURE:
<223> OTHER INFORMATION: Q151.3 5' primer

<400> SEQUENCE: 100

ggatatccat atgcaggaac tcaagggcaa c                                    31
```

-continued

```
<210> SEQ ID NO 101
<211> LENGTH: 29
<212> TYPE: DNA
<213> ORGANISM: Artificial Sequence
<220> FEATURE:
<223> OTHER INFORMATION: Q151.3 3' primer

<400> SEQUENCE: 101

gcaggatcct cacttcctgt tggcctgag                                          29


<210> SEQ ID NO 102
<211> LENGTH: 31
<212> TYPE: DNA
<213> ORGANISM: Artificial Sequence
<220> FEATURE:
<223> OTHER INFORMATION: Q353 5' primer

<400> SEQUENCE: 102

ctggatcccc ggggcttcgg tgaaggtggc g                                       31


<210> SEQ ID NO 103
<211> LENGTH: 30
<212> TYPE: DNA
<213> ORGANISM: Artificial Sequence
<220> FEATURE:
<223> OTHER INFORMATION: Q353 3' primer

<400> SEQUENCE: 103

cactcgagct gcttggcccg gtcagcatac                                         30


<210> SEQ ID NO 104
<211> LENGTH: 31
<212> TYPE: DNA
<213> ORGANISM: Artificial Sequence
<220> FEATURE:
<223> OTHER INFORMATION: M472 5' primer

<400> SEQUENCE: 104

ctggatcccc ggggcttcgg tgaaggtggc g                                       31


<210> SEQ ID NO 105
<211> LENGTH: 29
<212> TYPE: DNA
<213> ORGANISM: Artificial Sequence
<220> FEATURE:
<223> OTHER INFORMATION: M472 3' primer

<400> SEQUENCE: 105

cactcgagca tctcggccag cagggcttc                                          29
```

HUMAN KINESINS AND METHODS OF PRODUCING AND PURIFYING HUMAN KINESINS

CROSS REFERENCE TO RELATED APPLICATIONS

The present invention is a continuation application of U.S. Ser. No. 09/295,612, filed Apr. 20, 1999 abandoned, which is incorporated herein by reference.

FIELD OF THE INVENTION

This invention relates to the production and purification of human kinesins, preferably functional, using prokaryotic systems and to human kinesins isolated from bacterial systems.

BACKGROUND OF THE INVENTION

Cancer is the second-leading cause of death in industrialized nations. Effective therapeutics include the taxanes and vinca alkyloids, agents which act on microtubules. Microtubules are the primary structural element of the mitotic spindle. The mitotic spindle is responsible for distribution of replicate copies of the genome to each of the two daughter cells that result from cell division. It is presumed that it is the disruption of the mitotic spindle by these drugs that results in inhibition of cancer cell division, and also induction of cancer cell death. However, microtubules also form other types of cellular structures, including tracks for intracellular transport in nerve processes. Therefore, the taxanes have side effects that limit their usefulness.

Mitotic kinesins are enzymes essential for assembly and function of the mitotic spindle, but are not generally part of other microtubule structures, such as nerve processes. Mitotic kinesins play essential roles during all phases of mitosis. These enzymes are "molecular motors" that translate energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest. From both the biological and enzymatic perspectives, these enzymes are attractive targets for the discovery and development of novel anti-mitotic chemotherapeutics.

A number of kinesins have been described in the art. However, there still exists a need for kinesins which can be easily produced in large quantities. In particular, human mitotic kinesins isolated and purified from a bacterial source are desirable.

Among the kinesins which have been identified is chromokinesin. Chromokinesin is a kinesin localized to mitotic chromatin and contributes to prometaphase chromosome alignment; it is expressed primarily in proliferating tissues and is enriched in mitotic compared to interphase cells. Perturbation of a Xenopus chromokinesin causes gross defects in mitotic spindle formation, including dissociation of chromosomes from spindle microtubules, multipolar spindles, misaligned chromosomes and failure of cytokinesis. Cloning of chicken (Wang and Adler, J. Cell Biol., 128:761–8 (1995)) and human (Oh, et al., direct GenBank submission without corresponding publication, submitted Jun. 11, 1998 by Molecular Biology, Institute for Medical Sciences, San5 Wonchon Paldal, Suwon, Kyongki 442–749, Korea) chromokinesin homologs have been reported. The mouse homolog of chromokinesin, Kif4, has been expressed in Sf9 cells (bacculovirus vector) and has been reported to have motility and ATPase activity (Sekine, et al., J. Cell Biol., 127–187–201 (1994)). This same study speculated that Kif4 may participate in the transport of membraneous organelles in neuronal and other cell types.

Another kinesin reported to be associated with chromosomes is Kid. Kid is reported as unrelated to other known kinesins. The C-terminal 260 amino acids of Kid expressed in bacteria and purified reportedly binds directly to DNA in vitro. The same study reported that when fused to a transcriptional activation domain and co-transfected into mammalian cells with a reporter construct this domain can stimulate expression from the promoter on the co-transfected construct in living cells. Tokai, et al., EMBO J., 15(3):457–467 (1996). This study further reports that the amino-terminal 470 amino acids of Kid, which includes the motor domain, has been expressed in bacteria fused to glutathione-S-transferase, binds to microtubues and exhibits microtubule-stimulated ATPase activity. Kid is expressed in all human cell lines that have been examined, and is most abundant in adult human speen, thymus and testis as well as fetal liver and kidney. In cultured human cells, Kid is reportedly found associated with chromatin throughout mitosis, showing some enrichment at kinetochores.

Another mitotic kinesin of interest is MKLP1 which localizes to microtubules of the spindle midzone throughout mitosis. In vitro MKLP1 can slide antiparallel microtubules relative to each other. Microinjection of antibody directed against MKLP1 into mammalian cells induces mitotic arrest with subtle defects in microtubule organization. Genetic data from both Drosophila and *C. elegans* clearly show that MKLP1 homologues are required for organization of the interzonal microtubules of the anaphase spindle and for formation of a functional contractile ring. MKLP1 associates with a kinase of the polo family in both Drosophila and mammals. Cloning of human (Nislow, et al., Nature, 359:543–7 (1992)), hamster (Kuriyama, et al., J. Cell Sci., 107(Pt 12):3485–99 (1994)), Drosophila (Adams, et al., Gene Dev., 12:1483–94 (1998)), and C. elegans (Raich, et al., Mol. Biol. Cell, 9:2037–49 (1998)) homologs of MKLP1 have been reported. Nislow, et al., supra, reported on expressed full-length human MKLP1 in bacteria, however there was relatively poor expression, and the polypeptide was not purified. Using this crude bacterial lysate, microtubule bundling and sliding activity were reported on. Kuriyama, et al., supra, reported on expressed hamster MKLP1 in Sf9 cells (baculovirus vector), but the protein was not purified.

KSP is also of interest. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibody directed against KSP into human cells prevents spindle pole separation during prometaphase, giving rise to monopolar spindles and causing mitotic arrest. KSP and related kinesins bundle antiparallel microtubules and slide them relative to one another, thus forcing the two spindle poles apart. KSP may also mediate in anaphase B spindle elongation and focussing of microtubules at the spindle pole. Cloning of human (Blangy, et al., Cell, 83:1159–69 (1995); Whitehead, et al., direct GenBank submission without corresponding publication, submitted September 29, 1995 by Medical Biochemistry, University of Calgary, 3330 Hospital Dr. NW, Calgary, Alberta TN 4N1, Canada), Drosophila (Heck, et al., J Cell Biol, 123:665–79 (1993)) and Xenopus (Le Guellec, et al., Mol. Cell Biol., 11(6):3395–8(1991)) homologs of KSP have been reported. Drosophila KLP61F/KRP130 has reportedly been purified in native form (Cole, et al., *J. Biol. Chem.*, 269(37):22913–6 (1994)), expressed in *E. coli*, (Barton, et al., Mol. Biol. Cell, 6:1563–74 (1995)) and reported to have motility and ATPase activities (Cole, et al., supra; Barton, et al., supra). Xenopus Eg5 was expressed in *E. coli* and reported to possess motility activity (Sawin, et al., Nature, 359:540–3 (1992); Lockhart and Cross, Biochemistry, 35(7):2365–73 (1996); Crevel, et al, J. Mol. Biol., 273:160–170 (1997) and ATPase activity (Lockhart and Cross, supra; Crevel et al., supra).

CENP-E, also of interest, is a plus end-directed microtubule motor essential for achieving metaphase chromosome alignment. CENP-E accumulates during interphase and is degraded following completion of mitosis. Microinjection of antibody directed against CENP-E or overexpression of a dominant negative mutant of CENP-E causes mitotic arrest with prometaphase chromosomes scattered on a bipolar spindle. The tail domain of CENP-E mediates localization to kinetochores and also interacts with the mitotic checkpoint kinase hBubR1. CENP-E also associates with active forms of MAP kinase. Cloning of human (Yen, et al., Nature, 359(6395):536–9 (1992)) CENP-E has been reported. In Thrower, et al., EMBO J., 14:918–26 (1995) partially purified native human CENP-E was reported on. Moreover, the study reported that CENP-E was a minus end-directed microtubule motor. Wood, et al., Cell, 91:357–66 (1997)) discloses expressed Xenopus CENP-E in *E. coli* and that XCENP-E has motility as a plus end directed motor in vitro.

The kinesin MCAK has also been identified. During anaphase A disjoined sister chromatids migrate poleward. This poleward movement is driven by kinetochores and is accompanied by the depolymerization of microtubules attached to the migrating chromatids. The kinesin MCAK plays an important role in this motility and may promote disassembly of microtubules attached to kinetochores. MCAK localizes to kinetochores of mitotic chromosomes. MCAK belongs to small and unique subfamily of kinesins (Kin I) that destabilize microtubule ends. Overexpression of a dominant negative MCAK mutant or antisense inhibition of MCAK expression causes chromosomes to lag during anaphase. Genes for the Xenopus (Walczak, et al., Cell, 84:37–47 (1996), hamster (Wordeman and Mitchison, J. Cell Biol., 128:95–104 (1995) and human (Kim, et al., Biochim. Biophys. Acta., 1359:181–6 (1997)) homologs of MCAK have been cloned and characterized. Kim, et al., supra, also described mRNA expression patterns of the endogenous gene in human cells and tissues, but did not describe exogenous expression.

Other mitotic kinesins of interest include HSET and Kif15. However, it is understood, as described above, all kinesins are of interest.

The kinesin superfamily further encompasses a number of families that exhibit non-mitotic motor functions, e.g., vesicle and organelle transport. These proteins are ATP dependent, and have plus end-directed microtubule motor activity involved in fast anterograde organelle transport in neurons. Anterograde transport is a directional transport, typically of mitochondria, other organelles and vesicles, from the cell body to the tip of the axon. Moreover, some non-mitotic kinesins are involved in "slow " transport.

Among the kinesins associated with neurons is the Kif2 family of kinesins. Cloning of mouse (Aizawa, et al., Genes Dev., 12:1483–94 (1992)), Xenopus (Walczak, et al., supra), and human (Debernardi, et al., Genomics, 42:67–73 (1997)) Kin2 homologs have been reported. Mouse Kif2 (Noda, et al., J. Cell iol., 129:157–67 (1995)) was reportedly expressed in Sf9 cells (bacculovirus vector) and was reported to have motility activity. Xenopus Kif2 (Desai, et al., Cell, 96:69–78 (1999)) was expressed in Sf9 cells (bacculovirus vector) and microtubule depolymerization activity was reported.

Cloning of human Kif1A (ATSV) has been reported (Furlong, et al., Genomics, 33(3):421–29 (1996)). The mouse homolog was expressed in bacculovirus and characterized biochemically (Okada, et al., Cell, 81:769–80 (1995)), and a mouse Kif1A/KHC hybrid (formed for stability) was also expressed in *E. coli* and reportedly had activity in a motility assay (Okada and Hirokawa, Science, 283:1152–7 (1999)).

The human form of KHC (Kinesin Heavy Chain) has been cloned (Navone, et al., J. Cell Biol, 117:1263–75 (1992)). Fujiwara, et al., Biophys J., 69:1563–8 (1995) reportedly expressed human KHC fragment 1–349 in *E. coli* and conducted structural studies on the purified protein. Vale, et al., Nature, 380:451–3 (1996) reportedly expressed human KHC fragment 1–560 in *E.coli* and purified it by phosphocellulose and Mono-Q chromatography. KHC additionally reportedly had motility activity.

Functional studies of enzymes, including but not limited to high-throughput screening for small molecule inhibitors, require significant amounts of active protein. Therefore, it is an object of this invention to provide systems to express kinesins in high quantities. It is further an object of this invention to provide methods for expression and purification of kinesins. It is further an object to provide kinesins which are unglycosylated.

SUMMARY OF THE INVENTION

Accordingly, the present invention provides kinesins which are produced from prokaryotes. In a preferred embodiment, bacterial systems are utilized. Bacterial expression provides the most economical means of obtaining substantial quantities of kinesins without a concern for copurifying a contaminating activity from the expression host since bacteria do not harbor kinesin like proteins.

In one aspect, the invention provides a method of producing a human mitotic kinesin protein comprising a motor domain. The method comprises expressing a nucleic acid comprising a nucleic acid encoding a human mitotic kinesin protein comprising a motor domain in a bacterial cell and substantially purifying said human mitotic kinesin protein.

In another aspect, a method is provided for producing a human kinesin protein comprising a motor domain and at least two epitope tags. The method comprises expressing a nucleic acid encoding a human kinesin protein comprising a motor domain and at least two epitope tags in a prokaryote and substantially purifying said human kinesin protein.

In a further aspect, a method is provided for producing a kinesin protein comprising a motor domain. The method comprises expressing a nucleic acid encoding a kinesin protein comprising a motor domain in a prokaryote and substantially purifying said kinesin protein, wherein said kinesin is selected from the group consisting of Kin2, chromokinesin, Kif1A and MKLP1. It is understood that unless a particular species is named, the term "kinesin" includes homologs thereof which may have different nomenclature among species. For example, the human homolog of Kif1A is termed ATSV, the human homologue of Xenopus Eg5 is termed KSP, and human HSET corresponds to Chinese hamster CHO2.

Also provided herein is a substantially pure unglycosylated human mitotic kinesin protein comprising a motor domain. A substantially pure unglycosylated human kinesin protein comprising a motor domain and at least two epitope tags is also provided. Additionally, a substantially pure unglycosylated kinesin protein comprising a motor domain, wherein said kinesin is selected from the group consisting of Kin2, chromokinesin, Kif1A and MKLP1 is provided.

In one embodiment a prokaryote comprising a nucleic acid comprising a nucleic acid encoding a kinesin selected from the group consisting of chromokinesin, Kin2, and Kif1A is provided. In a further embodiment, a prokaryote comprising a nucleic acid comprising a nucleic acid encoding a human kinesin selected from the group consisting of chromokinesin, Kin2, Kif1A, KSP, CENP-E, MCAK, HSET and Kif15 is provided.

The proteins provided herein can be used in assays provided herein to determine binding properties and modulators of biological activity.

In a further embodiment, provided herein is a substantially purified unglycosylated peptide selected from the group consisting of K335, Q475, D679, FL1, P166, H195, FL2, E433, R494, E658, L360, K491, S553, M329, T340, S405, V465, T488, M1, M2, M3, M4, M5, M6, FL3, A2N370, A2M511, K519, E152.2, Q151.2, Q353 and M472.

DETAILED DESCRIPTION OF THE INVENTION

In accordance with the objects of this invention, methods of producing kinesins are provided herein. In a preferred embodiment, the kinesins are produced from a prokaryote. In a preferred embodiment, the prokaryote is a bacterial cell. Bacterial expression offers several advantages over systems previously utilized, such as, for example, Bacculovirus. The yield of protein is higher, the cost of the expression setup is lower, and creation of alternative expression vectors is easier. The concern of copurifying a contaminating activity from the expression host is also eliminated since bacteria, in contrast to the bacculovirus expression system, do not have kinesin like proteins.

Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E.coli* strain W3110 (ATCC 27,325) and K5 772 (ATCC 53,635). Preferred bacterial strains include *E.coli* BL21 (DE3), BL21 (DE3), pLysS, BL21 (DE3) pLysE.

The kinesins that are produced by the methods herein each comprise a molecular motor domain. Therefore, in one embodiment the kinesin is a full length protein. In another embodiment the kinesin is a kinesin protein comprising a molecular motor domain. A molecular motor protein is a cytoskeletal molecule that utilizes chemical energy to produce mechanical force, and drives the motile properties of the cytoskeleton. The molecular motor domain is usually about 35–45% identical among all kinesin superfamily members, and is approximately 340 amino acids. Vale and Kreis, 1993*, Guidebook to the Cytoskeletal and Motor Proteins* New York: Oxford University Press; Goldstein, 1993, Ann. Rev. Genetics 27: 319–351; Mooseker and Cheney, 1995, Annu. Rev. Cell Biol. 11: 633–675; Burridge et al., 1996, Ann. Rev. Cell Dev. Biol. 12: 463–519.

In one embodiment, the kinesin can be from any species. Thus, unless otherwise specified, kinesin includes homologs thereof. The kinesins therefore include those from Xenopus, Drosophila and other insects, plants, fungi and mammalian cells, with rodents (mice, rats, hamsters, guinea pigs and gerbils being preferred), primates and humans being preferred. In a preferred embodiment, the kinesin is selected from the group consisting of chromokinesin, Kin2, Kif1A, and MKLP1. Preferably Kif1A is expressed as an individual kinesin, i.e., it excludes fusion forms to other kinesins.

In another embodiment, the kinesin is a human kinesin. In a preferred embodiment, the human kinesin is selected from the group consisting of chromokinesin, Kin2, Kif1A, MKLP1, KSP, CENP-E, MCAK, KHC, HSET and Kif15.

In one embodiment, the kinesin protein is a mitotic kinesin protein. In one embodiment, the mitotic kinesin protein is selected from the group consisting of chromokinesin, MKLP1, KSP, CENP-E and MCAK. In a preferred embodiment, the mitotic kinesin protein is a human mitotic kinesin protein.

In another embodiment, the kinesin protein is a non-mitotic kinesin protein. In a preferred embodiment, the non-mitotic kinesin protein is selected from the group consisting of KHC, Kin2 and Kif1A. In a preferred embodiment, the non-mitotic kinesin protein is a human non-mitotic kinesin protein. In a particularly preferred embodiment, the human kinesin protein is selected from the group consisting of chromokinesin, KSP, CENP-E, MCAK, Kin2 and Kif1A. In another particularly preferred embodiment, the kinesin protein is selected from the group consisting of chromokinesin, Kif1A, MKLP1 and Kin2, with chromokinesin and Kin2 being most preferred. It is understood that the groups provided herein necessarily describe groups or individuals within them. For example, the group consisting of KSP, CENP-E, MCAK, Kin2 and Kif1A describes a group consisting of KSP, CENP-E, MCAK and Kin2, or CENP-E as an individual kinesin protein, etc.

In another embodiment, the kinesin protein is a peptide selected from the group consisting of K335, Q475, D679, FL1, P166, H195, FL2, E433, R494, E658, L360, K491, S553, M329, T340, S405, V465, T488, M1, M2, M3, M4, M5, M6, FL3, A2N370, A2M511, K519, E152.2, Q151.2, Q353 and M472. Similarly, it is understood that this group explicitly includes the group of M1, M2, and M6 or K335 and K491, etc.

In one embodiment, the kinesin proteins provided herein have glycosylation patterns which differs from their native form. In a preferred embodiment, the kinesin proteins provided herein are unglycosylated. In a preferred embodiment, the kinesin proteins are expressed in prokaryotes, preferably bacteria, and most preferably *E.coli*, and are thus unglycosylated. However, it is understood that at least in one embodiment an altered native glycosylation pattern can be obtained by a variety of techniques. Removal of carbohydrate moieties present on the kinesin protein may further be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

In another aspect, the kinesins provided herein may have phosphorylation or farnesylation patterns which differ from their native form. In one embodiment, a kinesin is provided which substantially lacks phosphorylation, farneslation and glycosylation.

In one embodiment provided herein, the kinesin protein has at least one and preferably at least two epitope tags. An example of such a chimeric molecule comprises a kinesin protein fused to an epitope tag sequence or a Fc region of an immunoglobulin. The term "epitope tagged" when used herein refers to a chimeric polypeptide comprising a kinesin protein fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes.

Suitable tag polypeptides generally have at least five amino acid residues and usually between about 8 and 50 amino acid residues (preferably, between about 6 and 20 amino acid residues). In one embodiment, such a chimeric molecule comprises a fusion of the kinesin protein with a tag polypeptide which provides an epitope to which an anti-tag antibody can selectively bind. The epitope tag is generally placed at the amino- or carboxyl-terminus of the kinesin protein. The presence of such epitope-tagged forms of the kinesin protein can be detected using an antibody against the tag polypeptide. Also, provision of the epitope tag enables the kinesin protein to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In a preferred embodiment, the kinesin protein comprises an N-terminal T7 epitope tag and a C-terminus myc-epitope and 6-His tag.

In an alternative embodiment, the chimeric molecule may comprise a fusion of the kinesin protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a Kinesin protein in place of at least one variable region within an lg molecule. In a particularly preferred embodiment, the immunoglobulin fusion includes the hinge, CH2 and CH3, or the hinge, CH1, CH2 and CH3 regions of an IgG-1 molecule. For the production of immunoglobulin fusions see also U.S. Pat. No. 5,428,130 issued Jun. 27, 1995.

Additionally, as recognized by the skilled artisan and as will be further apparent below, labels of various sorts may be utilized in the invention. A "label" is a composition detectable by spectroscopic, photochemical, biochemical, immunochemical, or chemical means. For example, useful labels include $^{32}$p, fluorescent dyes, electron-dense reagents, enzymes, biotin, dioxigenin, or haptens and proteins for which antisera or monoclonal antibodies are available. Labels are also described further below.

In a preferred embodiment, a method provided herein includes purifying said kinesin protein. The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. In a preferred embodiment, a protein is considered pure wherein it is determined that there is no contaminating activity.

The nucleic acid (e.g., cDNA or genomic DNA) encoding the kinesin protein may be inserted into a replicable vector for cloning (amplification of the DNA) or for expression.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al, *Nucleic Acid Res.* 19:5081 (1991); Ohtsuka et al., *J. Biol. Chem.* 260:2605–2608 (1985); Cassol et al., 1992; Rossolini et al., *Mol. Cell. Probes* 8:91–98 (1994)). The term nucleic acid is used interchangeably with gene, cDNA, and mRNA encoded by a gene.

Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The kinesin protein may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the kinesin-encoding DNA that is inserted into the vector. The signal sequence may be a prokaryotic signal sequence selected, for example, from the group of the alkaline phosphatase, penicillinase, lpp, or heat-stable enterotoxin II leaders.

Both expression and cloning vectors contain a nucleic acid sequence that enables the vector to replicate in one or more selected host cells. Such sequences are well known for a variety of bacteria. The origin of replication from the plasmid pBR322 is suitable for most Gram-negative bacteria.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. Expression and cloning vectors usually contain a promoter operably linked to the kinesin-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res*., 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding kinesin protein.

The host cells are transformed with the nucleic acids as described herein for kinesin protein production and cultured in nutrient media modified as appropriate for inducing promoters, selecting transformants, or amplifying the genes encoding the desired sequences. The preferred embodiments are demonstrated in the examples below.

Recombinant proteins are expressed by transformed bacteria in large amounts, typically after promoter induction; but expression can be constitutive. Bacteria are grown according to standard procedures in the art. Preferably fresh bacteria cells are used for isolation of protein.

The preferred embodiments for each of the steps of production and purification are further described below in the examples. In particular, preferred lysis, wash and elution buffers are provided. In a preferred embodiment, purification over a Ni-NTA resin leads to a high degree of purification in a single step.

Preferably, the kinesins provided herein as compositions or produced from the methods provided herein have at least one activity of a kinesin protein as further defined below. Preferably the activity is the ability to hydrolyze ATP in a manner stimulated by microtubules.

While it is preferable to produce the kinesins herein in prokaryotic systems, in one aspect, the kinesins herein are produced in eukaryotic systems. In each case, the kinesin is expressed recombinantly. Previous work provided a limited number of kinesin homologs recombinantly, however, herein, each homolog, preferably the human homolog, is expressed recombinantly. For example, methods for expressing human Kin2 in a recombinant system are provided herein. In a preferred embodiment, a vector comprising a human Kin2 sequence is expressed in a eukaryotic cell, and the Kin2 is purified. Similarly, in one embodiment, human chromokinesin, HSET, Kif15, MCAK, Kif1A, MKLP1, CENP-E, KHC or KSP is expressed in a eukaryotic cell. In a preferred embodiment, the eukaryotic cell works in conjunction with a baculovirus system, such as Sf9 cell. The kinesins provided produced by such systems are also provided herein.

In one aspect the specific coding sequences as published and known in the art which encode the kinesin proteins are utilized. However, in an alternative embodiment, a substantially identical sequence encoding a kinesin protein is utilized. The term "substantially identical" in the context of two nucleic acids or polypeptides refers to the residues in the two sequences that have at least 80% identity when aligned for maximum correspondence as measured using one of the following algorithms. Optimal alignment of sequences for comparison can be conducted, e.g., by the local homology algorithm of Smith & Waterman, *Adv. Appl. Math*. 2: 482 (1981), by the homology alignment algorithm of Needleman & Wunsch, *J. Mol. Biol*. 48:443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol*. 35:351–360 (1987). The method used is similar to the method described by Higgins & Sharp, *CABIOS* 5: 151–153 (1989). The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison, e.g., the motor domain. In one example, kinesin proteins were compared to other kinesin protein superfamily sequences using the following parameters: default gap weight (3.00), default gap length weight (0.10), and weighted end gaps.

Another example of algorithm that is suitable for determining sequence similarity is the BLAST algorithm, which is described in Altschul et al., *J. Mol. Biol*. 215: 403–410 (1990).

Software for performing BLAST analyses is publicly available through the National Center for Biotechnology Information (http://www.ncbi.nim.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm performs a statistical analysis of the similarity between two sequences (see, e.g., Karlin & Altschul, *Proc. Nat'l. Acad. Sci. USA* 90: 5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a nucleic acid if the smallest sum probability in a comparison of the test nucleic acid to the nucleic acid is less than about 0.1, more preferably less than about 0.01, and most preferably less than about 0.001. Where the test nucleic acid encodes a kinesin protein, it is considered similar to a specified kinesin nucleic acid if the comparison results in a smallest sum probability of less than about 0.5, and more preferably less than about 0.2.

An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution. An indication that two nucleic acid sequences are substantially identical is that the polypeptide which the first nucleic acid encodes is immunologically cross reactive with the polypeptide encoded by the second nucleic acid. Another indication that two nucleic acid sequences are substantially identical is that the two molecules hybridize to each other under stringent conditions.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium (as the target sequences are generally present in excess, at $T_m$, 50% of the probes are occupied at equilibrium). Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Once expressed and purified if necessary, the kinesin proteins and nucleic acids are useful in a number of applications.

In a preferred embodiment, the kinesin proteins or cells containing the native or modified kinesin proteins are used in screening assays. Production of these important motor proteins in large quantities permits the design of drug screening assays for compounds that modulate kinesin activity.

Screens may be designed to first find candidate agents that can bind to kinesin proteins, and then these agents may be used in assays that evaluate the ability of the candidate agent to modulate kinesin activity. Thus, as will be appreciated by those in the art, there are a number of different assays which may be run; binding assays and activity assays.

Thus, in a preferred embodiment, the methods comprise combining a kinesin protein and a candidate bioactive agent, and determining the binding of the candidate agent to the kinesin protein. Preferred embodiments utilize a human kinesin protein, although other homologs may be used. In a preferred embodiment, the kinesin is unglycosylated or has at least two epitope tags as described herein.

The term "candidate bioactive agent" as used herein describes any molecule, e.g., protein, oligopeptide, small organic molecule, polysaccharide, polynucleotide, etc., with the capability of directly or indirectly altering the bioactivity of kinesin. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. “Amino acid” also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening against kinesin. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or “biased” random peptides. By “randomized” or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents. In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By “nucleic acid” or “oligonucleotide” or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, “Carbohydrate Modifications in Antisense Research”, Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 30 5,034,506, and Chapters 6 and 7, ASC Symposium Series 580, “Carbohydrate Modifications in Antisense Research”, Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or “biased” random nucleic acids. For example, digests of procaryotic or eucaryotic genomes may be used as is outlined above for proteins.

In a preferred embodiment, the candidate bioactive agents are organic chemical moieties, a wide variety of which are available in the literature.

The assays described utilize kinesin proteins as defined herein. In one embodiment, portions of kinesin proteins are utilized, in a preferred embodiment, portions having kinesin activity are used. In addition, the assays described herein may utilize either isolated kinesin proteins or cells comprising the kinesin proteins.

In one of the embodiments of the methods provided herein, the kinesin protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used. Solution based assays are further described below.

In a preferred embodiment, the kinesin protein is bound to the support, and a candidate bioactive agent is added to the assay. Alternatively, the candidate agent is bound to the support and the kinesin protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to a kinesin protein may be done in a number of ways. In a preferred embodiment, the candidate bioactive agent is labelled, and binding determined directly. For example, this may be done by attaching all or a portion of a kinesin protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. kinesin), such as an antibody, peptide, binding partner, ligand, etc. Under certain circumstances, there may be competitive binding as between the bioactive agent and the binding moiety, with the binding moiety displacing the bioactive agent. This assay can be used to determine candidate agents which interfere with binding between kinesin proteins and, for example, a microtubule.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the kinesin protein and thus is capable of binding to, and potentially modulating, the activity of the kinesin protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement. In an alternative embodiment, the candidate bioactive agent is added first, with incubation and washing, followed by the competitor. The absence of binding by the competitor may indicate that the bioactive agent is bound to the kinesin protein with a higher affinity. Thus, if the candidate bioactive agent is labeled, the presence of the label on the support, coupled with a lack of competitor binding, may indicate that the candidate agent is capable of binding to the kinesin protein.

In a preferred embodiment, the methods comprise differential screening to identity bioactive agents that are capable of modulating the activity of the kinesin proteins. In this embodiment, the methods comprise combining a kinesin protein and a competitor in a first sample. A second sample comprises a candidate bioactive agent, a kinesin protein and a competitor. The binding of the competitor is determined for both samples, and a change, or difference in binding between the two samples indicates the presence of an agent capable of binding to the kinesin protein and potentially modulating its activity. That is, if the binding of the competitor is different in the second sample relative to the first sample, the agent is capable of binding to the kinesin protein.

Alternatively, a preferred embodiment utilizes differential screening to identify drug candidates that bind to the native kinesin protein, but cannot bind to modified kinesin proteins. The structure of the kinesin protein may be modeled, and used in rational drug design to synthesize agents that interact with that site. Drug candidates that affect kinesin bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of kinesin protein may also be done. In a preferred embodiment, methods for screening for a bioactive agent capable of modulating the activity of kinesin protein comprise the steps of adding a candidate bioactive agent to a sample of kinesin protein, as above, and determining an alteration in the biological activity of kinesin protein. "Modulating the activity of kinesin protein" includes an increase in activity, a decrease in activity, or a change in the type or kind of activity present. Thus, in this embodiment, the candidate agent should both bind to kinesin protein (although this may not be necessary), and alter its biological or biochemical activity as defined herein. The methods include both in vitro screening methods, as are generally outlined above, and in vivo screening of cells for alterations in the presence, distribution, activity or amount of kinesin protein.

Thus, in this embodiment, the methods comprise combining a kinesin protein sample and a candidate bioactive agent, and evaluating the effect on motor activity. By "kinesin protein activity" or grammatical equivalents herein is meant one of kinesin protein's biological activities, including, but not limited to, its ability to affect ATP hydrolyzation. Other activities include microtubule binding, gliding, polymerazation/depolymerazation (effects on microtubule dynamics), binding to other proteins of the spindle, binding to proteins involved in cell-cycle control, or serving as a substrate to other enzymes, such as kinases or proteases and specific kinesin cellular activities such as chromosome congregation, axonal transport, etc.

Methods of performing motility assays are well known to those of skill in the art (see, e.g., Hall, et al. (1996), *Biophys. J.*, 71: 3467–3476, Turner et al, 1996, *Anal. Biochem.* 242 (1):20–5; Gittes et al, 1996, *Biophys. J.* 70(1): 418–29; Shirakawa et al, 1995, *J. Exp. Biol.* 198: 1809–15; Winkelmann et al., 1995, *Biophys. J.* 68: 2444–53; Winkelmann et a., 1995, *Biophys. J.* 68: 72S, and the like).

In addition to the assays described above, methods known in the art for determining ATPase activity can be used. Preferably, solution based assays are utilized. Alternatively, conventional methods are used. For example, $P^i$ release from kinesin can be quantified. In one preferred embodiment, the ATPase activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 $\mu$L of reaction is quenched in 90 $\mu$L of cold 0.3 M PCA. Phosphate standards are used so data can be converted to mM inorganic phosphate released. When all reactions and standards have been quenched in PCA, 100 $\mu$L of malachite green reagent is added to the to relevant wells in e.g., a microtiter plate. The mixture is developed for 10–15 minutes and the plate is read at an absorbance of 650 nm. If phosphate standards were used, absorbance readings can be converted to mM Pi and plotted over time. Additionally, ATPase assays known in the art include the luciferase assay.

In a preferred embodiment, the activity of the kinesin protein is decreased or increased, with a decrease being preferred. Modulation also includes changes such as the binding characteristics etc. Thus, bioactive agents that are antagonists are preferred in some embodiments, and bioactive agents that are agonists may be preferred in other embodiments.

The components provided herein for the assays provided herein may also be combined to form kits. The kits can be based on the use of the protein and/or the nucleic acid encoding the kinesin proteins.

In this way, bioactive agents are identified. Compounds with pharmacological activity are able to enhance or interfere with the activity of the kinesin protein. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

It is also understood that bioactive compounds may be used in the agricultural arena. For example, inhibitors of kinesins may eliminate fungi which adversely effect agricultural crops. Alternatively, inhibitors of kinesins may be useful in eliminating unwanted plants, i.e., weeds.

Thus, in one embodiment, methods of modulating motor activity in cells or organisms are provided. In one embodiment, the methods comprise administering to a cell an anti-kinesin antibody or other agent identified herein or by the methods provided herein, that reduces or eliminates the biological activity of the endogenous kinesin protein. Alternatively, the methods comprise administering to a cell or organism a recombinant nucleic acid encoding a kinesin protein or modulator including anti-sense nucleic acids.

In one embodiment, the kinesin proteins of the present invention may be used to generate polyclonal and monoclonal antibodies to kinesin proteins, which are useful as described herein. Similarly, the kinesin proteins can be coupled, using standard technology, to affinity chromatography columns. These columns may then be used to purify kinesin antibodies. In a preferred embodiment, the antibodies are generated to epitopes unique to the kinesin protein; that is, the antibodies show little or no cross-reactivity to other proteins. These antibodies find use in a number of applications. For example, the kinesin antibodies may be coupled to standard affinity chromatography columns and used to purify kinesin proteins as further described below. The antibodies may also be used as blocking polypeptides, as outlined above, since they will specifically bind to the kinesin protein.

The anti-kinesin protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the kinesin protein polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-kinesin protein antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the kinesin protein polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against kinesin protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide.

Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-kinesin protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al, *Bio/Technology* 10, 779–783 (1992); Lonberg et al., *Nature* 368 856–859 (1994); Morrison, *Nature* 368 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

Bispecific antibodies are monoclonal, preferably human or humanized, antibodies that have binding specificities for at least two different antigens. In the present case, one of the binding specificities is for the kinesin protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-kinesin protein antibodies of the invention have various utilities. For example, anti-kinesin protein antibodies may be used in diagnostic assays for a kinesin protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp.147–158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-kinesin protein antibodies also are useful for the affinity purification of kinesin protein from recombinant cell culture or natural sources. In this process, the antibodies against kinesin protein are immobilized on a suitable support, such a Sephadex resin or filter paper, using methods well known in the art. The immobilized antibody then is contacted with a sample containing the kinesin protein to be purified, and thereafter the support is washed with a suitable solvent that will remove substantially all the material in the sample except the kinesin protein, which is bound to the immobilized antibody. Finally, the support is washed with another suitable solvent that will release the kinesin protein from the antibody.

The anti-kinesin protein antibodies may also be used in treatment. In one embodiment, the genes encoding the antibodies are provided, such that the antibodies bind to and modulate the kinesin protein within the cell.

All publications, sequences (those of known kinesins, those disclosed or referenced in publications cited herein, or those referenced herein by accession number) and patent applications cited in this specification are herein incorporated by reference as if each individual publication, sequence or patent application were specifically and individually indicated to be incorporated by reference in their entirety. Additionally, wherein accession numbers are provided for sequences herein, the related text in that database entry is also incorporated herein in its entirety.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Example 1

Bacterial Expression Constructs cDNA Cloning.

For all of the kinesin-related proteins provided herein as examples, the full-length human cDNA has been previously described (see Table I). We have cloned cDNAs for all examples by PCR using the primers and cDNA sources indicated on Table I, except for CENP-E which was obtained from Don Cleveland at the Ludwig Institute for Cancer Research, UCSD; see, Yen et al., Nature, 359(6395):536–9 (1992). The nucleotide numbering on Table I corresponds to the Genbank submission numbering scheme. The clones were all sequenced to confirm they were the same as the published genes, although some polymorphisms were present.

Table I

Cloning of Human kinesins

| Huma kinesin | Published Seq: Accession #s & Publication Ref. | Primers for cDNA cloning: 5' primer 3' primer | Nucleotides Included | cDNA Source |
|---|---|---|---|---|
| Chromo-kinesin | AF071592 1165722(GSDB - partial) (SEQ ID NOs:22 and 23) | RACE AP1 primer (Clontech) CCAAACAGGAAACAGTATCCAAGGCAACC (SEQ ID NO:1) | <1–193 | Marathon-Ready HeLa (Clontech) |
| | | TGCCCATCTCGTGAGAAAGC (SEQ ID NO:2) GCTTGACGGAGAGCATGCTG (SEQ ID NO:3) | 76–1178 | HeLa (Our prep) |
| | | ATTGATTACCCAGTTATCGG (SEQ ID NO:4) TGATGACTCCAACTTCAGTG (SEQ ID NO:5) | 1032–3326 | HeLa (Our prep) |
| Kin-2 | Y08319 (SEQ ID NOs:24 and 25) | GCCGAATACATCAAGCAATGGTAAC (SEQ ID NO:6) TCTGGGTATCCTTTAGCAGCAAATG (SEQ ID NO:7) | 2–2088 | Breast tumor (Invitrogen) |
| MKLP1 | X67155 Nislow, et al. 1992 (SEQ ID NOs:26 and 27) | AGCCATGTTGTCAGCGAGAGCTAAG (SEQ ID NO:8) AGGGTCTCTCTGGCTTCTCAGTTTTAGG (SEQ ID NO:9) | 73–2078 | human placenta (Invitrogen) |
| KSP | U37426 (SEQ ID NOs:28 and 29) | CCTTGATTTTTTGGCGGGGACCGTC (SEQ ID NO:10) AAAGGTTGATCTGGGCTCGCAGAGG (SEQ ID NO:11) | 66–3259 | breast tumor (Invitrogen) |
| CENP-E | Z15005 Yen, et al. 1992 (SEQ ID NOs:30 and 31) | | | |
| MCAK | U63743 Kim, et al. 1997 (SEQ ID Nos:32 and 33) | GCGTTTCTCTTCCTTGCTGACTCTC (SEQ ID NO:12) AGAGGCTGGGTGTCAAACCAAACAG (SEQ ID NO:13) | 22–2274 | breast tumor (Invitrogen) |
| Kid | AB017430 (SEQ ID NOs:34 and 35) | GTCGCTGTCGGCTAAGCAAG (SEQ ID NO:14) CTTTGCCCCTGTGACTGTGC | 101–1596 | breast tumor (Invitrogen) |

Table I-continued

Cloning of Human kinesins

| Huma kinesin | Published Seq: Accession #s & Publication Ref. | Primers for cDNA cloning: 5' primer 3' primer | Nucleo-tides Included | cDNA Source |
|---|---|---|---|---|
| | | (SEQ ID NO:15) CTGGATCCCAGCCGCGGGCGGCTCGACG CAG (SEQ ID NO:16) CTCTAGAGAGCAGCTGTCCATGCCCC (SEQ ID NO:17) | 28–248 | HeLa (our prep) |
| HSET | D14678 (partial) (SEQ ID NOs:36 and 37) | GGGCTTGGTGCAAGAGCTTC (SEQ ID NO:18) CACCCCTCACCCGATACATAGAC (SEQ ID NO:19) | 213–1624 | HeLa (our prep) |
| ATSV | X90840 (SEQ ID NOs:38 and 39) | GGGCTCCCACTACTGCGAGG (SEQ ID NO:20) CTCCTCCTCGTTCACCTCCG (SEQ ID NO:21) | 21–2311 | WERI (our prep) |

The sequences from the GenBank accession numbers from Table I and anywhere provided herein, are expressly and explicitly incorporated herein. Other preferred sequences include the following: HsATSV, GenBank accession number X90840; HsHSET/CHO2 partial, GenBank accession number D14678; HsKHC, GenBank accession number X65873; HsKid, GenBank accession number AB017430; and AnBimC, GenBank accession number M32075.

Expression Plasmid Vector Backbones pET23d (Novagen 69748-3) encodes a T7 epitope tag 5' of the polylinker cloning site and a 6-His tag 3' of the polylinker cloning site. We constructed pET23dmyc by inserting the annealed oligonucleotides described below into the XhoI site of pET23d. This creates coding sequence for the myc epitope tag in-frame with the 6-His tag.

Annealed oligonucleotides for pET23dmyc:

sense: TCGAGGGTACCGAGCAGAAGCTGATCAGCGAGGAGGACCTGA (SEQ ID NO:40)

antisense: TCGATCAGGTCCTCCTCGCTGATCAGCTTCTGCTCGGTACCC (SEQ ID NO:41)

pET15b (Novagen 69661-3) encodes a HIS tag 5' of the polylinker cloning site.

Subcloning of Genes into Expression Vectors

Using the human kinesin clones obtained by the methods described above as a template, PCR was used to amplify portions of the coding sequence, and the PCR product was inserted into the bacterial expression plasmids described above by restriction enzyme digest and ligation. Several constructs of different lengths were developed for each kinesin (see Table II, the column "Residues Included" describes the starting and ending amino acid in one-letter code and amino acid number). All of the resulting constructs encode the motor domain, and vary in the amount of flanking sequence. The PCR primers detailed on Table II are designed such that resulting constructs encode a protein with a C-terminal 6-His tag (for those constructs built into pET23d) or the combination myc-epitope/6-His tag (for those constructs built into pET23dmyc), or an N-temrinal 6-His tag (for those constructs built into pET15b). All constructs made using the pET23d or the pET23dmyc vector, except those cloned into the NcoI site, also encode a protein with an N-terminal T7 epitope tag.

TABLE II

Subcloning of Human kinesins into Bacterial Expression Plasmids:

| Kinesin | Construct Name | 5' primer. 3' primer | Residues Included | Cloning sites | Host Vector |
|---|---|---|---|---|---|
| Chromo-kinesin | K335 | TAGCCATGGAAGAGGTGAAGGGAATTC (SEQ ID NO:42) CCGCTCGAGTTTCTTGCTCTGTC (SEQ ID NO:43) | E2-K335 | 5': NcoI 3': XhoI | pET23dmyc |
| Chromo-kinesin | Q475 | TAGAAGCTTGGAAGAGGTGAAGGG (SEQ ID NO:44) TAGAAGCTTCTGGGTAATCAATTG (SEQ ID NO:45) | E2-Q475 | 5' Hind III 3': HindIII | pET23dmyc |
| Chromo-kinesin | D679 | TAGAAGCTTGGAAGAGGTGAAGGG (SEQ ID NO:46) TAGAAGCTTGTCTCGTTCTTTTAAC (SEQ ID NO:47) | E2-D679 | 5' Hind III 3': HindIII | pET23dmyc |
| Chromo-kinesin | FL1 | TAGAAGCTTGGAAGAGGTGAAGGG (SEQ ID NO:48) TAGAAGCTTGTGGGCCTCTTCTTCG (SEQ ID NO:49) | E2-H1229 | 5' Hind III 3': HindIII | pET23dmyc |
| Kin2 | P166 | TACGGATCCCAAATTATGAAATTATG (SEQ ID NO:50) | P166-A532 | 5': BamHI 3': HindIII | pET23dmyc |

TABLE II-continued

Subcloning of Human kinesins into Bacterial Expression Plasmids:

| Kinesin | Construct Name | 5' primer. 3' primer | Residues Included | Cloning sites | Host Vector |
|---|---|---|---|---|---|
| | | TACAAGCTTAGCAGTTGGATCTACAGTC (SEQ ID NO:51) | | | |
| Kin2 | H195 | TACGGATCCATAGGATATGTGTGTGTG (SEQ ID NO:52) TACAAGCTTAGCAGTTGGATCTACAGTC (SEQ ID NO:53) | H195-A532 | 5': BamHI 3': HindIII | pET23dmyc |
| Kin2 | FL2 | CTCCATGGTAACATCTTTAAATGAAGATAATG (SEQ ID NO:54) CTAAGCTTAAGGGCACGGGGTCTCTTCGGGTTG (SEQ ID NO:55) | M1-L679 | 5': Ncol 3': HindIII | pET23dmyc |
| MKLP1 | E433 | ATCCATGGCGAGAGCTAAGACACCCCGGAAACC (SEQ ID NO:56) ATGCGGCCGCTTCTTGAGTCACTTCCGCAAATCTC (SEQ ID NO:57) | A4-E433 | 5': Ncol 3': Notl | pET23dmyc |
| MKLP1 | R494 | ATCCATGGCGAGAGCTAAGACACCCCGGAAACC (SEQ ID NO:58) ATGCGGCCGCCCTTGGAAGTGTCTGCTCATCGTTG (SEQ ID NO:59) | A4-R494 | 5': Ncol 3': Notl | pET23dmyc |
| MKLP1 | E658 | ATCCATGGCGAGAGCTAAGACACCCCGGAAACC (SEQ ID NO:60) ATGCGGCCGCTTCAGTAACAATAGCCTTCAGTTG (SEQ ID NO:61) | A4-E658 | 5': Ncol 3': Notl | pET23dmyc |
| KSP | L360 | ATCCATGGCGTGCCAGCCAAATTCGTCTGCG (SEQ ID NO:62) ATCTCGAGCAATATGTTCTTTGCTCTATGAGC (SEQ ID NO:63) | M1-L360 | 5': Ncol 3': Xhol | pET23dmyc |
| KSP | K491 | ATCCATGGCGTGCCAGCCAAATTCGTCTGCG (SEQ ID NO:64) ATCTCGAGTTTCTCCTCAGTACTTTCCAAAGC (SEQ ID NO:65) | M1-K491 | 5': Ncol 3': Xhol | pET23dmyc |
| KSP | S553 | ATCCATGGCGTGCCAGCCAAATTCGTCTGCG (SEQ ID NO:66) ATCTCGAGGCTGCCATCCTTAATTAATTCTTCC (SEQ ID NO:67) | M1-S553 | 5': Ncol 3': Xhol | pET23dmyc |
| CENP-E | M329 | CTGGATCCCGGCGGAGGAAGGAGCCGTGGCC (SEQ ID NO:68) CACTCGAGCATATATTTAGCAGTACTGGC (SEQ ID NO:69) | A2-M329 | 5': BamHI 3': Xhol | pET23d |
| CENP-E | T340 | CTGGATCCCGGCGGAGGAAGGAGCCGTGGCC (SEQ ID NO:70) CACTCGAGAGTTGATACCTCATTAACATAAGGAG (SEQ ID NO:71) | A2-T340 | 5': BamHI 3': Xhol | pET23d |
| CENP-E | S405 | CTGGATCCCGGCGGAGGAAGGAGCCGTGGCC (SEQ ID NO:72) CACTCGAGAGAAGAGGTCACCAGCATCCG (SEQ ID NO:73) | A2-S405 | 5': BamHI 3': Xhol | pET23d |
| CENP-E | V465 | CTGGATCCCGGCGGAGGAAGGAGCCGTGGCC (SEQ ID NO:74) CACTCGAGGACAGATTCATCAATTTCTCG (SEQ ID NO:75) | A2-V465 | 5': BamHI 3': Xhol | pET23d |
| CENP-E | T488 | CTGGATCCCGGCGGAGGAAGGAGCCGTGGCC (SEQ ID NO:76) CACTCGAGTGTTGCTGGATTCCATTCTATC (SEQ ID NO:77) | A2-T488 | 5': BamHI 3': Xhol | pET23d |
| MCAK | M1 | CTGGATCCGGAGGAAATCATGTCTTGTGAAG (SEQ ID NO:78) CACTCGAGTGGAATCAGCGCCCCGTTAGAG (SEQ ID NO:79) | R189-P617 | 5': BamHI 3': Xhol | pET23dmyc |
| MCAK | M2 | CTGGATCCCAAACTGGGAATTTGCCCGAATG (SEQ ID NO:80) CACTCGAGTGGAATCAGCGCCCCGTTAGAG (SEQ ID NO:81) | P228-P617 | 5': BamHI 3': Xhol | pET23dmyc |
| MCAK | M3 | CTGGATCCACAGAATATGTGTCTGTGTTAGG (SEQ ID NO:82) CACTCGAGTGGAATCAGCGCCCCGTTAGAG (SEQ ID NO:83) | H257-P617 | 5': BamHI 3': Xhol | pET23dmyc |
| MCAK | M4 | CTGGATCCGGAGGAAATCATGTCTTGTGAAG (SEQ ID NO:84) CACTCGAGTGGTCCTTGCTGTATGATCTC (SEQ ID NO:85) | R189-P660 | 5': BamHI 3': Xhol | pET23dmyc |
| MCAK | M5 | CTGGATCCCAAACTGGGAATTTGCCCGAATG (SEQ ID NO:86) CACTCGAGTGGTCCTTGCTGTATGATCTC (SEQ ID NO:87) | P228-P660 | 5': BamHI 3': Xhol | pET23dmyc |

TABLE II-continued

Subcloning of Human kinesins into Bacterial Expression Plasmids:

| Kinesin | Construct Name | 5' primer. 3' primer | Residues Included | Cloning sites | Host Vector |
|---|---|---|---|---|---|
| MCAK | M6 | CTGGATCCACAGAATATGTGTCTGTGTTAGG (SEQ ID NO:88) CACTCGAGTGGTCCTTGCTGTATGATCTC (SEQ ID NO:89) | H257-P660 | 5': BamHI 3': XhoI | pET23dmyc |
| MCAK | FL3 | CTCCATGGACTCGTCGCTTCAGGCCCGC (SEQ ID NO:90) CTCTCGAGCTGGGGCCGTTTCTTGCTGCTTATTTG (SEQ ID NO:91) | M3-Q725 | 5': NcoI 3': XhoI | pET23dmyc |
| Kid | A2N370 | CTGGATCCCAGCCGCGGGCGGCTCGACGCAG (SEQ ID NO:92) CACTCGAGATTGATCACCTCCTTGGACCTG (SEQ ID NO:93) | A2-N370 | 5': BamHI 3': XhoI | pET23dmyc |
| Kid | A2M511 | CTGGATCCCAGCCGCGGGCGGCTCGACGCAG (SEQ ID NO:94) CACTCGAGCATTGTGGGACAATGGTTCTC (SEQ ID NO:95) | A2-M511 | 5': BamHI 3': XhoI | pET23dmyc |
| HSET | K519 | TCGGATCCTTGGTGCAAGAGCTTCAG (SEQ ID NO:96) CACTCGAGCTTCCTGTTGGCCTGAGC (SEQ ID NO:97) | L72-K519 | 5': BamHI 3' XhoI | pET23dmyc |
| HSET | E152.2 | CATGCCATGGAACTCAAGGGCAAC (SEQ ID NO:98) CACTCGAGCTTCCTGTTGGCCTGAGC (SEQ ID NO:99) | E152-K519 | 5': NcoI 3': XhoI | pET23d |
| HSET | Q151.3 | GGATATCCATATGCAGGAACTCAAGGGCAAC (SEQ ID NO:100) GCAGGATCCTCACTTCCTGTTGGCCTGAG (SEQ ID NO:101) | Q151-K519 | 5': NdeI 3': BamHI | pET15b |
| ATSV | Q353 | CTGGATCCCCGGGGCTTCGGTGAAGGTGGCG (SEQ ID NO:102) CACTCGAGCTGCTTGGCCCGGTCAGCATAC (SEQ ID NO:103) | G3-Q353 | 5': BamHI 3': XhoI | pET23dmyc |
| ATSV | M472 | CTGGATCCCCGGGGCTTCGGTGAAGGTGGCG (SEQ ID NO:104) CACTCGAGCATCTCGGCCAGCAGGGCTTC (SEQ ID NO:105) | G3-M472 | 5': BamHI 3': XhoI | pET23dmyc |

The construct name, such as "Q475", is used herein to identify the construct initially identified by the "residues included" and the GenBank accession number provided herein. As noted in the procedures provided herein, the vector also supplies an initiation methionine and epitope tags. It is understood that when the construct is named in the context of a peptide, such as a peptide selected from the group consisting of Q475 and D679, the peptide has a sequence encoded by the construct using the universal code as is known in the art.

Protein Production & Purification

This section details a protocol that we have used to produce the kinesin protein fragments detailed in Table II. Variations for particular kinesins are noted in the protocol. For many of the examples (Chromokinesin, Kin2), the protocols are quite similar. However, we have found that modifications to the protocol are preferred in certain cases. For example, for MCAK, the PIPES-based buffers were not suitable for production of active proteins, and therefore the success of Tris-based buffers were discovered.

Expression Protocol

Typical culture volume for a preparation is 1–2 liters, with each 500 ml of culture being contained in a 2 liter flask to promote aeration. Typical culture media is LB medium with 10 ppm antifoam. Alternatively, TB medium is also suitable. Media is inoculated in the morning with a single fresh colony of bacterial cells (for example, *E. coli* strain BL21 (DE3)plysS) harboring an expression plasmid (for example, those plasmids described above). For all kinesins, cultures are grown at 37° C. with shaking until $OD_{600}$ reaches about 0.8 at which point cultures continue to shake at room temperature for about 30–45 minutes. To provide a pre-induction sample, 500 μl of culture is spun down and frozen at −20° C. at this point. To induce protein production, IPTG is added to 0.2 mM (or 0.5 mM for CENP-E and MCAK), and shaking is continued overnight. On the following morning (after 12–16 hours), another 500 μl sample is collected, spun down, and frozen at −20° C. The remainder of cells are harvested by centrifugation at 4° C. for 30 minutes (for example, using a Beckman Allegra 6R Centrifuge at 3000 rpm or using a JLA 10 rotor in a Beckman Avanti J-25 centrifuge at 5000 rpm).

Purification Protocol

The preferred buffers for each kinesin are described at the end of this section. From this point, all solutions are kept on ice and/or in a 4° C. environment. Cell pellets are resuspended in lysis buffer supplemented with protease inhibitors (for example 1× concentrations of Complete EDTA-free protease inhibitors (Boehringer 1836 170)). 20 ml of lysis buffer is used for every 1 liter of culture. Dounce homogenization is conducted to ensure complete resuspension. At this point it is possible to freeze the cell suspension in liquid nitrogen and store it at −80° C. If cell suspension is frozen at this point, fresh DTT (and ATP for MCAK) are added upon thawing. Cells are lysed with a microfluidizer by running 2 passes, 7–8 cycles each at 80 psi. If cell suspension had been frozen, only 1 pass of 3 cycles is used. About 10 mls of extra lysis buffer is passed through the microfluidizer chamber to rinse it. Lysate is clarified by centrifugation (for example, for 45 minutes at 22,000 rpm in a JA25.50 rotor in a Beckman Avanti J-25 Centrifuge, or for 30–45 minutes at 30,000 rpm in a 45 Ti Rotor in a Beckman Optima LE-80K Ultracetnrifuge).

For MCAK, 0.5 ml of Ni-NTA resin (Qiagen 31014) is used for every 1 liter of culture. For all others, 1.5 ml of Ni-NTA resin is used for every 1 liter of culture. Resin is equilibrated with lysis buffer by washing 2 times with 15 ml of buffer without DTT and protease inhibitors. During these washes, resin is collected by spinning at 600–700 rpm for about 2 minutes in a bench-top centrifuge. 100 $\mu$l of lysate is reserved before addition to the resin. Remainder of clarified lysate is added to the resin and incubated at 4° C. for hour (20 minutes for MCAK) with rocking.

For Chromokinesin, Kin2, MKLP1, KSP and CENP-E, resin is collected by spinning at 600–700 rpm for about 2 minutes in a bench-top centrifuge. Supernatant is removed and a 100 $\mu$l sample is saved. Resin is resuspended in 5–10 ml lysis bufferwith 0.1×protease inhibitors, and slurry is poured into a column For MCAK, lysate/resin slurry is directly poured into a column (for example, BioRad 1 cm ID EconoColumn), and flowthrough is collected and a 100 $\mu$l sample of flowthrough is reserved.

Column is then washed (using either gravity flow or a peristaltic pump at 1 ml/min) with 50 ml of lysate buffer. Column is then washed with 10 ml of wash buffer. Protein is eluted from column with 8 ml of elution buffer containing 0.1×protease inhibitors, and 1 ml fractions are collected. Fractions containing protein peak as measured by Bradford assay are pooled, and protein is diluted to 2 mg/ml with wash buffer with 0.1×protease inhibitors (for KSP, do not include Imidazole in wash buffer used for dilution). Aliquots are quick-frozen in liquid nitrogen and stored at −80° C.

Buffers Used in Purification Procedure

Chromokinesin, Kin2, MKLP-1, HSET, ATSV Buffers:

Lysis Buffer: 50 mM tris/HCl; 250 mM NaCl; 10 mM Imidazole; 2 mM $MgCl_2$; 1 mM EGTA; 1 mM DTT; pH 7.4.

Wash Buffer: 50 mM PIPES; 10% Sucrose; 100 mM NaCl; 2 mM $MgCl_2$; 1 mM EGTA; 1 mM DTT; pH 6.8 with NaOH.

Elution Buffer: 50 mM PIPES; 10% Sucrose; 300 mM Imidazole; 100 mM NaCl; 2 mM $MgCl_2$; 1 mM EGTA; 1 mM DTT; pH 6.8 with NaOH.

KSP Buffers:

Lysis Buffer: 50 mM tris/HCl; 250 mM NaCl; 10 mM Imidazole; 2 mM $MgCl_2$; 1 mM EGTA; 1 mM DTT; pH 7.4.

Wash Buffer: 50 mM PIPES; 10% Sucrose; 40mM Imidazole, 100 mM NaCl; 2 mM $MgCl_2$; 1 mM EGTA; 1 mM DTT; pH 6.8 with NaOH.

Elution Buffer: 50 mM PIPES; 10% Sucrose; 200 or 250 mM Imidazole; 100 mM NaCl; 2 mM $MgCl_2$; 1 mM EGTA; 1 mM DTT; pH 6.8 with NaOH.

CENP-E Buffers:

Lysis Buffer: 50 mM tris/HCl; 250 mM NaCl; 10 mM Imidazole; 2 mM $MgCl_2$; 1 mM EGTA; 1 mM DTT; 0. mM ATP, pH 7.4.

Wash Buffer: 50 mM PIPES; 10% Sucrose; 100 mM NaCl; 2 mM $MgCl_2$; 1 mM EGTA; 1 mM DTT; pH 6.8 with NaOH.

Elution Buffer: 50 mM PIPES; 10% Sucrose; 300 mM Imidazole; 100 mM NaCl; 2 mM $MgCl_2$; 1 mM EGTA; 1 mM DTT; pH 6.8 with NaOH.

MCAK Buffers:

Lysis Buffer: 50 mM tris/HCl; 50 mM NaCl; 10 mM Imidazole; 5 mM MgCl2; 1 mM EGTA; 1 mM DTT; 1 mM ATP pH 6.8.

Wash Buffer: 50 mM tris/HCl; 50 mM NaCl; 50 mM Imidazole; 5mM MgCl2 1 mM EGTA; 1 mM DTT; 1 mM ATP, 20%sucrose; pH 6.8.

Elution Buffer: 50 mM tris/HCl; 50 mM NaCl; 100 mM Imidazole; 5 mM MgCl2 1 mM EGTA; 1 mM DTT; 1 mM ATP; 20% sucrose; pH 6.8.

Results of Purification:

Successful application of this protocol is measured by the yield, purity and activity of the desired protein. Table III describes results using the protocol detailed above. We have assessed "activity" by the ability of the protein to hydrolyze ATP in a manner stimulated by microtubules. The motor domain of the kinesins is responsible for this enzymatic process. All of the constructs contain the motor domain, and differ in the amount of flanking sequence. We find that the character of the fragment can affect yield and purity (see Table III ). We find that the purification conditions used can affect yield, purity and activity. The protocol above describes the most successful conditions, and Table III describes the outcome resulting from the preferred protocol. There were also conditions tested that were not successful. For example, for KSP, elution buffer containing varying amounts of imidazole were tested. 50 mM and 100 mM imidazole-containing elution buffers failed to elute most protein, so yields were low. However, 200 mM and 250 mM imidazole-containing elution buffers resulted in high yields of active protein. As another example, for MCAK, the PIPES-based buffers were not suitable for production of active proteins as discussed above, therefore successful results were discovered with Tris-based buffers.

TABLE III

Production and Purification Results:

| Kinesin | Construct Name | Residues Included | Production | Activity |
|---|---|---|---|---|
| Chromo-kinesin | K335 | E2-K335 | Expresses well | Low |
| Chromo-kinesin | Q475 | E2-Q475 | Expresses well | High |
| Chromo-kinesin | D679 | E2-D679 | Expresses well | High |
| Chromo-kinesin | FL1 | E2-H1229 | Does not express well | n/a |
| Kin2 | P166 | P166-A532 | Expresses well | Yes |
| Kin2 | H195 | H195-A532 | Expresses well | Yes |
| Kin2 | FL2 | M1-L679 | Does not express well | n/a |
| MKLP1 | E433 | A4-E433 | Expresses well | Yes |
| MKLP1 | R494 | A4-R494 | Expresses well | Yes |
| MKLP1 | E658 | A4-E658 | Does not express well | n/a |
| KSP | L360 | M1-L360 | Expresses well | Yes |
| KSP | K491 | M1-K491 | Expresses well | Yes |
| KSP | S553 | M1-S553 | Not as well as L360 and K491 | n/a |
| CENP-E | M329 | A2-M329 | Expresses well, but relatively impure | Yes |
| CENP-E | T340 | A2-T340 | Expresses well | Yes |
| CENP-E | S405 | A2-5405 | Expresses well | Yes |
| CENP-E | V465 | A2-V465 | Expresses | Yes |

TABLE III-continued

Production and Purification Results:

| Kinesin | Construct Name | Residues Included | Production | Activity |
|---|---|---|---|---|
| | | | well, but relatively impure | |
| CENP-E | T488 | A2-T488 | Expresses well, but relatively impure | Yes |
| MCAK | M1 | R189-P617 | Expresses well, low solubility | Low |
| MCAK | M2 | P228-P617 | Expresses well, low solubility | Low |
| MCAK | M3 | H257-P617 | Expresses well, low solubility | Moderate |
| MCAK | M4 | R189-P660 | Expresses well, low solubility | Low |
| MCAK | M5 | P228-P660 | Expresses well, low solubility | Low |
| MCAK | M6 | H257-P660 | Expresses well, low solubility | Moderate |
| MCAK | FL3 | M3-Q725 | Expresses well, low solubility | Low |
| Kid | A2N370 | A2-N370 | Expresses well | Not tested |
| Kid | A2M511 | A2-M511 | Expresses well | Not tested |
| HSET | K519 | L72-K519 | Low expression | Low |
| HSET | E152.2 | E152-K519 | Expresses well | Yes |
| HSET | Q151.3 | Q151-K519 | Expresses well | Yes |
| ATSV | Q353 | G3-Q353 | Expresses well | High |
| ATSV | M472 | G3-M472 | Expresses well | Low |

We claim:

1. A substantially pure unglycosylated human kinesin protein comprising a motor domain and at least three epitope tags.

2. The protein of claim 1, wherein said kinesin protein is selected from The group consisting of KSP or SEQ ID NO:29, CENP-E of SEQ ID NO:31, MKLPI of SEQ ID NO:27, HSET of SEQ ID NO:37, Kin2 of SEQ ID NO:25, Kif1A of SEQ ID NO:39 and MCAK of SEQ ID NO:33.

3. The protein of claim 2, wherein said kinesin protein is KSP of SEQ ID NO:29.

4. The protein of claim 3, wherein said kinesin protein consists of residues 1–491 of KSP of SEQ ID NO:29.

5. The protein of claim 3, wherein said kinesin protein consists of residues 1–360 of SEQ ID NO:29.

6. The protein of claim 2, wherein said kinesin protein in CENP-E of SEQ ID NO:31.

7. The protein of claim 6, wherein said kinesin protein consists of residues 2–340 of CENP-E of SEQ ID NO:31.

8. The protein of claim 6, wherein said kinesin protein consists of residues 2–405 of CENP-E of SEQ ID NO:31.

9. The protein of claim 6, wherein said kinesin protein consists of residues 2–465 of CENP-E of SEQ ID NO:31.

10. The protein of claim 6, wherein said kinesin protein consists of residues 2–488 of CENP-E of SEQ ID NO:31.

11. The protein of claim 6, wherein said kinesin protein consists of residues 2–329 of CENP-E of SEQ ID NO:31.

12. The protein of claim 2, wherein said kinesin protein is MKLPI of SEQ ID NO:27.

13. The protein of claim 12, wherein said kinesin protein consists of residues 4–433 of MKLPI of SEQ ID NO:27.

14. The protein of claim 12, wherein said kinesin protein consists of residues 4–494 of MKLPI of SEQ ID NO:27.

15. The protein of claim 2, wherein said kinesin protein is HSET of SEQ ID NO:37.

16. The protein of claim 15, wherein said kinesin protein consists of residues 152–519 of HSET of SEQ ID NO:37.

17. The protein of claim 15, wherein said kinesin protein consists of residues 151–519 of HSET of SEQ ID NO:37.

18. The protein of claim 2, wherein said kinesin protein is Kin2 of SEQ ID NO:25.

19. The protein of claim 18, wherein said kinesin protein consists of residues 166–532 of Kin2 of SEQ ID NO:25.

20. The protein of claim 18, wherein said kinesin protein consists of residues 195–532 of Kin2 of SEQ ID NO:25.

21. The protein of claim 2, wherein said kinesin protein is MCAK of SEQ ID NO:33.

22. The protein of claim 21, wherein said kinesin protein consists of residues 2574–617 to MCAK of SEQ ID NO:33.

23. The protein of claim 21, wherein said kinesin protein consists of residues 257–660 of MCAK of SEQ ID NO:33.

24. The protein of claim 2, wherein said kinesin protein is Kif1a of SEQ ID NO:39.

* * * * *